(12) United States Patent
McCullough et al.

(10) Patent No.: US 10,583,245 B2
(45) Date of Patent: Mar. 10, 2020

(54) DRUG DELIVERY DEVICE WITH VACUUM ASSISTED SECUREMENT AND/OR FEEDBACK

(71) Applicant: AMGEN INC., Thousand Oaks, CA (US)

(72) Inventors: Adam B. McCullough, Westlake Village, CA (US); Lawrence S. Ring, Laguna Beach, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/544,488

(22) PCT Filed: Feb. 17, 2016

(86) PCT No.: PCT/US2016/018149
§ 371 (c)(1),
(2) Date: Jul. 18, 2017

(87) PCT Pub. No.: WO2016/133947
PCT Pub. Date: Aug. 25, 2016

(65) Prior Publication Data
US 2018/0036476 A1 Feb. 8, 2018

Related U.S. Application Data

(60) Provisional application No. 62/117,420, filed on Feb. 17, 2015.

(51) Int. Cl.
*A61M 5/142* (2006.01)
*A61M 5/145* (2006.01)
*A61M 5/158* (2006.01)

(52) U.S. Cl.
CPC ...... *A61M 5/14248* (2013.01); *A61M 5/1452* (2013.01); *A61M 5/158* (2013.01);
(Continued)

(58) Field of Classification Search
CPC ............ A61M 5/14278; A61M 5/1452; A61M 5/158; A61M 5/14586; A61M 5/14593;
(Continued)

(56) References Cited

U.S. PATENT DOCUMENTS

| 3,147,622 A | 9/1964 | Weir |
|---|---|---|
| 9,943,653 B2 | 4/2018 | Kamen et al. |

(Continued)

FOREIGN PATENT DOCUMENTS

| DE | 2936579 A1 | 3/1981 |
|---|---|---|
| JP | H06504215 A | 5/1994 |

(Continued)

OTHER PUBLICATIONS

International Preliminary Report on Patentability and Written Opinion for International Application No. PCT/US2016/018149, dated Aug. 22, 2017.

(Continued)

*Primary Examiner* — Rebecca E Eisenberg
*Assistant Examiner* — Tasnim Mehjabin Ahmed
(74) *Attorney, Agent, or Firm* — Marshall, Gerstein & Borun LLP

(57) ABSTRACT

A drug delivery device includes a housing with at least one pressure communication channel or aperture, which distributes a negative fluid pressure across its base to draw tissue against the device. The device can also include a porous, adhesive layer over the channel(s) or aperture(s), for attaching to tissue. The device can also include a pressure sensor for determining whether there is proper attachment. Further, a bladder may be used instead of the adhesive layer for attaching the device. The bladder, in a partially inflated state, can apply constant pressure across a contact surface causing a flexible adhesive layer attached to the bladder to confirm and adhere to the tissue. Subsequent evacuation of the (Continued)

bladder causes it to deflate and collapse or retract, thereby causing the flexible adhesive layer to pull and stretch the tissue toward the base.

22 Claims, 33 Drawing Sheets

(52) U.S. Cl.
CPC ............. *A61M 2005/14252* (2013.01); *A61M 2005/1586* (2013.01); *A61M 2205/0216* (2013.01); *A61M 2205/13* (2013.01); *A61M 2205/3306* (2013.01); *A61M 2205/3344* (2013.01)

(58) Field of Classification Search
CPC ........... A61M 2005/14252; A61M 2005/1586; A61M 2005/14264; A61M 2205/0216; A61M 2205/13; A61M 2205/3306; A61M 2205/3344
See application file for complete search history.

(56) References Cited

U.S. PATENT DOCUMENTS

| | | | |
|---|---|---|---|
| 2004/0092875 A1 | 5/2004 | Kochamba | |
| 2004/0236248 A1 | 11/2004 | Svedman | |
| 2004/0236249 A1 | 11/2004 | Hilgers et al. | |
| 2006/0089620 A1* | 4/2006 | Gibson | A61M 5/14276 604/891.1 |
| 2006/0264926 A1* | 11/2006 | Kochamba | A61M 5/14248 606/41 |
| 2007/0118096 A1* | 5/2007 | Smith | A61B 5/445 604/541 |
| 2007/0219532 A1* | 9/2007 | Karpowicz | A61M 1/0031 604/540 |
| 2007/0265586 A1* | 11/2007 | Joshi | A61M 1/0031 604/313 |
| 2009/0088823 A1 | 4/2009 | Barak et al. | |
| 2009/0155760 A1 | 6/2009 | Fujisato et al. | |
| 2013/0060233 A1 | 3/2013 | O'Connor et al. | |
| 2014/0008929 A1 | 1/2014 | Cho | |
| 2015/0011965 A1 | 1/2015 | Cabiri | |

FOREIGN PATENT DOCUMENTS

| | | | |
|---|---|---|---|
| JP | 2005507716 A | 3/2005 | |
| JP | 2005087520 A | 4/2005 | |
| JP | 2005518253 A | 6/2005 | |
| JP | 2014509955 A | 4/2014 | |
| JP | 2014168695 A | 9/2014 | |
| WO | WO-92/11879 A1 | 7/1992 | |
| WO | WO-1994023777 A1 | 10/1994 | |
| WO | WO-9959665 A1 | 11/1999 | |
| WO | WO-2006031500 A2 | 3/2006 | |
| WO | WO-2006/121921 A2 | 11/2006 | |
| WO | WO-2008/114218 A2 | 9/2008 | |
| WO | WO-2011/163264 A2 | 12/2011 | |
| WO | WO-2013136327 A1 | 9/2013 | |

OTHER PUBLICATIONS

Canadian Office Action for Application No. 2,976,935, dated Apr. 5, 2018.
Japanese Office Action for Application No. 2017-542094, with a Translation of Notice of Rejection, dated Feb. 13, 2018.
Examination Report No. 2 for Australian Application No. 2016220141, dated Mar. 26, 2018.
International Search Report for International Application No. PCT/US2016/018149, dated Jun. 28, 2016.
Written Opinion of the International Searching Authority, International Application No. PCT/US2016/018149, dated Jun. 28, 2016.
Examination Report No. 1 for Australian Application No. 2016220141, dated Nov. 30, 2017.
Canadian Office Action for Application No. 2,976,935, dated Oct. 28, 2018.
Australian Patent Application No. 2019-219989, Examination Report No. 1, dated Aug. 19, 2019.
European Patent Application No. 19178027.9, Extended European Search Report, dated Sep. 23, 2019.
Japanese Patent Application No. 2018-242196, Office Action, dated Nov. 19, 2019.

\* cited by examiner

PRESSURE WITHIN SYSTEM (psia)

| TRANSITION | P_supply | P_1 | P_2 | P_3 | P_4 | P_A | P_B | P_C | P_ambient |
|---|---|---|---|---|---|---|---|---|---|
| Initial, Open P_supply | 3 | 3 | 14 | 14 | 14 | 14 | 14 | 14 | 14 |
| Check valve 50-2 opens, branch line 56-1 closes | 3 | 3 | 5 | 14 | 14 | 12.5 | 14 | 14 | 14 |
| Check valve 52-2 opens, branch line 56-2 closes | 3 | 3 | 5 | 7 | 14 | 12.5 | 12.5 | 14 | 14 |
| Check valve 54-2 opens, branch line 56-3 closes | 3 | 3 | 5 | 7 | 9 | 12.5 | 12.5 | 12.5 | 14 |
| Supply vented to ambient | 14 | 14 | 5 | 7 | 9 | 12.5 | 12.5 | 12.5 | 14 |
| Seal at branch line 56-3 interrupted | 14 | 14 | 5 | 7 | 9 | 12.5 | 12.5 | 14 | 14 |

FIG. 5B

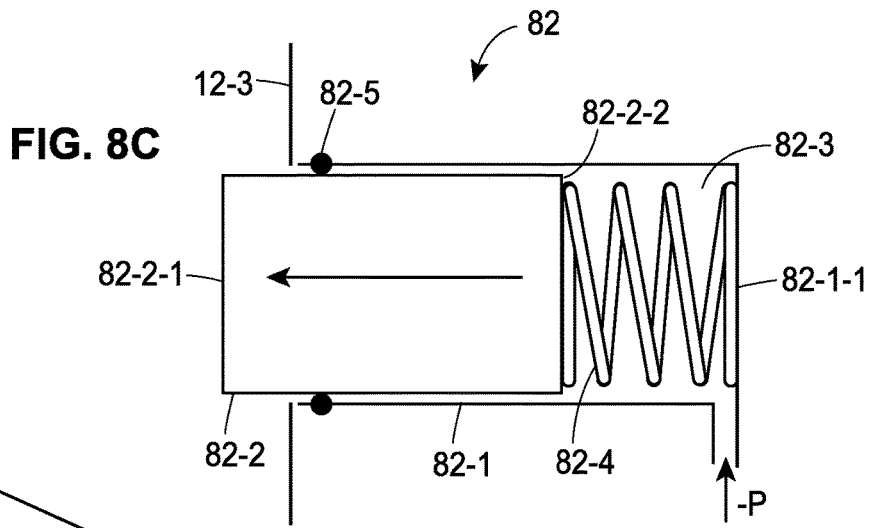
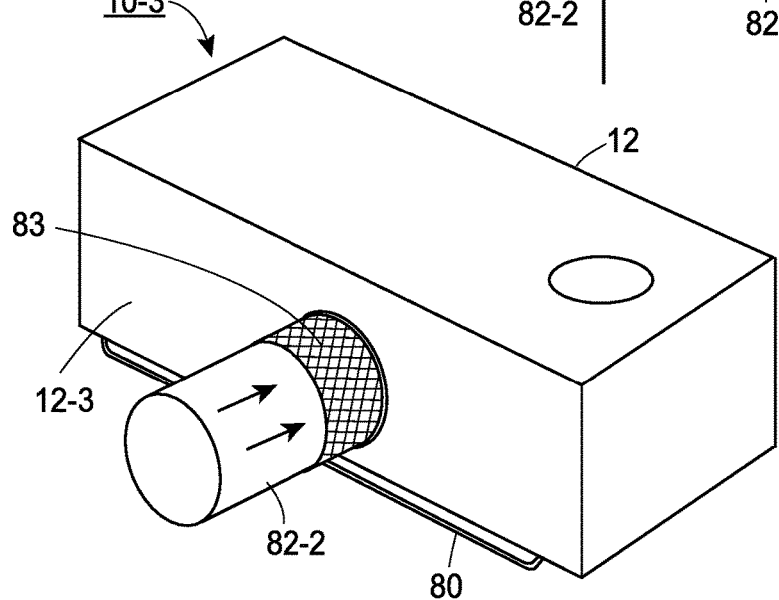
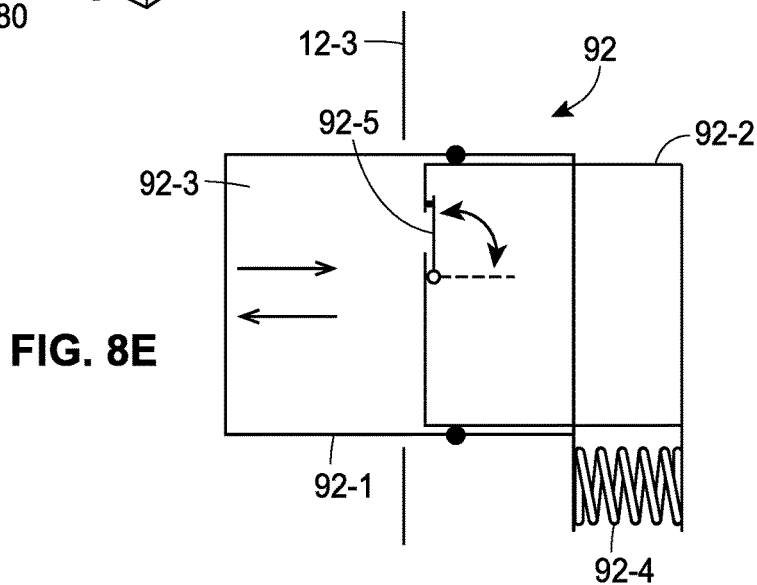

DRUG DELIVERY DEVICE WITH VACUUM ASSISTED SECUREMENT AND/OR FEEDBACK

CROSS-REFERENCE TO RELATED APPLICATIONS

This is the United States national phase of International Patent Application No. PCT/US16/18149, filed Feb. 17, 2016, and claims the benefit of priority to U.S. Provisional Patent Application No. 62/117,420, filed Feb. 17, 2015, and the entire contents of each are expressly incorporated herein by reference.

FIELD OF THE DISCLOSURE

The present disclosure relates to drug delivery devices. More particularly, the present disclosure relates to drug delivery devices having vacuum assisted securement and patient/operator feedback.

BACKGROUND OF THE INVENTION

Some drug delivery devices may be configured to be temporarily attached to a patient to deliver a drug or other substance via an injection needle or some other means, over an extended period of time. The device may be attached to the tissue of the patient's abdomen, thigh, arm or some other portion of the patient's body.

Many of these devices have a rigid housing and may use an adhesive disposed on or over the base of the housing to adhere the device to the patient's body tissue. Many of these adhesives yield higher retention performance over an extended period of time when they are initially applied in a uniform manner with high pressure.

Applying a high uniform pressure across the adhesive, when attaching the device to the patient's body, can be difficult because body tissue is soft and often contoured or curved. Consequently, high performance retention of the device to the body over extended periods of time may not be achieved.

To overcome this difficulty, the soft body tissue may be pinched between the device and the bones or other structures behind the body tissue when attaching the device, to achieve device retention over an extended period of time. Unfortunately, pinching the soft body tissue may be uncomfortable or painful for the patient and may not uniformly apply high pressure across the adhesive.

Another method used to overcome low retention performance is to use a stronger adhesive. This method, however, increases discomfort or pain when the device is removed from the patient.

Accordingly, a drug delivery device with improved retention performance over extended periods of time and/or which allows the use of less aggressive adhesives to reduce discomfort or pain upon device removal, is desired.

SUMMARY OF THE INVENTION

Disclosed herein is a drug delivery device. Various embodiments of the drug delivery device may comprise a housing with a rigid base. The rigid base may have a surface defining at least one pressure communication channel or aperture, which distributes a negative fluid pressure across the base that draws body tissue against the base.

In various embodiments, the device may further comprise a porous, adhesive layer disposed over the at least one pressure communication channel or aperture, which adhesively attaches the device to the body tissue. The at least one pressure communication channel or aperture distributes a negative fluid pressure across the adhesive layer, thereby drawing the body tissue uniformly against the entire surface area of the adhesive layer.

In various embodiments, the porous, adhesive layer may be resilient.

In various embodiments, the drug delivery device may comprise a housing, at least one bladder disposed over a base of the housing, and a flexible adhesive layer disposed over the at least one bladder, which adhesively attaches the device to body tissue. The at least one bladder, in a partially inflated or expanded state, conforms to the contour of the body tissue when the device is applied thereto with an application force, the application force thereby being distributed uniformly across the entire surface area of the flexible adhesive layer. Collapsing the at least one bladder against the base, after the device is applied to the body tissue, causes the flexible adhesive layer to pull the body tissue toward the base, thereby stretching the body tissue.

In various embodiments, the at least one pressure communication channel may comprise a spiral-shaped groove having a first end disposed at a central area of the base and a second end which is disposed at a peripheral area of the base.

In various embodiments, the at least one pressure communication channel comprises two or more concentric grooves.

In various embodiments, the rigid base may include a port in fluid communication with the at least one pressure communication channel or aperture, the port for applying the negative pressure to the at least one pressure communication channel or aperture.

In various embodiments, the drug delivery device may further comprise a negative pressure source in fluid communication with the at least one pressure communication channel.

In various embodiments, the negative pressure source may be separate from the device.

In various embodiments, the negative pressure source may be integrated with the device.

In various embodiments, the negative pressure source may comprise a vacuum pump.

In various embodiments, the negative pressure supplied by the vacuum pump may be selected by changing one or more of a speed of the vacuum pump, a stroke length of the vacuum pump, and power to the vacuum pump.

In various embodiments, the drug delivery device may further comprise a valve for adjusting the negative fluid pressure generated by the vacuum pump.

In various embodiments, the valve may have a negative differential pressure setting that can be selected by varying at least one of a pre-compression of a valve biasing element and a valve area that negative fluid pressure is communicated across.

In various embodiments, the drug delivery device may further comprise a controller, wherein the valve may have a negative differential pressure setting that can be selected by the controller.

In various embodiments, the drug delivery device may further comprise at least two fixed-pressure valves connected between the vacuum pump and the at least one pressure communication channel or aperture, wherein the negative fluid pressure supplied by the active pump may be selected by including or excluding one or more of the fixed-pressure valves which alter a flow path of the negative fluid pressure between the active pump and the at least one pressure communication channel or aperture.

In various embodiments, the drug delivery device may further comprise one or more controller actuated valves connected with the one or more fixed-pressure valves, the one or more controller actuated valves may be operative for including or excluding the one or more fixed pressure valves.

In various embodiments, the drug delivery device may further comprise a user-selectable negative fluid pressure selector, which allows a user to select the negative fluid pressure supplied by the vacuum pump.

In various embodiments, the negative pressure source may comprise an oxygen absorber.

In various embodiments, the negative pressure source may comprise a syringe.

In various embodiments, the negative pressure source may comprise an air chamber that expands in volume from a minimum volume state to generate the negative pressure.

In various embodiments, the air chamber may comprise a biasing element for expanding the air chamber from the minimum volume state.

In various embodiments, the air chamber may comprise a flexible air chamber that expands and collapses.

In various embodiments, the drug delivery device may further comprise a user actuated first lever connected to the housing, the first lever for collapsing the air chamber.

In various embodiments, the first lever may compress the biasing element when the user moves the first lever in a first direction.

In various embodiments, the drug delivery device may further comprise a plunger and a cylinder, the plunger and cylinder movably disposed relative to one another. In some embodiments, the air chamber may be formed between the plunger and the cylinder.

In various embodiments, one of the plunger and the cylinder may be movable by the user for collapsing the air chamber.

In various embodiments, one of the plunger and the cylinder may compress the biasing element when pressed by the user.

In various embodiments, the air chamber may include a valve or vent that allows air contained within the air chamber to pass therethrough when the air chamber is collapsed to the minimum volume state and which does not allow air to pass therethrough when the chamber is expanded from the minimum volume state.

In various embodiments, the drug delivery device may further comprise a removable sealing film disposed over the adhesive layer for maintaining the adhesive layer in a sterile condition prior to use of the device. In some embodiments air exhausted from the air chamber when the air chamber is collapsed to the minimum volume state may break a seal between the sealing film and the adhesive layer to facilitate removal of the sealing film.

In various embodiments, activation of the device by the user may release the first lever from the air chamber to allow the biasing element to decompress and expand the air chamber thereby generating the negative pressure in the at least one channel or aperture.

In various embodiments, the movement of the first lever in the first direction may activate the device, the activation of the device thereby causing the first lever to be released from the air chamber to allow the biasing element to decompress and expand the air chamber, thereby generating the negative pressure in the at least one channel or aperture.

In various embodiments, the drug delivery device may further comprise a second lever which facilitates movement of the first lever in the first direction by the user pinching the first and second levers together.

In various embodiments, one of the plunger and the cylinder may allow the biasing element to decompress and expand the air chamber thereby generating the negative pressure in the at least one channel or aperture.

In various embodiments, releasing one of the plunger and the cylinder may expand the air chamber thereby generating the negative pressure in the at least one channel or aperture.

In various embodiments, the drug delivery device may further comprise a controller for controlling the amount of the negative pressure.

In various embodiments, the drug delivery device may further comprise a ballast volume between the plunger and a desired point of negative pressure application.

In various embodiments, the drug delivery device may further comprise a fluid pressure distribution structure for distributing fluid pressure to the at least one pressure communication channel or aperture.

In various embodiments, the fluid pressure distribution structure may comprise a serial structure.

In various embodiments, the serial structure may comprise a primary fluid pressure delivery conduit and two or more secondary fluid pressure delivery conduits extending from the primary fluid pressure deliver conduit.

In various embodiments, the primary fluid pressure delivery conduit may becoupled to a source of fluid pressure.

In various embodiments, the fluid pressure distribution structure may comprise a parallel structure.

In various embodiments, the parallel structure may comprise a plurality of fluid pressure delivery conduits extending from a source of fluid pressure.

In various embodiments, the drug delivery device may further comprise one or more valves disposed in the fluid pressure distribution structure.

In various embodiments, the valves may sequentially open to sequentially distribute the fluid pressure to the at least one pressure communication channel or aperture.

In various embodiments, the secondary fluid pressure conduits may be operative as pressure regulators.

In various embodiments, the secondary fluid pressure conduits may operate as pressure regulator by collapsing at a predetermined negative fluid pressure.

In various embodiments, the valves may have a higher opening negative fluid pressure than the predetermined negative fluid pressure at which the secondary fluid pressure conduits collapse at.

In various embodiments, the one or more valves may open at a predetermined negative fluid pressure.

In various embodiments, the predetermined negative fluid pressure may be higher than a negative fluid pressure applied to the body tissue.

In various embodiments, the drug delivery device may further comprise a sealing ring disposed around an injection needle entry site.

In various embodiments, the drug delivery device may further comprise a sealing ring partially embedded in or disposed on, the adhesive layer and surrounding an opening through which an injection needle of the device can extend through during needle insertion.

In various embodiments, the drug delivery device may further comprise a sealing ring partially embedded in or disposed on, the base of the housing and surrounding an opening through which an injection needle of the device can extend through during needle insertion.

In various embodiments, the drug delivery device may further comprise an injection apparatus including a container for a pharmaceutical product or drug.

In various embodiments, the pharmaceutical product or drug may be selected from the group consisting of TNF inhibitors, antibodies to the calcitonin gene-related peptide receptor, colony stimulating factors, erythropoiesis stimulating agents, apelin receptor agonists, anti-thymic stromal lymphopoietin antibodies, anti-thymic stromal lymphopoietinreceptor antibodies, antibodies that bind human Proprotein Convertase Subtilisin/Kexin Type 9 and tissue inhibitors of metalloproteinases.

In various embodiments, the drug delivery device may further comprise a pressure sensor for sensing the proximity of the body tissue to the device.

In various embodiments, the drug delivery device may further comprise a pressure sensor for sensing whether there is negative fluid pressure drawing the body tissue against the adhesive layer.

In various embodiments, the drug delivery device may further comprise a pressure sensor for sensing whether there is negative fluid pressure drawing the body tissue against the base.

In various embodiments, the pressure sensor senses the negative fluid pressure if the device is properly secured to the body tissue and wherein the pressure sensor does not sense or senses very little negative fluid pressure if the device is improperly secured to the body tissue.

In various embodiments, the pressure sensor outputs a signal which is used by the controller to determine if the device is properly secured to the body tissue of the patient.

In various embodiments, the pressure sensor may comprise an absolute pressure sensor or a differential pressure sensor.

In various embodiments, the pressure sensor may comprise a bellows.

In various embodiments, the bellows compresses when the pressure sensor senses the negative fluid pressure.

In various embodiments, the bellows expands when it senses positive fluid pressure.

In various embodiments, the bellows may include one or more contacts and further comprising a circuit which is closed by the one or more contacts of the bellows if the bellows senses a predetermined positive fluid pressure threshold.

In various embodiments, the drug delivery device may further comprise an element for biasing the bellows in compression and expansion.

In various embodiments, the pressure sensor may be integrated with the plunger and cylinder.

In various embodiments, the pressure sensor may comprise a strain sensor affixed to a predictably flexible surface subject to negative pressure.

In various embodiments, the pressure sensor monitors relative movement between the plunger and the cylinder after the air chamber has been collapsed by depressing one of the plunger and the cylinder.

In various embodiments, the pressure sensor, upon the release of one of the plunger and cylinder, senses a negative pressure if one of the plunger and the cylinder moves and then stops prior to the air chamber returning to a fully expanded state.

In various embodiments, the pressure sensor, upon the release of one of the plunger and cylinder, senses little or no negative pressure if one of the plunger and the cylinder moves to the fully expand the air chamber.

In various embodiments, the pressure sensor may comprise an optical source for generating and an optical signal and an optical receiver for receiving the optical signal.

In various embodiments, the optical receiver does not receive the optical signal generated by the optical source if the device is properly secured to the body tissue and wherein the optical receiver does receive the optical signal generated by the optical source if the device is improperly secured to the body tissue.

In various embodiments, the optical receiver does not receive the optical signal generated by the optical source if negative pressure is generated in the air chamber after the release of one of the plunger and the cylinder and wherein the optical receiver does receive the optical signal generated by the optical source if little or no negative pressure is generated in the air chamber upon the release of one of the plunger and cylinder.

Further disclosed herein is a drug delivery device comprising a housing including a rigid base, the base including a surface having a first pressure communication aperture; an adhesive layer disposed over or on the base, the adhesive layer for adhesively attaching the device to body tissue, the adhesive layer having a second pressure communication aperture aligned with first pressure communication aperture, the apertures exposing a portion of the body tissue; and a pressure sensor for determining whether the device is properly attached to the body tissue by the adhesive layer.

In various embodiments, the pressure sensor may comprise a bellows or a diaphragm.

In various embodiments, the bellows or diaphragm may be expanded to sense whether a negative fluid pressure can be generated between the exposed body tissue and the bellows or the diaphragm.

In various embodiments, the pressure sensor may further comprise a rod attached to the bellows or diaphragm and an electrically powered coil for pulling the rod to expand the bellows or the diaphragm when the coil is energized.

In various embodiments, the speed at which the rod is pulled by the energized coil to expand the bellows or diaphragm determines whether a negative pressure is generated between the exposed body tissue and the bellows or the diaphragm.

In various embodiments, a negative pressure is generated between the exposed body tissue and the bellows or the diaphragm if the rod does not move or moves slowly, thereby indicating that the device is properly attached to the body tissue by the adhesive layer.

In various embodiments, very little or no negative pressure is generated between the exposed body tissue and the bellows or the diaphragm if the rod moves or moves quickly, thereby indicating that the device is improperly attached to the body tissue by the adhesive layer.

In various embodiments, the speed of the rod may be monitored by monitoring the shape of a current through the coil over time.

In various embodiments, the circuit may further comprise an electrical circuit, the circuit including a contact, wherein the rod engages the contact to close the circuit if current applied to the coil creates a magnetic field that is sufficient to move the rod if very little or no negative fluid pressure is generated between the exposed body tissue and the bellows or diaphragm.

In various embodiments, the pressure sensor may further comprise a cable attached to the bellows or diaphragm and an electrically powered motor for pulling and winding the cable to expand the bellows or the diaphragm when the motor is energized.

In various embodiments, the energized motor generates torque to pull and wind the cable to expand the bellows or the diaphragm, wherein the amount of torque required to pull and wind the cable to expand the bellows or diaphragm determines whether a negative pressure is generated between the exposed body tissue and the bellows or diaphragm, and wherein the amount of torque generated by the motor is proportional to the amount of current drawn by the motor.

In various embodiments, a negative pressure may be generated between the exposed body tissue and the bellows or the diaphragm if the motor draws current above a predetermined threshold pulling and winding the cable, thereby indicating that the device is properly attached to the body tissue by the adhesive layer.

In various embodiments, very little or no negative pressure may be generated between the exposed body tissue and the bellows or the diaphragm if the motor draws current below a predetermined threshold pulling and winding the cable, thereby indicating that the device is improperly attached to the body tissue by the adhesive layer.

In various embodiments, the drug delivery device may further comprise a source of a positive fluid pressure, wherein the at least one pressure communication channel or aperture is further operative for distributing the positive fluid pressure across the adhesive layer at the end of injection to indicate dose delivery completion.

In various embodiments, the drug delivery device may further comprise a source of a positive fluid pressure for applying the positive fluid pressure between the device and the body tissue at the end of injection to indicate dose delivery completion.

In various embodiments, the drug delivery device may further comprise a source of a positive fluid pressure, wherein the at least one pressure communication channel or aperture is further operative for distributing the positive fluid pressure across the base at the end of injection to indicate dose delivery completion.

Further disclosed herein is a method for attaching a drug delivery device to a patient. In various embodiments the method may comprise placing the device above body tissue of the patient at a selected drug delivery site; applying a negative fluid pressure to at least one pressure communication channel or aperture provided in a base of a housing of the device, the at least one pressure communication channel or aperture distributing the negative fluid pressure across an adhesive layer disposed over the at least one pressure communication channel or aperture, thereby drawing the body tissue uniformly against the entire surface area of the adhesive layer.

In various embodiments the method may comprise placing the device on body tissue of the patient at a selected drug delivery site with an application force, the device having housing with a base, at least one bladder disposed over the base, and a flexible adhesive layer disposed over the at least one bladder, the at least one bladder being in a partially inflated state to conform to the contour of the body tissue, so that the application force is distributed uniformly across the entire surface area of the flexible adhesive layer; and collapsing the at least one bladder against the base to cause the flexible adhesive layer to pull the body tissue toward the base, thereby stretching the body tissue.

In various embodiments the method may comprise placing the device above body tissue of the patient at a selected drug delivery site; applying a negative fluid pressure to at least one pressure communication channel or aperture defined in a base of a housing of the device, the at least one pressure communication channel or aperture distributing the negative fluid pressure across the base; and drawing the body tissue of the patient against the base with the negative pressure.

In various embodiments, the method may further comprise applying a positive fluid pressure to the at least one pressure communication channel or aperture defined in the base of the housing of the device, the at least one pressure communication channel or aperture distributing the positive fluid pressure across the adhesive layer at the end of injection to indicate dose delivery completion.

In various embodiments, the method may further comprise applying a positive fluid pressure between the device and the body tissue at the end of injection to indicate dose delivery completion.

In various embodiments, the method may further comprise applying a positive fluid pressure to the at least one pressure communication channel or aperture defined in the base of the housing of the device, the at least one pressure communication channel or aperture distributing the positive fluid pressure across the base at the end of injection to indicate dose delivery completion.

BRIEF DESCRIPTION OF THE DRAWINGS

FIG. 5B is a table which shows the fluid pressure in pounds per square inch absolute (psia) at various points within the sequential valve arrangement and serial fluid pressure distribution structure embodied in FIG. 5B at different transitions of the valves and branch lines, according to an embodiment of the disclosure.

FIGS. 8B and 8C depict the operation of the plunger pump of FIG. 8A.

FIG. 8D is a perspective view of the device showing a plunger of the plunger pump.

FIG. 8E is a cross-sectional view of a plunger pump fluid pressure source according to another embodiment of the disclosure.

The same reference numerals are used in the drawings to identify the same or similar elements and structures in the various embodiments.

DETAILED DESCRIPTION

The drug delivery device in various embodiments may comprise a disposable single use or reusable on-body injector or autoinjector, which automatically delivers a subcutaneous injection of a fixed or patient/operator-settable dose of a drug over a controlled or selected period of time. The drug delivery device is intended for self-administration by the patient, but can also be used by a caregiver or a formally trained healthcare provider (operator) to administer an injection.

In some embodiments, the drug delivery device may include an adhesive system for temporarily attaching the drug delivery device to body tissue (e.g., skin, organ, and muscle) of the patient, and a pneumatic system which generates a negative fluid pressure (i.e., a vacuum suction force) between the device and the body tissue of the patient, at least when the device is being initially applied to the body tissue with an application force. In some embodiments, the negative fluid pressure may be distributed across the entire surface of the adhesive system by the pneumatic system, thereby drawing the body tissue against the entire surface area of the adhesive system. This in turn, allows the application force to be uniformly applied across the entire surface area of the adhesive system, which improves its retention performance, particularly when the device is attached to contoured and/or soft body tissue. The use of the negative fluid pressure or vacuum suction force may be more comfortable for the patient, particularly when applied to soft body tissue, than pinching the tissue between the device and bones or other structures behind the body tissue. The pneumatic system may also allow a less aggressive adhesive system to be used, which reduces discomfort or pain upon device removal by sufficiently improving the performance of the less aggressive adhesive system, to enable short-term wearing of the device (e.g., a 10 minute application of the device). Further, there is a "wet-out" time where the retention performance of the adhesive system improves as the adhesive flows and covers the body tissue of the patient. The pneumatic system can provide additional retention force until the adhesive system has flowed and covered the body tissue and is fully performing. In other embodiments, the drug delivery device may include a pneumatic system which is configured to operate alone without the adhesive system to temporarily attach the device to the body tissue of the patient. In such embodiments, the patient feels no discomfort or pain when the device is removed from the patient's body because the adhesive system has been eliminated.

Figure 1:
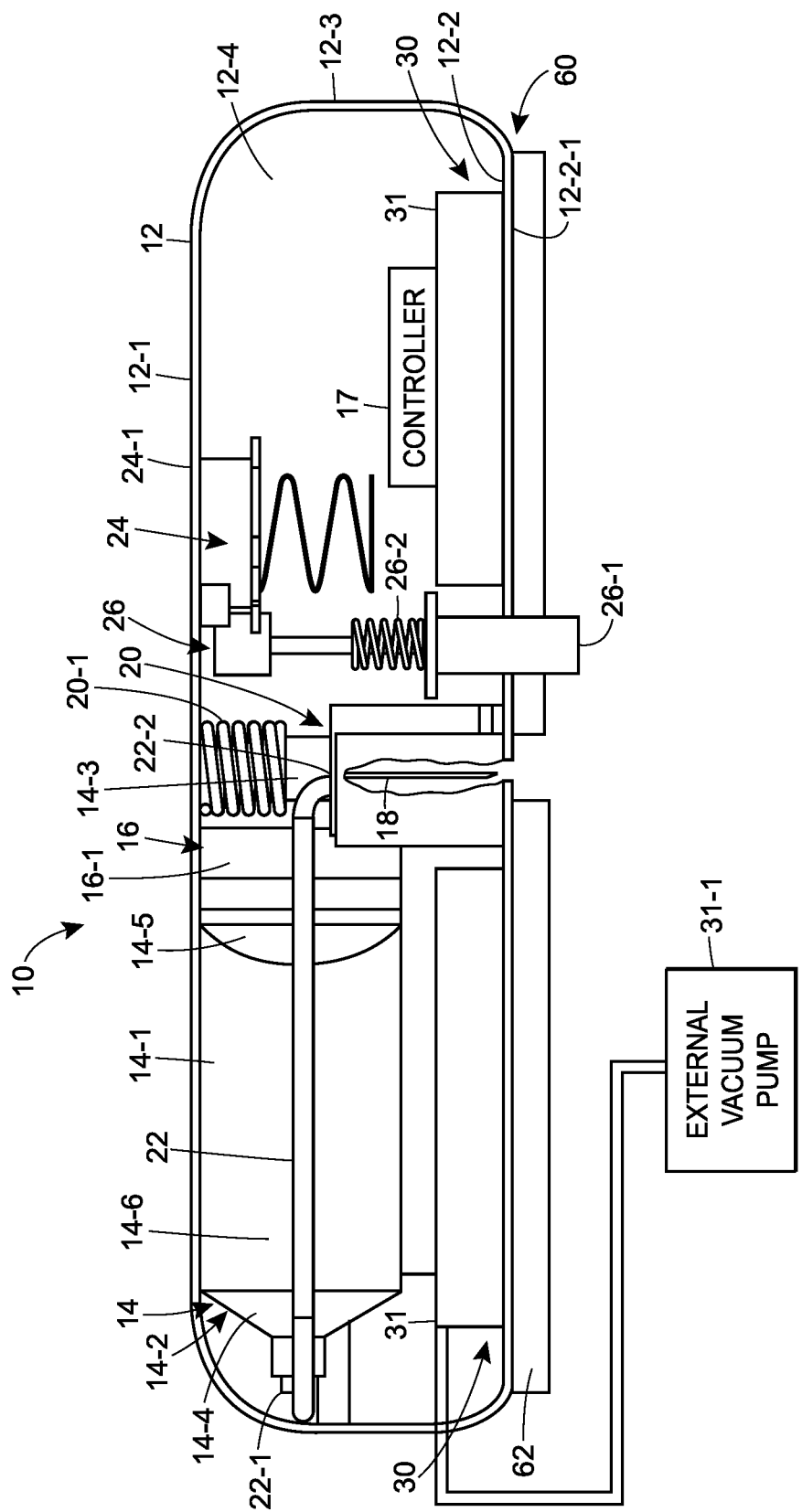
FIG. 1 is an elevational view of a drug delivery device according to an embodiment of the disclosure, with certain elements of the device shown in cross-section or cut-away to reveal other elements.

FIG. 1 shows an embodiment of the drug delivery device 10 according to the present disclosure. The drug delivery device 10 comprises a housing 12, a primary container 14 for a drug or medicament, a plunger drive mechanism 16, an injection needle 18, a needle drive mechanism 20, a device activation mechanism 24, a body proximity sensor 26, a pneumatic system 30, and an optional adhesive system 60.

In various embodiments, the housing 12 may comprise a top wall 12-1, a base or bottom wall 12-2, and one or more side walls 12-3 connecting the top and bottom walls 12-1, 12-2. The housing 12 can be a single, unitary component or multiple components or sections that are combined into a single, unit. One or more of the top, bottom, and side walls 12-1, 12-2, 12-3 of the housing 12 may be constructed from a rigid or substantially rigid material including, but not limited to plastic and/or metal. The housing 12 may be sized to encase the primary container 14, the plunger drive mechanism 16, the injection needle 18, the needle drive mechanism 20, the device activation mechanism 24, the body proximity sensor 26, and one or more components of the pneumatic system 30. If provided, the adhesive system 60 may be disposed on or over an outer surface 12-2-1 of the bottom wall 12-2 of the housing 12. The housing 12 of reusable embodiments of the device 10 may be configured to allow removal and insertion of the primary container 14. For example, in some embodiments, the housing 12 may have a closure (not shown) that allows insertion and removal of the primary container 14. In other embodiments, the housing 12 may be configured so that the bottom wall 12-2 can be removed from the rest of the housing 12 to allow insertion and removal of the primary container 14. In other embodiments, the housing 12 may be configured to receive or attach the primary container 14 or a cartridge module or a cassette containing the primary container 14.

In various embodiments, the primary container 14 may comprise a cylindrical barrel 14-1 having a first end 14-2 and a second end 14-3 disposed opposite the first end 14-2. The second end 14-3 of the barrel 14-1 may define an opening (not visible) and the first end 14-2 of the barrel member 14-1 may be occluded by an end wall 14-4. The end wall 14-4 may include an opening (not visible) for dispensing the drug or medicament stored within the primary container 14. The opening may be closed by a pierceable diaphragm or seal (not shown). A stopper 14-5 may be slidably disposed within the barrel member 14-1 for expelling the drug or medicament from the container barrel member 14-1. In some embodiments, the primary container 14 may be pre-filled with a drug or medicament.

The primary container 14 may be coupled to the injection needle 18 by a tube 22 that may have a first end 22-1 connected to the end wall 14-4 of the primary container 14 and a second end 22-2 connected to or in fluid communication with a proximal end or other portion of the injection needle 18. In various embodiments, the first end 22-1 of the tube 22 may include a piercing mechanism for piercing the seal (if provided) closing the opening in the end wall 14-4 of the primary container 14 to allow fluid communication between an interior 14-6 of the primary container 14 and the tube 22.

In various embodiments, the needle drive mechanism 20 may be configured to move the injection needle 18 between first (concealed/withdrawn) and second (insertion) positions. In the first position, the injection needle 18 may be disposed entirely within the interior 12-4 of the housing 12 and concealed from view as shown in FIG. 1. In the second position, at least a portion of the injection needle 18 may extend out through an opening in the bottom wall 12-2 of the housing 12 to penetrate the body tissue of the patient as shown for example, in FIG. 4C. Some embodiments of the needle drive mechanism 20 may include one or more biasing elements 20-1 for driving the injection needle 18 from the first position to the second position to insert the needle 18 into the patient's body tissue at the injection site and, in some embodiments, for withdrawing the needle 18 from the patient's body tissue (i.e., return the injection needled 18 to the first position) after the plunger drive mechanism 16 completes the drug delivery process. In some embodiments, one or more of the biasing elements 20-1 can include a spring or other element capable of driving and, in some embodiments, withdrawing the needle 18.

In various embodiments, the plunger drive mechanism 16 may comprise a plunger 16-1 and plunger drive (not shown) for driving the plunger 16-1 through the primary container 14 to expel the drug or medicament therefrom. The plunger drive may comprise a mechanical arrangement of one or more biasing elements such as springs, an electrical/mechanical arrangement comprising one or more motors and/or solenoids and a drive train or transmission, and/or a compressed or liquefied gas, and any combination thereof.

In some embodiments, the plunger drive mechanism 16 expels the drug or medicament from the primary container 14 and through the injection needle 18 into the body tissue of the patient after the needle drive mechanism 20 inserts the injection needle 18 into body tissue of the patient. As described earlier, upon completion of drug delivery, the needle drive mechanism 20 may withdraw the injection needle 18 from the body tissue and return it to the first position. In other embodiments, a needle safety guard may deploy around the extended injection needle 18 upon device removal to prevent inadvertent contact therewith. In some embodiments, the needle 18 can include a conventional rigid injection needle. In other embodiments, the needle 18 may comprise a soft cannula made, for example, of Teflon or PE, that is introduced with a sharp internal trocar that retracts immediately after insertion, thereby eliminating the need for retraction or protection of the needle 18.

In some embodiments, a patient, operator, and/or manufacturer programmable controller 17 may be provided to control the operation of the plunger drive mechanism 16. The controller 17, in some embodiments, can comprise a microcontroller. In other embodiments, the controller 17 can comprise a microprocessor and a memory for storing instructions which are executed by the microprocessor to control the plunger drive mechanism 16. In some embodiments, the controller 17 may be programmed to control the speed of the plunger mechanism to allow constant or variable drug delivery rates and/or to control the stroke of the plunger mechanism to deliver a desired dose of the medicament or drug. In some embodiments, the controller 17 may be programmed to control needle insertion and withdrawal speeds and/or needle motion.

In various embodiments, the device activation mechanism 24 may comprise a button 24-1 or other user interface mechanism, which allows the patient or operator to initiate, trigger, or otherwise activate the device 10 after it has been properly attached to the body tissue of the patient. The device activation mechanism 24 may be disposed in the top or side walls 12-1, 12-3 of the housing 12. In some embodiments, the activation mechanism 24 may operate in combination with the controller 17 to sequentially trigger or cause the activation and/or deactivation of one or more of the pneumatic system 30, the needle drive mechanism 20, and the plunger drive mechanism 16. For example, in some embodiments, an input at the button 24-1 or other user interface may activate the pneumatic system 30 to attach or assist in the attachment of the device 10 to the body tissue of the patient. Once the device 10 is attached, the needle drive mechanism 20 may be activated to insert the injection needle 18 into the body tissue. After needle insertion, the plunger drive mechanism 16 may be activated to deliver the drug or medicament into the body tissue. Upon completion of drug delivery, the needle drive 20 may be activated to withdraw the injection needle 18 from the body tissue. In some embodiments, the pneumatic system 30 may be deactivated to allow the device 10 to be removed from the patient's body tissue.

In other embodiments, the activation mechanism 24 may operate alone without the controller 17 to sequentially activate one or more of the pneumatic system 30, the needle drive 20, and the plunger drive mechanism 16.

In various embodiments, the body proximity sensor 26 may comprise an electromechanical sensor that monitors the device attachment process to prevent activation of the device 10 before it has been properly attached to the body tissue of the patient. In some embodiments, the body proximity sensor 26 may continue to monitor the device 10 to detect detachment thereof from the body tissue of the patient during the drug delivery process.

In some embodiments, the electromechanical type body proximity sensor 26 may include a sensing pin 26-1 or other depressible or deflectable member that extends through an aperture in the bottom wall 12-2 of the housing 12. The sensing pin 26-1 may be biased in the extended position by a biasing element 26-2, which in some embodiments may include without limitation a spring or other elastic element. As the device 10 and the body tissue are brought together during the attachment process, the extended sensing pin 26-1 may be the first part of the device 10 to contact the body tissue. As the distance or gap between the body tissue and the device 10 decreases, the extended sensing pin 26-1 may be pressed into the housing 12 of the device 10 or otherwise deflected. When the device 10 is properly attached and secured to the body tissue, via the pneumatic system 30, the sensing pin 26-1 will have been moved into to a depressed position within the housing 12, thereby allowing the operation of the activation mechanism 24, followed by needle insertion, drug delivery, needle withdrawal (if applicable) and any other device function of the injection process. If the device 10 partially or completely disengages from the body tissue, the biasing element 26-2 pushes and moves the sensing pin 26-1 back to the extended position. In some embodiments, the moment the sensing pin 26-1 moves from the depressed position, the device 10 will terminate the injection process and withdraw the injection needle 18 from the body tissue and into the housing 12. In some embodiments, the body proximity sensor 26 may be capable of communicating sensor information to the controller 17 so that the body proximity sensor 26 may be monitored and/or controlled by the controller 17.

Electromechanical-type body proximity sensors 26 may include, but are not limited to switches and the like, which monitor the movement of the pin or other depressible or deflectable member as it is depressed or deflected during the body sensing process. Depressible and deflectable members can include, but are not limited to compressible pads. Such sensors may use capacitive or resistive methods to detect pad compression. In some embodiments, the body proximity sensor 26 may comprise an electrical sensor including, but not limited to a capacitive sensing device, an infrared proximity or distance sensor, which does not use depressible or deflectable pins or other moveable members. In some embodiments, the body proximity sensor 26 may comprise a mechanical sensor or an optical sensor for sensing contact between the device 10 and the body tissue of the patient.

In various embodiments, the optional adhesive system 60 may comprise an adhesive laminate 62 that is capable of allowing positive and negative fluid pressure to pass therethrough and which can, in some versions, conform to the contour of the patient's body tissue at the injection site, particularly soft body tissue. In some embodiments, the adhesive layer 62 may be a porous sheet layer with a uniform or non-uniform distribution of pores or can include a non-porous sheet layer having one or more openings with a geometrical configuration corresponding to a geometrical configuration of channels and/or apertures in the bottom wall 12-2 of the housing 12 of the drug delivery device, as will be described in more detail below. As discussed earlier, the retention performance of the adhesive system 60 may be assisted by the pneumatic system 30.

In various embodiments, the pneumatic system 30 can comprise a fluid pressure source 31 which generates a negative fluid pressure (vacuum suction or pressure). The fluid pressure source 31, in other embodiments, may be configured to generate positive fluid pressure (e.g., air pressure). In other embodiments, the fluid pressure source 31 of the pneumatic system 30 may be configured to generate negative fluid pressure in a first mode of operation and a positive fluid pressure in a second mode of operation.

Figure 2A:
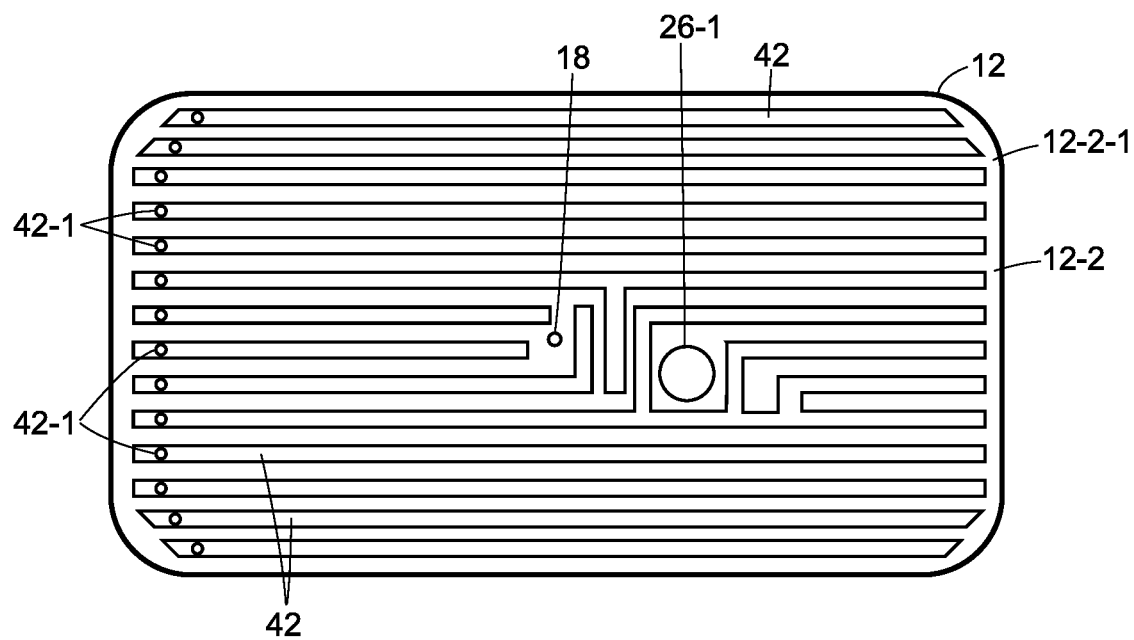
FIGS. 2A-2E are bottom views of the device showing various embodiments of a base wall of a housing of the device of FIG. 1.

As shown in FIG. 2A, the pneumatic system 30 in some embodiments of the device 10 of FIG. 1, may further comprise a fluid pressure distribution arrangement formed by a plurality of channels or grooves 42 (vacuum grooves 2) provided in the outer surface 12-2-1 of the bottom wall 12-2 of the housing 12 (illustrated without the optional adhesive system 60). Each of the vacuum grooves 42 may include at least one vacuum port 42-1 that may extend through the bottom wall 12-2 of the housing 12 and pneumatically communicate with the fluid pressure source 31 of the pneumatic system 30 (FIG. 1), which supplies negative fluid pressure (e.g. device attachment and retainment) or positive fluid pressure (e.g., device removal). The vacuum grooves 42 distribute the fluid pressure force across the outer surface 12-2-1 of the bottom wall 12-2 of the device housing 12. The vacuum grooves 42 may be separated from another as shown in FIG. 2A, connected to one another (not shown) or some of the vacuum grooves 42 may be separated from one another while others are connected to one another (not shown), depending upon the desired distribution of the fluid pressure across the bottom wall 12-2 of the housing 12.

Figure 2B:
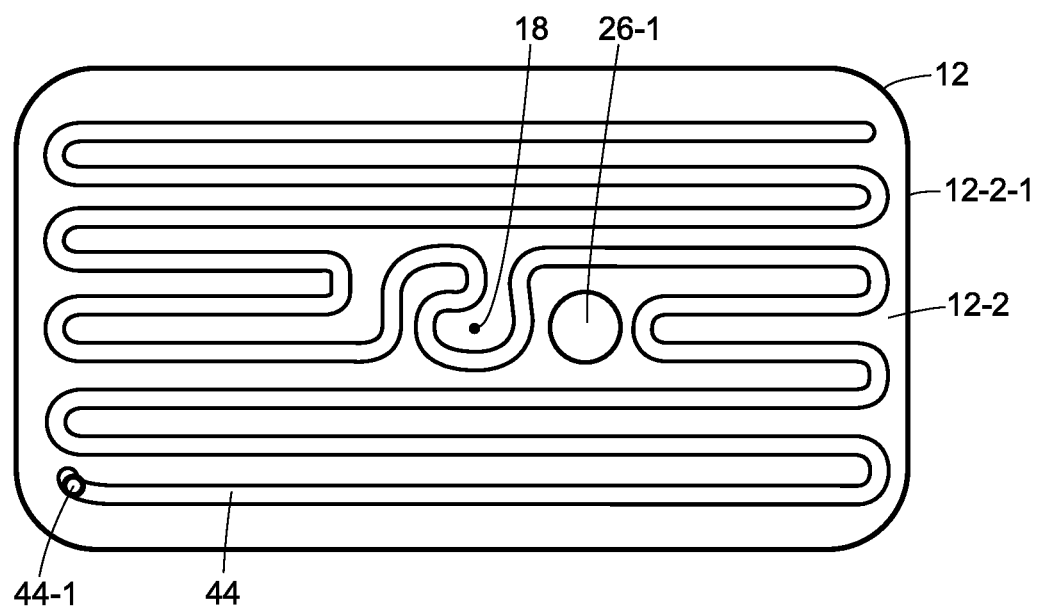

As shown in FIG. 2B, other embodiments of the vacuum distribution arrangement of the pneumatic system 30 may comprise a single continuous vacuum groove 44 formed in the outer surface 12-2-1 of the bottom wall 12-2 of the housing 12 (shown without the optional adhesive system 60). The vacuum groove 44 may include at least one vacuum port 44-1 that may extend through the bottom wall 12-2 of the housing 12 and pneumatically communicate with the fluid pressure source 31 of the pneumatic system 30 (FIG. 1), which supplies negative or positive fluid pressure. As in the previous embodiment of FIG. 2A, the vacuum groove 44 distributes the fluid pressure force across the outer surface 12-2-1 of the bottom wall 12-2 of the device housing 12.

Figure 2C:
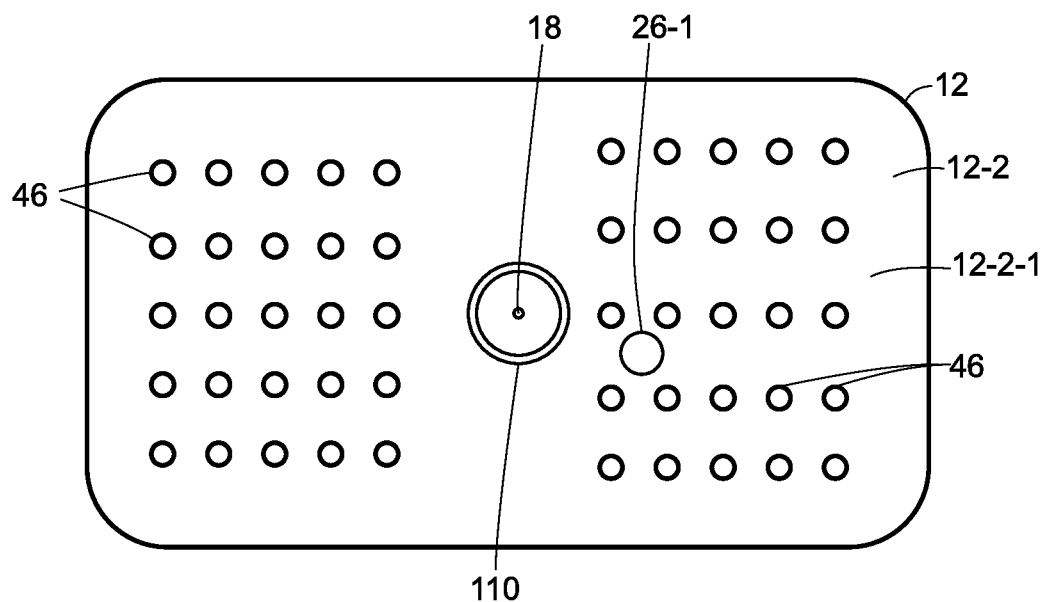

In other embodiments, as shown in FIG. 2C, the vacuum distribution arrangement of the pneumatic system 30 may comprise one or more apertures 46 that extend through the bottom wall 12-2 of the housing 12 (shown without the optional adhesive system 60) and pneumatically communicate with the fluid pressure source 31 of the pneumatic system 30 (FIG. 1), which supplies negative or positive fluid pressure. As in the previous embodiments of FIGS. 2A and 2B, the apertures 46 distribute the fluid pressure across the outer surface 12-2-1 of the bottom wall 12-2 of the device housing 12. It should therefore be appreciated that the configuration and/or arrangement of pressure communication channel(s) and/or aperture(s) in the bottom wall 12-2 of the housing 12 can vary within the scope of the present disclosure and is not limited to those specific examples disclosed herein. Additional embodiments, in fact, will be disclosed below in reference to FIGS. 2D and 2E.

Figure 3A:
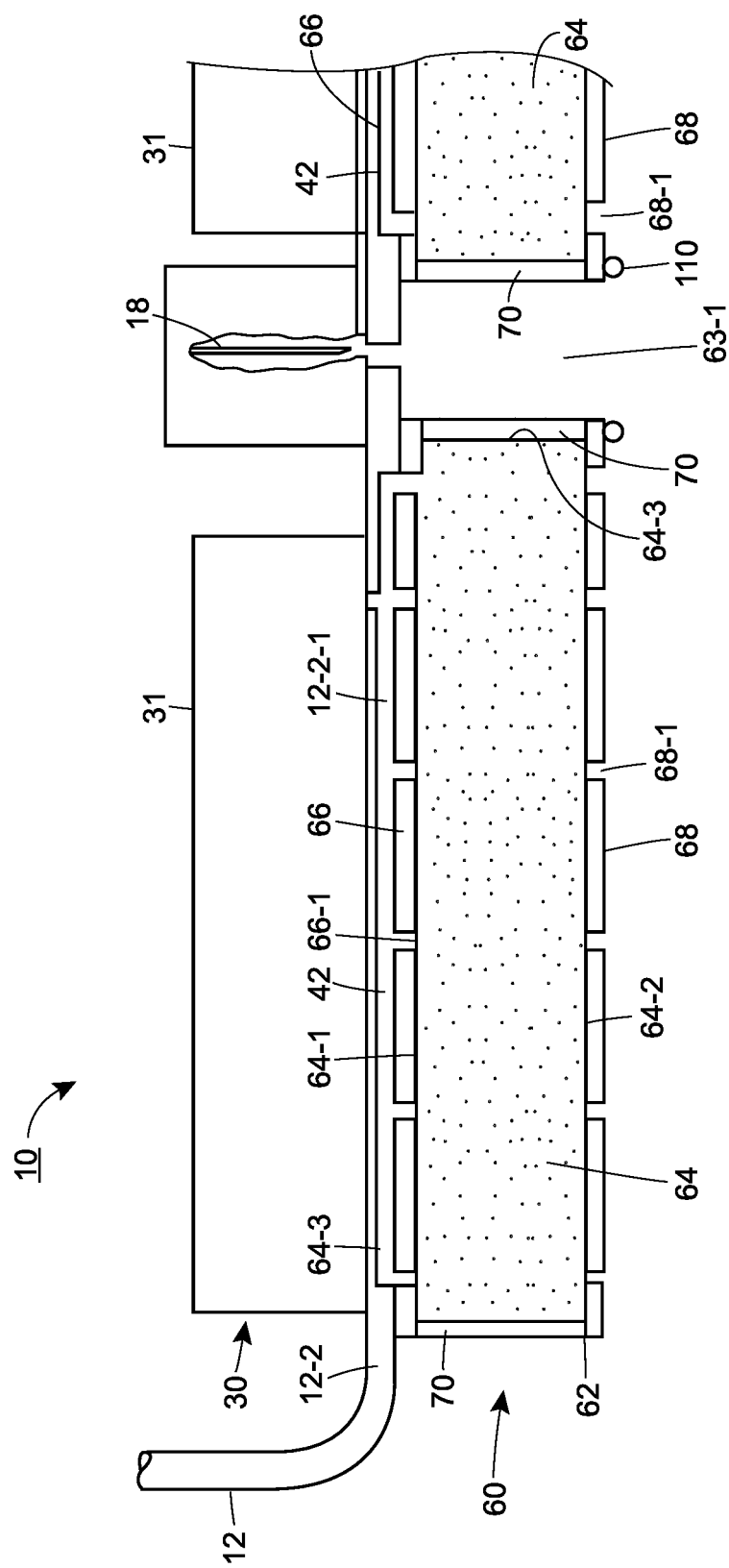
FIG. 3A is an enlarged elevational view of a section of the drug delivery device of FIG. 1, which shows an embodiment of an adhesive laminate of an optional adhesive system, with certain elements of the device shown in cross-section or cut-away to reveal other elements.
Figure 3B:
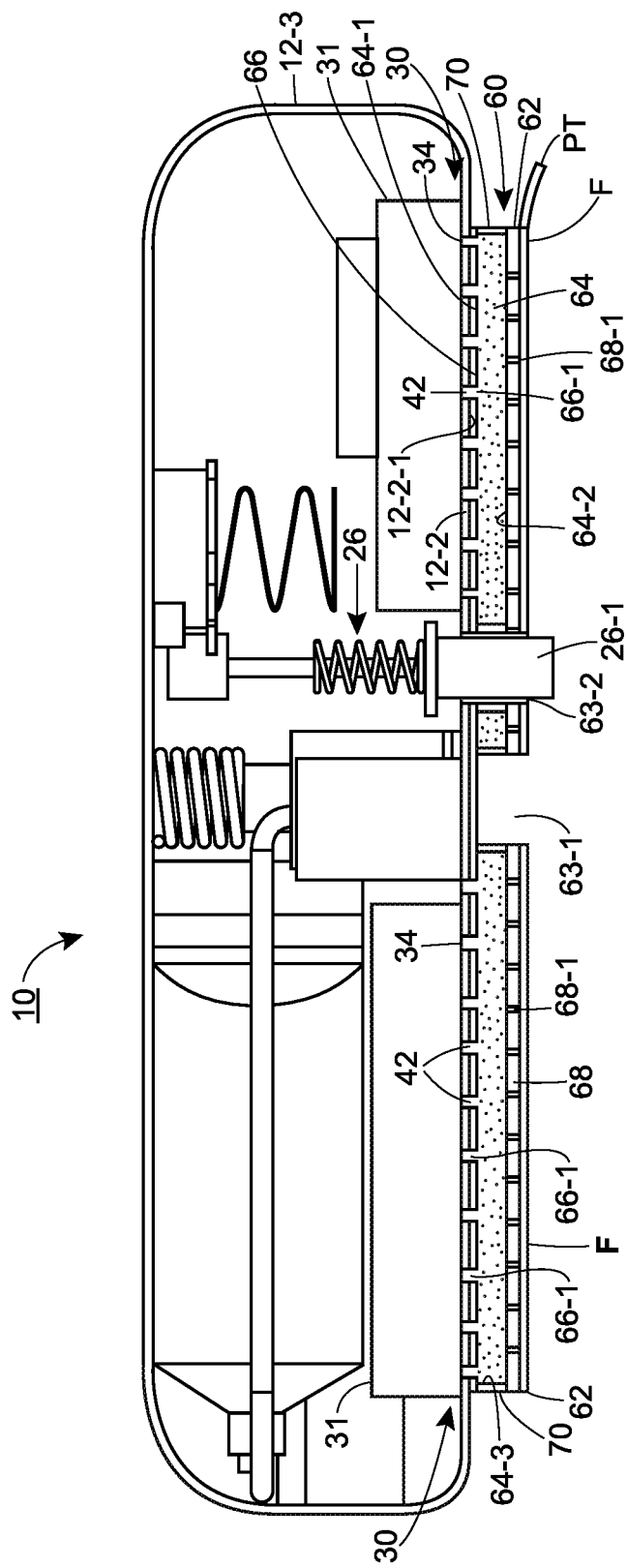
FIG. 3B is an elevational view of the entire drug delivery device shown in FIG. 3A.
Figure 3C:
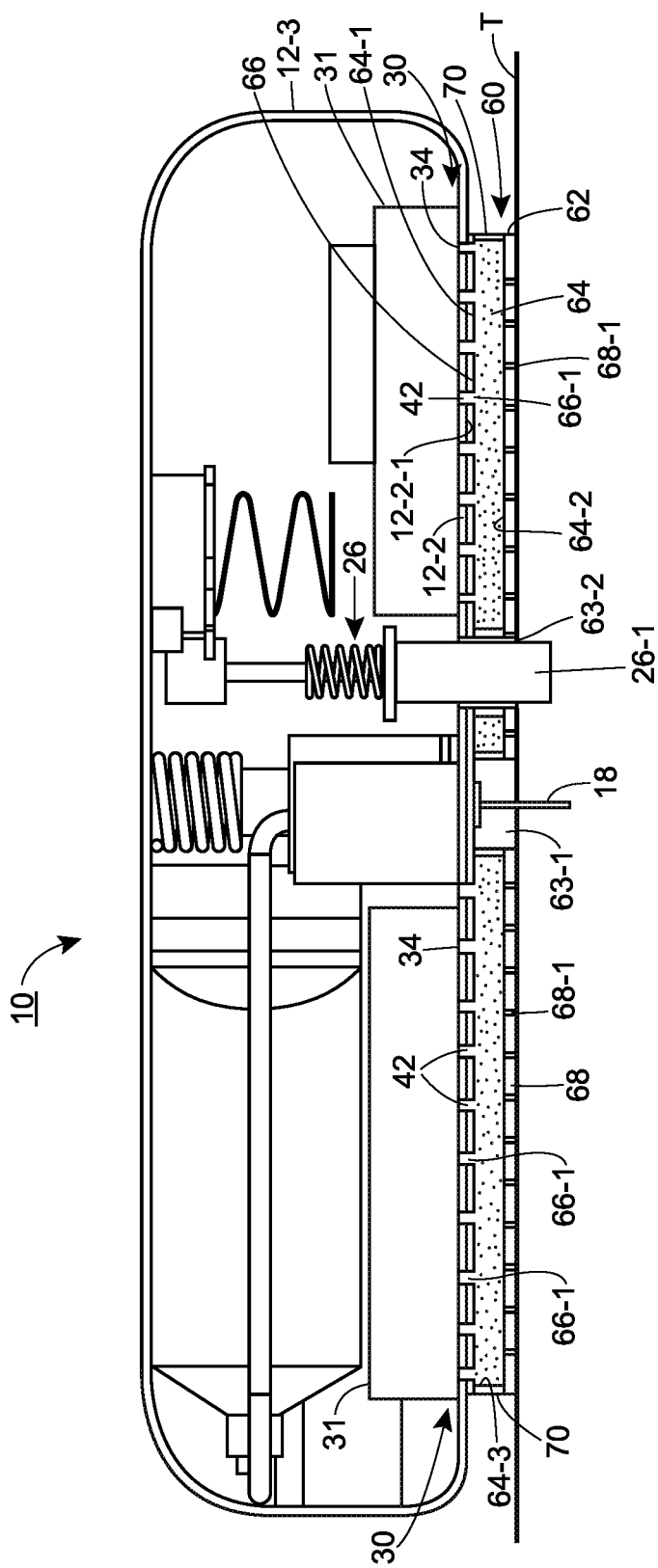
FIG. 3C is an elevational view of the drug delivery device of FIG. 3B attached to body tissue of a patient with the injection needle inserted in the tissue.

Referring now to FIG. 3A, the adhesive laminate 62 of the optionally provided adhesive system 60 may comprise a compressible porous layer 64 having a first face surface 64-1, a second face surface 64-2 and one or more side surfaces 64-3 connecting the first and second face surfaces 64-1, 64-2. The first face surface 64-1 may be covered by or coated with a first adhesive layer 66 that adhesively attaches the laminate 62 to the outer surface 12-2-1 of the bottom wall 12-2 of the device housing 12. The second face surface 64-2 may be covered by or coated with a second adhesive layer 68 that adhesively attaches the device 10 to the tissue T of the patient's body (FIG. 3C). The one or more side surfaces 64-3 may be covered by or coated with a sealing layer 70 that connects the first and second adhesive layers 66, 68 and hermetically seals the side surface(s) 64-3 of the porous layer 64. In other embodiments, the one or more side surfaces 64-3 may be sealed by a process that closes off the pores (e.g., a hot knife cutting process or a thermal reflow process). The first adhesive layer 66 may include one or more openings 66-1 that are aligned with, and dimensioned and configured to match respective ones of the one or more vacuum grooves or apertures 42 defined in or by the bottom wall 12-2 of the device housing 12 (such as the vacuum grooves or apertures shown in FIGS. 2A-2C, as well as 2D and 2E described below) to provide fluid communication with the porous layer 64 to distribute the negative and/or positive fluid pressure, supplied by the fluid pressure source 31 of the pneumatic system 30, across the first surface 64-1 of the porous layer 64 of the laminate 62. In other embodiments, the one or more openings 66-1 may be formed in any other suitable pattern which distributes the negative and/or positive fluid pressure supplied by the fluid pressure source 31, across the first surface 64-1 of the porous layer 64 of the laminate 62. The second adhesive layer 68 may include one or more openings 68-1 disposed across the second surface 64-2 of the porous layer 64. The one or more openings 68-1 allow the negative and/or positive fluid pressure applied across the first surface 64-1 of the porous layer 64 and transmitted through the porous layer 64 to its second surface 64-2, to be applied across the injection site to draw the body tissue T of the patient against the laminate 62 in the case of negative fluid pressure (FIG. 3C) or release the device 10 from the body tissue T of the patient. The one or more openings 68-1 may be aligned with, and dimensioned and configured to match respective ones of the one or more vacuum grooves or apertures 42 defined in or by the bottom wall 12-2 of the device housing 12. In other embodiments, the one or more openings 68-1 may be formed in any other suitable pattern which allows the negative and/or positive fluid pressure to be applied across the body tissue T at the injection site. As shown in FIGS. 3B and 3C, the laminate 62 may also include openings 63-1 and 63-2 for allowing the injection needle 18 and the sensing pin 26-1 of the body proximity sensor 26 to pass therethrough.

The porous layer 64 of the laminate 62 can be constructed from an open cell foam material or any other suitable compressible porous material. Each of the first and second adhesive layers 66 and 68 of the laminate 62 can be a double sided, medical adhesive tape that has the one or more openings 66-1 or 68-1 punched through it. The first and second adhesive layers 66 and 68 can also be made using any other suitable adhesive material which can be formed with openings. A removable sterile liner or barrier film F (FIG. 3B) may be provided, which covers the second adhesive layer 68 of the laminate 62 prior to use of the device 10. The film F may include a pull tab PT to facilitate removal thereof.

The fluid pressure source 31 of the pneumatic system 30 depicted in the device 10 shown in FIGS. 3A-3C, may comprise one or more vacuum storage receptacles, each of which stores a negative fluid pressure. One or more valves 34 may be provided for selectively connecting the vacuum storage receptacles 31 with vacuum ports (not visible) of the one or more vacuum grooves 42 (or to apertures if applicable) defined in or by the bottom wall 12-2 of the device housing 12, for application of the negative fluid pressure or vacuum contained within the storage receptacles 31. The negative fluid pressure stored in each of the vacuum storage receptacles 31 may be generated or supplied by an external vacuum pump or like mechanism (not shown) that can be removably connected to the receptacles 31 during the operation and/or manufacturing of the device 10.

In operation, the pneumatic system 30 of the device 10 generates and distributes the negative fluid pressure across the entire surface area of the laminate 62 of the adhesive system 60, thereby drawing the body tissue T against the entire surface area of the laminate 62. This allows an initial application force to be uniformly applied across the entire surface area of the laminate 62, which allows the rigid housing 12 of the device 10 to be adhered via the adhesive system 60 to soft tissue with curved and/or uneven contours. Accordingly, the retention performance of the adhesive system 60 may be improved and needle insertion challenges associated with non-planar tissue surfaces may be reduced.

Figure 4:
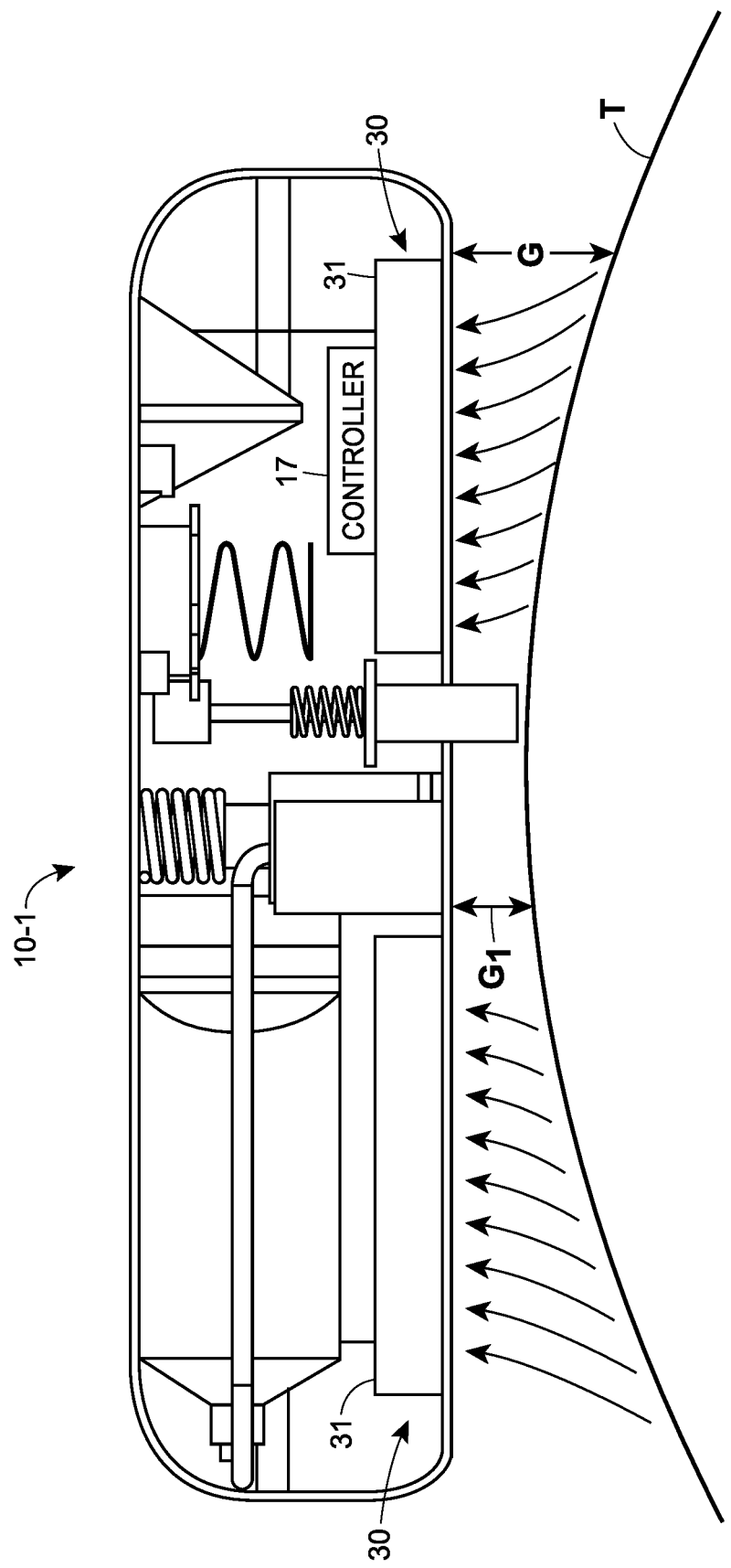
FIG. 4 is an elevational view of an embodiment of the device of FIG. 1 without the adhesive system.

FIG. 4 shows another embodiment of the drug delivery device 10-1. The device 10-1 is similar to the device 10 of FIG. 1 except it does not include the optional adhesive system 60. The negative fluid pressure supplied by the fluid pressure source 31 of the pneumatic system 30 and applied to the bottom of the device 10-1 generates an air-flow or vacuum suction force which draws the body tissue T toward the device 10-1. In accordance with the Bernoulli principle, the greater the gap G between the body tissue T and the bottom of the device 10-1, the greater the air-flow or vacuum suction force requirement will be. The greater air-flow requirement, in turn, will require a larger reserve of negative fluid pressure or vacuum suction force.

Referring to FIGS. 1 and 4, embodiments of the drug delivery device 10, 10-1 used, for example, in laboratory environments can be connected to a large vacuum pump 31-1, which allows the fluid pressure source 31 to be omitted, bypassed, or supplemented. In such embodiments, large reserves of negative fluid pressure are not a problem. In portable embodiments of the device 10, the negative fluid pressure must be supplied by the fluid pressure source 31 of the pneumatic system 30 disposed in the housing 12 of the device 10, 10-1. In some embodiments, the fluid pressure source 31 may comprise a small vacuum pump or a syringe. In other embodiments, the fluid pressure source 31 may comprise one or more oxygen absorbing packets or oxygen absorbers that can be punctured when the pneumatic system is activated. In some embodiments, the oxygen absorbers can be made from iron particles that react with moisture and oxygen to form rust. This process removes oxygen from the environment. One such oxygen absorber is marketed under the brand name Oxy-Sorb. Oxygen makes up approximately 21% of atmospheric content, which may generate up to about −3.0 psi (21%×14.7 psia at sea level) after isolating a volume and then removing the oxygen (at least in its gaseous form). The oxygen absorbers can be disposed within the vacuum distribution arrangement or be disposed remotely from it and connected therewith.

The size of the fluid pressure source 31 generally depends upon the size of the negative fluid pressure that is required to attach and secure the device 10, 10-1 to the body tissue of the patient. If a larger negative fluid pressures is required, a larger and/or more complex fluid pressure source 31 may be required, which undesirably increases the mass, size, and/or cost of the device 10, 10-1. Therefore, it is desirable to minimize the negative fluid pressure requirements of the device 10, 10-1 so that the size of the fluid pressure source 31 of the pneumatic system 30 can be kept to a minimum and therefore, minimize the mass, size, and/or cost of the device 10, 10-1.

Figure 2D:
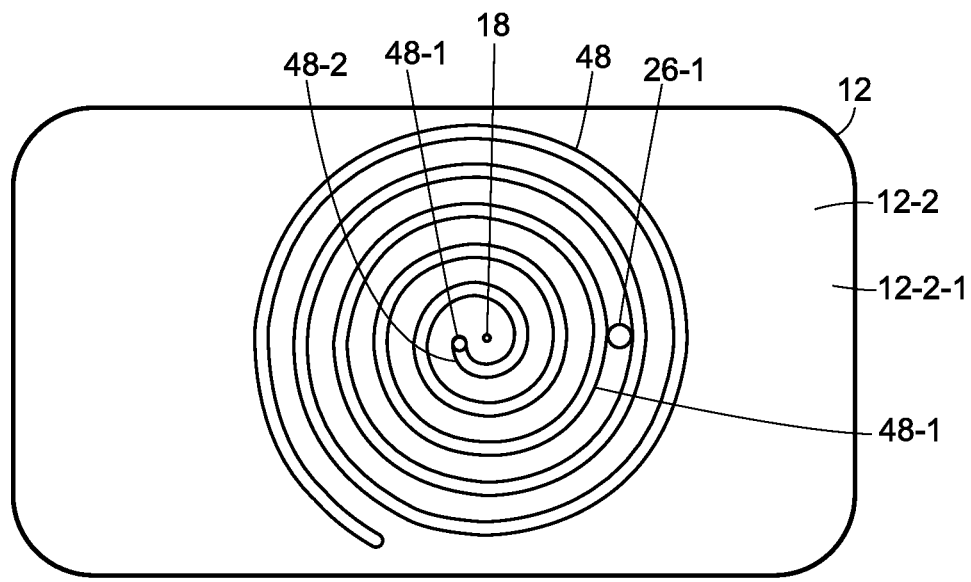

FIG. 2D shows another embodiment of the vacuum distribution arrangement of the pneumatic system 30. This vacuum distribution system minimizes the negative fluid pressure requirements in mobile embodiments of the device 10, 10-1 and comprises a spiral-shaped vacuum groove 48 formed in the outer surface 12-2-1 of the bottom wall 12-2 of the housing 12. The vacuum groove 48 may be configured to spiral around the area of the bottom wall 12-2 where the injection needle 18 will protrude from the housing 12 during needle insertion, as this region of the device should be securely retained against the body tissue of the patient during the operation of the device. The vacuum groove 48 may include at least one vacuum port 26-1 that extends through the bottom wall 12-2 of the housing 12 and pneumatically communicates with the fluid pressure source 31 (FIGS. 1 and 4) of the pneumatic system 30, which supplies negative fluid pressure. As in the previous embodiments of the vacuum distribution arrangement (FIGS. 2A-2C), the spiral-shaped vacuum groove 48 distributes the negative fluid pressure or vacuum suction force across the outer surface 12-2-1 of the bottom wall 12-2 of the device housing 12.

Referring again to FIGS. 1 and 4 and 2D, once the device 10, 10-1 with the vacuum distribution arrangement of FIG. 2D is attached to body tissue of the patient, particularly a convex area of body tissue T (e.g., the thigh or arm), the central-most portion 48-2 of the spiral-shaped groove 48 surrounding the injection needle region of the housing's bottom wall 12-2 should be positioned to contact the tissue first at the injection site, because the spiral-shaped groove 48 concentrates air-flow in the region with the smallest gap $G_1$ (FIG. 4). This rapidly pulls the tissue toward and engages the injection needle region of bottom wall 12 of the device 10, 10-1, thereby sealing the central-most portion of the groove 48. The continued application of negative fluid pressure/vacuum suction force from this point enables a gradual distribution of the negative fluid pressure to an expanding area of the housing's bottom wall 12-2, as the tissue at the injection site is brought into closer proximity, while not applying or expending the negative fluid pressure to the area with the greatest gap G. Since negative fluid pressure is efficiently used, the negative pressure supply requirements of the device 10, 10-1 are minimized. This, in turn, allows for a smaller pneumatic system 30, thus, reducing the mass, size, and/or cost of the device 10, 10-1.

Figure 2E:
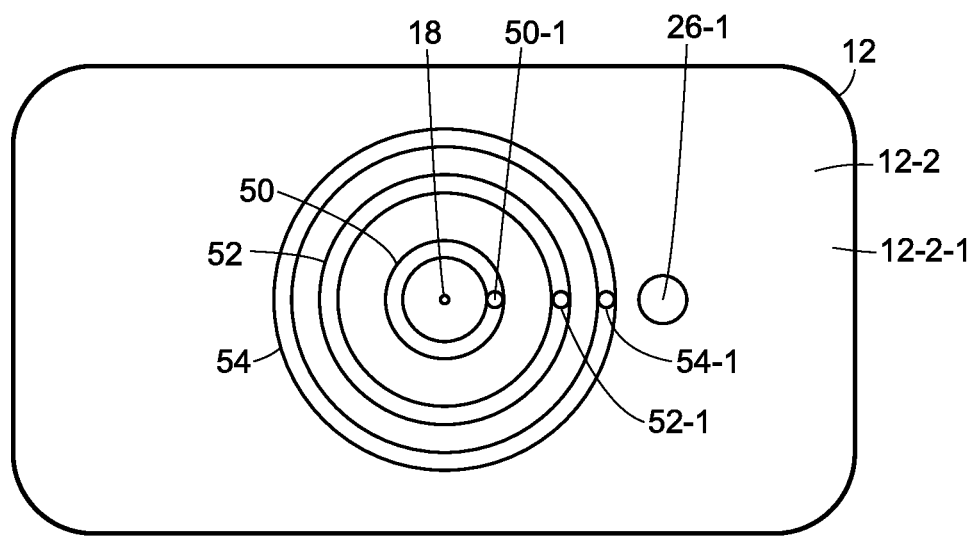

FIG. 2E shows another embodiment of the vacuum distribution arrangement of the pneumatic system 30. In this embodiment, the bottom wall 12-2 of the device housing 12 may comprise a plurality of concentric vacuum grooves 50, 52, 54 formed in the outer surface 12-2-1 thereof (three grooves shown for ease of description and illustration only). Each of the grooves 50, 52, 54 may include at least one vacuum port 50-1, 52-1, 54-1, that extends through the bottom wall 12-2 of the housing 12 and pneumatically communicates with the fluid pressure source 31 of the pneumatic system 30 (FIGS. 1 and 4), which supplies negative fluid pressure. The vacuum grooves 50, 52, 54 may be configured to encircle the area of the bottom wall 12-2 where the injection needle 18 protrudes from the housing 12 during needle insertion to securely retain the device against the patient's body tissues during the operation thereof. As in previous embodiments of FIGS. 2A-2D, the concentric vacuum grooves 50, 52, 54 distribute the negative fluid pressure/vacuum suction force across the outer surface 12-2-1 of the bottom wall 12-2 of the device housing 12.

Referring still to FIG. 2E, the vacuum ports 50-1, 52-1, 54-1 in some embodiments can be sequentially opened starting with vacuum port 50-1 of the smallest diameter groove 50, and then opening the vacuum ports 52-1 and 54-1 of the larger diameter grooves in order of increasing diameter. Additionally, in some embodiments, the width of each of the grooves 50, 52, 54 can progressively decrease moving from the smallest diameter groove 50 to the largest diameter groove 54. Progressively decreasing width of each groove moving from the smallest diameter groove 50 to the largest diameter groove 54 operates to normalize the volumes of the grooves 50, 52, 54 and their corresponding radial air-flow rates, which pull the body tissue toward the bottom wall 12-2 of the device housing 12.

Figure 5A:
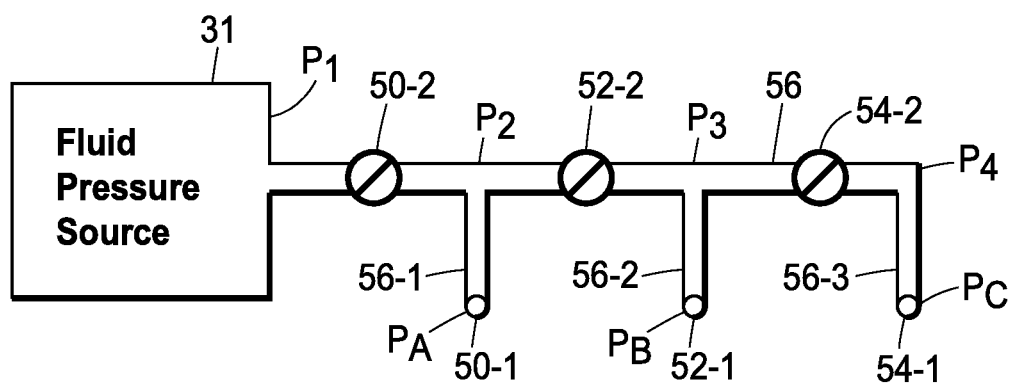
FIG. 5A is a diagram showing an embodiment of a valve arrangement and serial fluid pressure distribution structure that may be used for sequentially opening vacuum ports in the base wall of the device housing.

FIG. 5A shows an embodiment of a sequential valve arrangement, comprising first, second and third valves 50-2, 52-2, and 54-2, respectively, which prioritizes the application of negative fluid pressure to the body tissue of the patient by sequentially opening the vacuum ports 50-1, 52-1, and 54-1 of respective vacuum grooves 50, 52, and 54, shown for example in the embodiment of FIG. 2E. In some embodiments, the operation of the valves 50-2, 52-2, and 54-2 may be controlled by the device controller 17 (FIGS. 1 and 4). In other embodiments, the valves 50-2, 52-2, and 54-2 may comprise check valves including, but not limited to ball check valves, which operate automatically without the need for the controller 17. The valve arrangement may further comprise a serial fluid pressure distribution structure extending between the fluid pressure source 31 and the vacuum ports 50-1, 52-1, and 54-1 of respective vacuum grooves 50, 52, and 54. The serial fluid pressure distribution structure may comprise a vacuum supply line 56 and branch vacuum supply lines (branch lines) 56-1, 56-2, and 56-3. The first valve 50-2 may be disposed in the vacuum supply line 56 before the branch line 56-1, the vacuum port 50-1 of the smallest diameter vacuum groove 50 and the second valve 52-2. The second valve 52-2 may be disposed in the vacuum supply line 56 before the branch line 56-2, the vacuum port 52-1 of the intermediate vacuum groove 52 and the third valve 54-2. The third valve 54-2 may be disposed in the vacuum supply line 56 before the branch line 56-3 and the vacuum port 54-1 of the largest diameter vacuum groove 54. The first valve 50-2 can be configured to open at initial contact between the device 10 and the body of the patient including, but not limited to the threshold travel of the body proximity sensor, or any other similar triggering event. When body tissue is pulled up against the bottom wall 12-2 of the device housing 12, the smallest diameter groove 50 (FIG. 2E), which encircles the region of the housing bottom wall 12-2 where the injection needle 18 protrudes through during needle insertion, seals against the body tissue first (because gap G1 is the shortest distance as illustrated in FIG. 4) and the vacuum suction force in that vacuum groove 50 approaches the negative fluid pressure level of the fluid pressure source 31. The second valve 52-2 can be configured to open in response to an increase in the negative fluid pressure level (increased vacuum suction force) indicating that gap G (FIG. 4) between the bottom wall 12-2 of the device housing 12 and the tissue has decreased because the smallest diameter and central-most vacuum groove 50 is sealed against the tissue. The third valve 54-3 can be configured to open in response to a further increase in the negative fluid pressure level (further increased vacuum suction force) indicating that gap G between the bottom wall 12-2 of the device housing 12 and the body tissue has decreased again because the prior vacuum groove 52 has sealed against the tissue and so on.

In some embodiments, the negative fluid pressure applied to the tissue of the patient's body can be approximately 0.5 to approximately 4 pounds per square inch gauge (psig) (approximately 3.4 kPa to approximately 27.6 kPa) and can typically be approximately 1.5 psig to approximately 2.5 psig (approximately 10.3 kPa to approximately 17.2 kPa). An approximately 1.5 psig to approximately 2.5 psig (approximately 10.3 kPa to approximately 17.2 kPa) negative fluid pressure may increase the ability of the fluid pressure source 31 to maintain negative fluid pressure during minor disruptions without exhaustion. In addition, the approximately 1.5 psig to approximately 2.5 psig (approximately 10.3 kPa to approximately 17.2 kPa) negative fluid pressure can provide a good compromise between providing adequate adhesive force while limiting capillary breakage in the body tissue of the patient. Applying a larger negative fluid pressure may allow more opening pressure tolerance in the valves 50-2, 52-2, and 54-2 and other components of the system. This in turn, may allow less expensive valves and other components with larger tolerances to be used, thereby reducing the cost of the system.

The fluid pressure distributed in the sequential valve arrangement can be regulated in some embodiments at the vacuum ports 50-1, 52-1, 54-1 or other points of application by implementing the branch lines 56-1, 56-2, and 56-3 with relatively flexible tubes that collapse upon themselves under the negative fluid pressure (the vacuum supply line 56 would be implemented with relatively inflexible tubing which does not collapse upon itself under the negative fluid pressure). The flexibility of the branch lines can be selected so that the branch lines 56-1, 56-2, 56-3 collapse upon themselves at a desired negative fluid pressure to substantially occlude fluid flow (e.g., air-flow) through the branch lines 56-1, 56-2, 56-3. Accordingly, the flexible branch lines 56-1, 56-2, 56-3 operate as inexpensive fluid pressure regulators to limit or prevent the system from applying full negative fluid pressure to the body tissue. The tubing material, durometer, outside diameter, inside diameter, and any combination thereof can be selected to provide the branch tubes 56-1, 56-2, 56-3 with the appropriate flexibility so that they collapse and substantially occlude fluid flow at a desired negative fluid pressure. In some embodiments the desired negative fluid pressure can be, but is not limited to −1.5 pounds per square inch differential (psid) to ambient pressure (approximately −10.3 kPa to ambient pressure), i.e., 1.5 pounds per square inch (psi) less than ambient pressure (approximately 10.3 kPa less than ambient pressure).

FIG. 5B is a table which shows the fluid pressure in pounds per square inch absolute (psia) at various points within the sequential valve arrangement and serial fluid pressure distribution structure (system) embodied in FIG. 5A at different transitions of the valves and branch lines, according to an illustrative embodiment of the disclosure. The table assumes the system initially seals against the body tissue at vacuum ports 50-1, 52-1, and 54-1 and that the system is not constrained by vacuum supply P1. In this embodiment, the flexible branch lines 56-1, 56-2, 56-3 are set to close at approximately −1.5 psid to ambient pressure (approximately −10.3 kPa to ambient pressure) and the check valves 50-2, 52-2, 54-2 are set to open at approximately 2.0 psid across the valve (approximately 13.8 kPa across the valve). It should be understood that in various other embodiments, the fluid pressure at the various points within the sequential valve arrangement and serial fluid pressure distribution structure of FIG. 5A can vary from what is shown in the table of FIG. 5B, depending upon factors including, but not limited to the closing fluid pressures of the flexible branch lines 56-1, 56-2, 56-3, the opening fluid pressures of the valves 50-2, 52-2, and 54-2, and the like.

If the fluid pressure source 31 fails, the check valves 50-2, 52-2, and 54-2 can maintain the negative fluid pressure. In some embodiments, it may be beneficial for the check valve opening pressure to be higher than the negative pressure applied to the body tissue so that it will be isolated from subsequent lines as well. Therefore, in such embodiments, the valves 50-2, 52-2, and 54-2 should have an opening pressure which is at least greater than the closing pressure of the branches lines 56-1, 56-2, 56-3, and the branch line close pressure should be very close to or the same as the pressure applied to the patient. For example, in one non-limiting embodiment, the branch lines 56-1, 56-2, 56-3 may close at approximately 1.5 psid below ambient pressure (approximately 10.3 kPa below ambient pressure) and the check valves 50-2, 52-2, and 54-2 may open at approximately 2.0 psid differential pressure (approximately 13.8 kPa differential pressure). Accordingly, a loss of seal at the most distal branch line 56-3 from the fluid pressure source 31 can still maintain a negative fluid pressure at the body tissue if the check valve opening pressure of the vacuum supply line 56 is greater than net application of vacuum suction force at the body tissue. If the body tissue seal at the most distal branch line 56-3 is disturbed, then the next branch line 56-2 will only retain vacuum suction force equal to the check valve opening pressure. So if the target negative fluid pressure is for example, approximately −1.5 psig (approximately −103 kPa) at the body tissue, the check valves 50-2, 52-2, 54-2 along the vacuum supply line 56 should have an opening pressure of at least 1.5 psid or one breach will affect the subsequent branch line.

Alternatively, using the prior vacuum levels of the grooves as a reference pressure, but not in-line, may allow the grooves 50, 52, 54, to be closed from the vacuum supply of the fluid pressure source 31 via their corresponding valves 50-2, 52-2, 54-2 and maintain vacuum suction even if the negative pressure level of the fluid pressure source 31 is exhausted due to faulty sealing or challenging tissue geometry.

In further embodiments, the fluid pressure distribution system may comprise a parallel structure of plural vacuum supply lines distributing fluid pressure to the vacuum ports (not shown). Although serial fluid pressure distribution structures may be less costly and simpler to implement than parallel fluid pressure distribution structures, parallel structures may reduce the effect of losing a seal at one or more of the application locations (e.g., vacuum ports) and may reduce the total pressure differential required of the system, because the parallel structures do not require multiple valves in series to minimize disruption impact.

In still further embodiments, the fluid pressure distribution system may comprise a combination of one or more serial and one or more parallel fluid pressure distribution structures.

Figure 6:
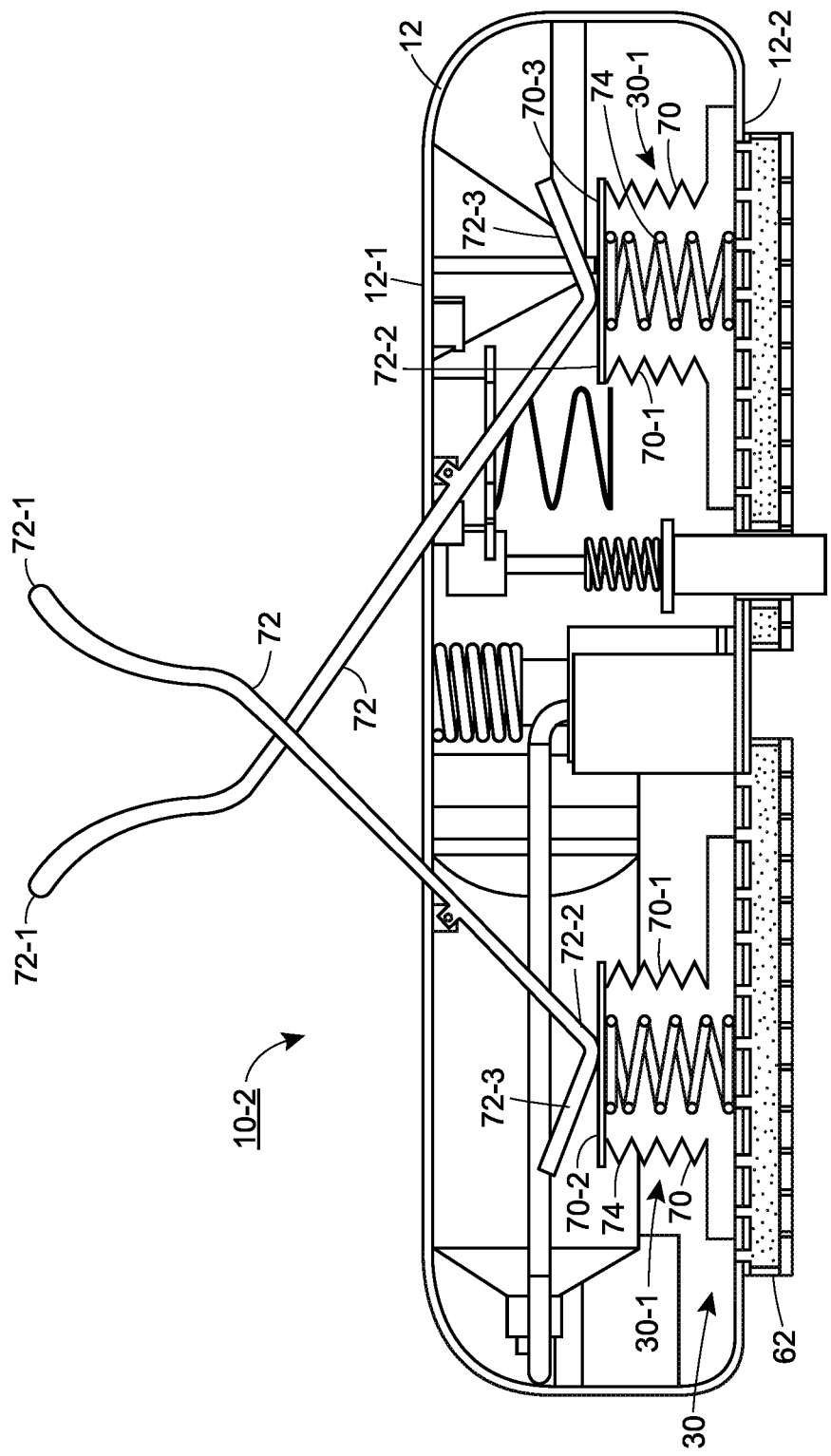
FIG. 6 is an elevational view of the drug delivery device according to another embodiment of the disclosure, with certain elements of the device shown in cross-section or cut-away to reveal other elements.

FIG. 6 shows another embodiment of the drug delivery device 10-2. In this embodiment of the device 10-2 the fluid pressure source 31 comprises two flexible pressure-vacuum chambers 70 that can each be expanded (to a maximum volume state) and collapsed (to minimum volume state) by the patient or operator via a lever 72. The flexible pressure-vacuum chambers 70 may each comprise a flexible bellows 70-1 sealed at a first end by a rigid end wall 70-2 and sealed at a second end by the bottom wall 12-2 of the device housing 12. Each of the levers 72 may be pivotally attached to the top wall 12-1 of the device housing 12 and have a first end 72-1 that extends through an opening in the top wall 12-1 of the housing 12 and a second end 72-2 that engages the rigid end wall 70-2 of its respective flexible pressure-vacuum chamber 70. Some embodiments of the device 10-2 may use only a single flexible pressure-vacuum chamber 70 and other embodiments of the device 10-2 may use three or more flexible pressure-vacuum chambers 70. In addition, the levers 72 in some embodiments, may be configured to collapse more than one pressure-vacuum chamber 70.

Each flexible pressure-vacuum chamber 70 may contain biasing element 74 including, but not limited to a coil spring, which assists in re-expanding the pressure-vacuum chamber 70 after it has been collapsed by the lever 72. The second end 72-2 of each lever 72 may include a foot 72-3 that slides on the rigid end wall 70-2 of the flexible pressure-vacuum chamber 70 when the lever 72 pivots during the collapse and expansion of the chamber 70.

The levers 72 may be arranged so that the first ends 72-1 of the levers 72 cross one another, thereby allowing the patient to pinch them together to compress or bend the biasing elements 74 and collapse the flexible pressure-vacuum chambers 70 to exhaust the air from inside the chambers 70, prior to use of the device 10-2. In some embodiments, the air can be exhausted through a one-way valve (not shown) provided in the bellows 70-1 or any other suitable portion of the flexible pressure-vacuum chamber 70, which opens under a positive fluid pressure (collapse of the chamber 70) and which closes under a negative fluid pressure (expansion of the chamber 70). In other embodiments, the air exhausted from the flexible pressure-vacuum chambers 70 creates a positive fluid pressure which can be applied to the laminate 62 via the vacuum ports (not visible) of the one or more vacuum grooves 42 (or apertures 42 if applicable) defined in or by the bottom wall 12-2 of the device housing 12, which in turn is applied to the removable sterile barrier film, which may cover the laminate 62 prior to use of the device 10-2. The positive fluid pressure applied to the sterile barrier film breaks the seal between the film and the laminate 62, thereby facilitating the removal of the film therefrom. When the device 10-2 is activated, the collapsed flexible pressure-vacuum chambers 70 (in the minimum volume state) are expanded by the biasing elements contained therein. As the flexible pressure-vacuum chambers 70 expand, they generate the negative fluid pressure or vacuum suction that is applied to the vacuum ports (not visible of the one or more vacuum grooves 42 (or apertures 42 if applicable) defined in or by the bottom wall 12-2 of the device housing 12.

In some embodiments, the levers 72 can be decoupled from the flexible pressure-vacuum chambers 70 after activation of the device 10-2. In other embodiments, the levers 72 can be configured to slide rather than pivot to collapse and expand the flexible pressure-vacuum chambers 70. In other embodiments, the levers 72 can also be configured to activate the device 10-2. The flexible pressure-vacuum chamber and lever arrangement described above can also be used in embodiments of the device that do not use an adhesive system or which use an adhesive system that comprises a double-sided medical adhesive.

Figure 7A:
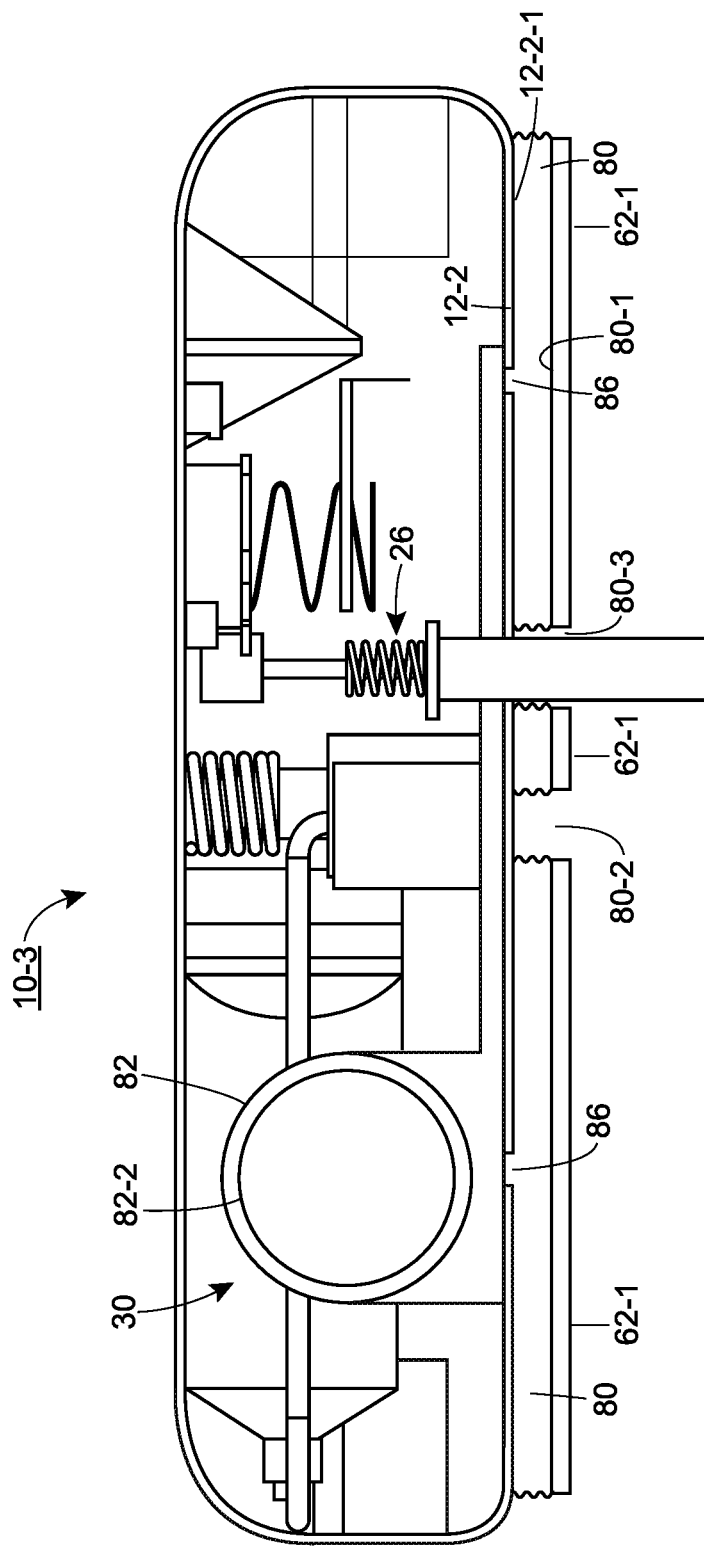
FIG. 7A is an elevational view of the drug delivery device according to another embodiment of the disclosure, with certain elements of the device shown in cross-section.

FIG. 7A shows another embodiment of the device 10-3. The device 10-3 is similar to the devices described earlier except the device 10-3 comprises a bladder 80 (depicted in the unpressurized state) attached to the outer surface 12-2-1 of the bottom wall 12-2 of the device housing 12, and the fluid pressure source of the pneumatic system 30 comprises a plunger pump 82 pneumatically coupled to the bladder 80. The device 10-3 can further optionally include a conventional flexible adhesive layer 62-1 attached to a bottom surface 80-1 of the bladder 80. The plunger pump 82 may be mounted on the bottom wall 12-2 of the device housing 12 and enclosed therein. The bottom wall 12-2 of the housing 12 includes one or more ports 86, which allow the plunger pump 82 to pneumatically communicate with the interior of the bladder 80 to selectively provide negative and positive fluid pressures within the bladder 80. One or more valves (not shown) may be provided to selectively close and open the ports 86. Openings 80-2 and 80-3 extend through the bladder 80 and adhesive layer 62 to allow the injection needle 18 (not visible) and the sensing pin 26-1 of the body proximity sensor 26 to extend therethrough. Operation of the device 10-3 in FIG. 7A will be described below after a discussion of the plunger pump 82.

Figure 8A:
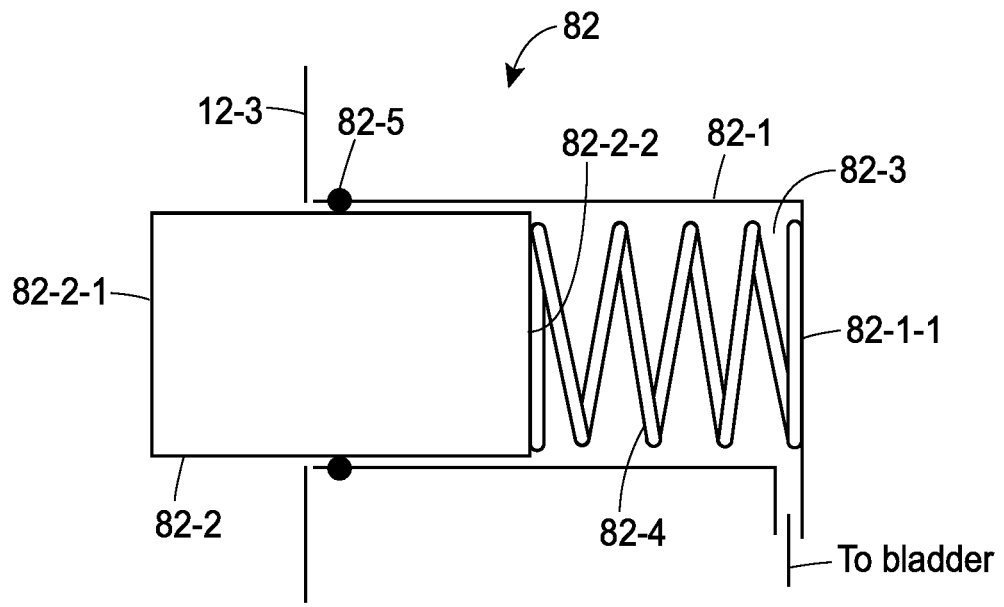
FIG. 8A is a cross-sectional view of a plunger pump fluid pressure source according to an embodiment of the disclosure.

Referring to FIG. 8A, various embodiments of the plunger pump 82 may comprise a rigid cylinder 82-1 of any desired shape including, but not limited to round, elliptical, oval, square, and the like, closed at one end by an end wall 82-1-1, and a correspondingly shaped plunger 82-2 reciprocally disposed in the cylinder 82-1. The plunger 82-2 may include opposing free and working ends 82-2-1 and 82-2-2, respectively. The free end 82-2-1 of the plunger 82-2 may extend out through an opening in the side wall of the housing 12 (FIG. 8D) to allow the patient or operator to depress and thereby actuate the pump 82. The space between the working end 82-2-2 of the plunger 82-2 and the end wall 82-1-1 of the cylinder 82-1 defines a pressure-vacuum chamber 82-3. A biasing element 82-4 including, but not limited to a spring, may be disposed between the working end 82-2-2 of the plunger 82-2 and the end wall 82-1-1 of the cylinder 82-1. An elastomeric seal 82-5 including, but not limited to an O-ring, may be disposed in a groove formed in the inner wall surface of the cylinder 82-1, at the opening thereof, or disposed in a groove formed in the outer wall surface of the plunger 82-2 adjacent to the working end 82-2-2 thereof, to pneumatically seal the chamber 82-3.

Figure 8B:
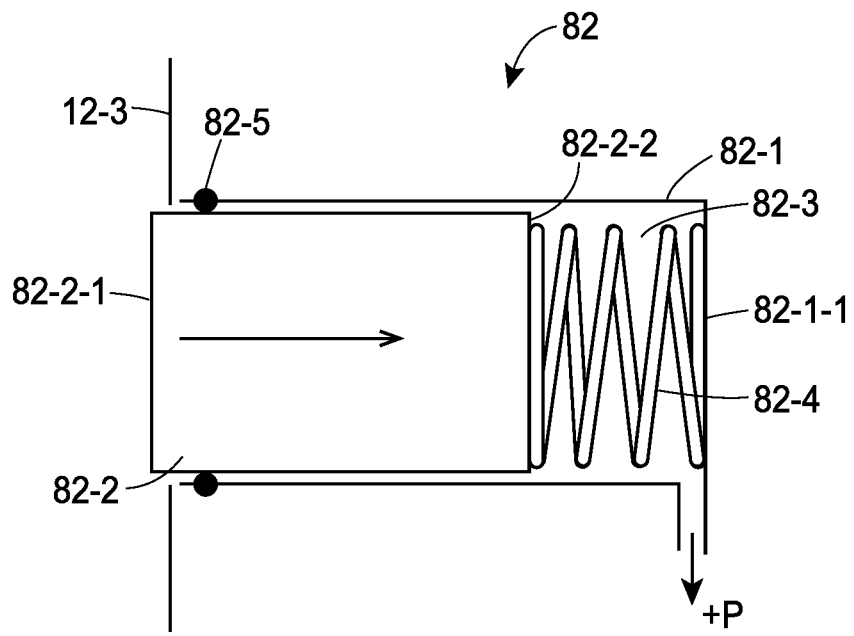

As shown in FIG. 8A, the biasing element 82-4 normally maintains the plunger 82-2 of the plunger pump 82 in an extended position relative to the cylinder 82-1 prior to deployment of the bladder 80. When the plunger 82-2 is pressed into the cylinder 82-1 to a depressed position by the patient or operator to pressurize and thereby deploy the bladder 80 or evacuate and thereby retract the bladder 80 (depending upon the selected operating mode of the pump 82), the biasing element 82-4 is compressed between the working end 82-2-2 of the plunger 82-2 the end wall 82-1-1 of the cylinder 82-1, as shown in FIG. 8B. When the plunger 82-2 is released, as shown in FIG. 8C, either by the patient or by actuation of the activation mechanism, the biasing element 82-4 moves the plunger 82-2 back to the extended position from the depressed position. In some embodiments, the releasing the plunger 82-2 may be used to evacuate and retract the bladder 80.

As shown in FIG. 8D, the plunger 82-2 in some embodiments may include a low vacuum indicator 83 including, but not limited to a colored or marked section of the plunger 82-2. In some embodiments, the indicator 83 may extend about one third of the way along the outer surface of the plunger 82-2 from the working end 82-2 thereof so that it becomes visible if the vacuum level drops below a desired threshold. If this occurs, the patient or operator can push the plunger 82-2 one or more times to re-establish the appropriate vacuum level which will conceal the indicator 83 within the device housing 12.

FIG. 8E shows another embodiment of the plunger pump 92 that comprises a movable cylinder 92-1 and a fixed plunger 92-2 disposed within the movable cylinder 92-1. The movable cylinder 92-1 may be pressed by the patient or operator to activate the pump 92. The biasing element 92-4 is disposed outside of the pressure-vacuum chamber 92-3. In embodiments of the device that do not require positive pressure, the plunger pump 92 may include a valve 92-5 including, but not limited to a flapper valve, which opens under a positive fluid pressure and which closes under ambient or negative fluid pressure. Such a valve may also be used in the pressure pump depicted in FIGS. 8A-8D. A ballast chamber (not shown) may be provided inline after the flapper valve 92-5 to improve vacuum performance and allow multiple compressions of the plunger 92-2.

In some embodiments, the plunger pump 82 shown FIGS. 8A-8D or the plunger pump 92 shown in FIG. 8E may also be used in the devices shown in FIGS. 1 and 4, which do not include the bladder.

Figure 7B:
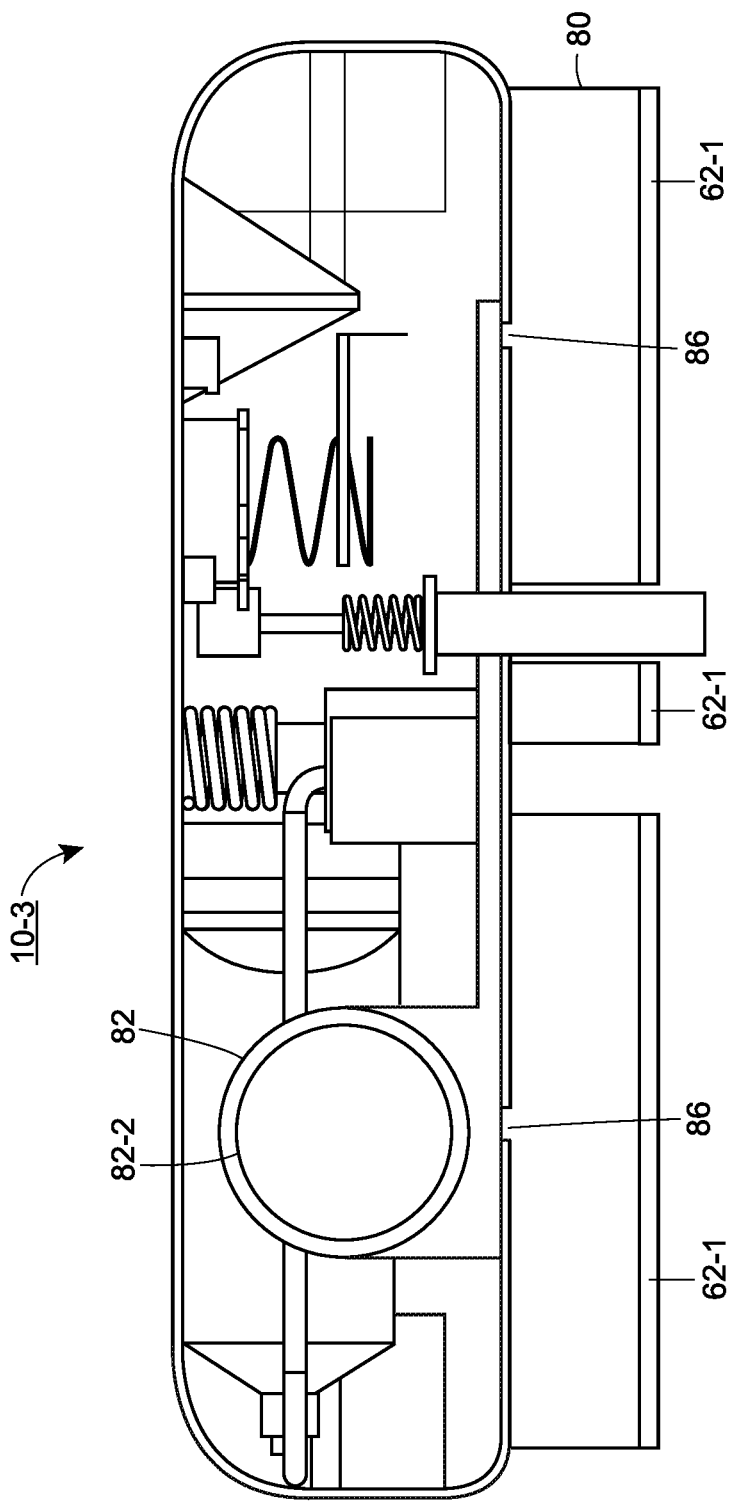
FIGS. 7B-7D depict the operation of the drug delivery device of FIG. 7A.
Figure 7C:
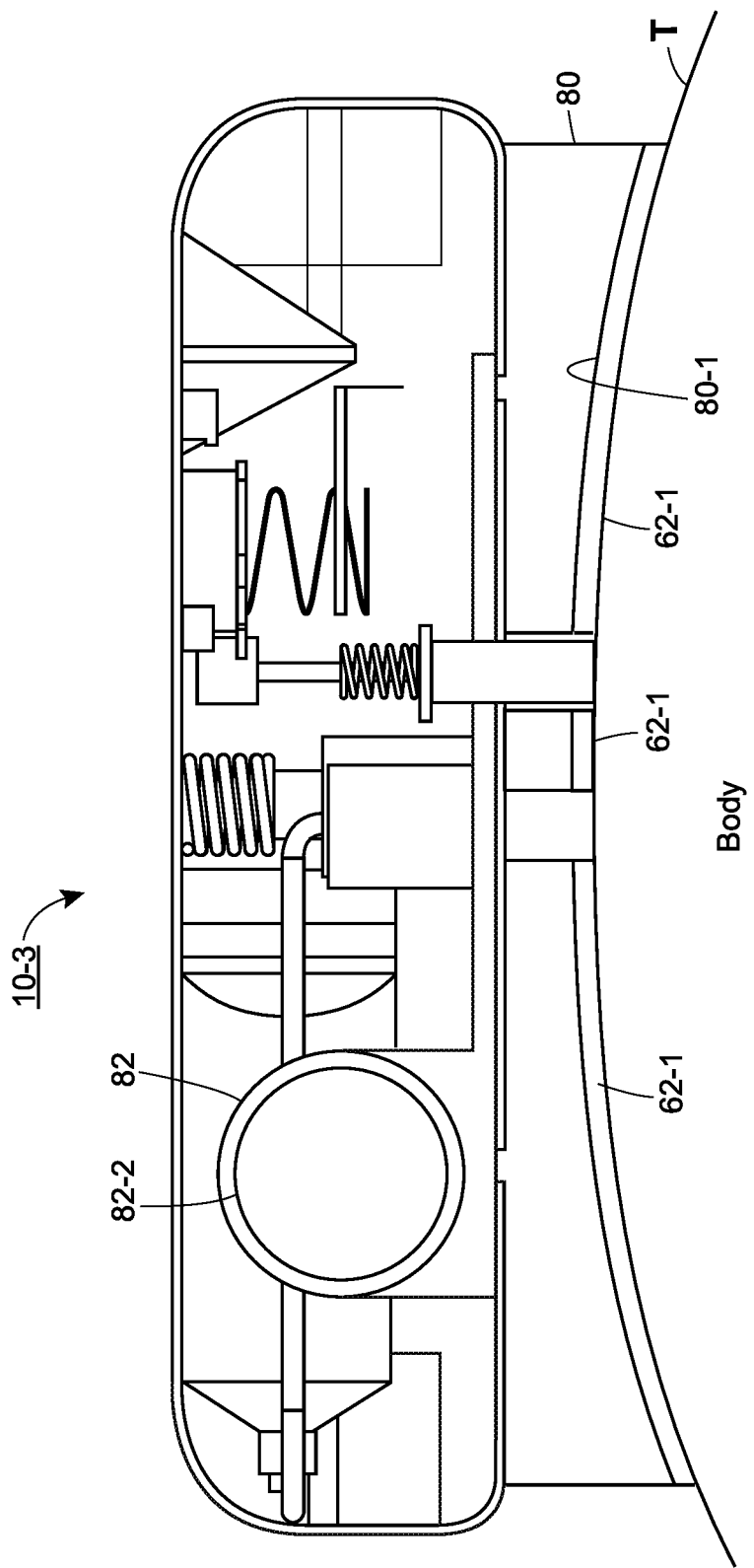
Figure 7D:
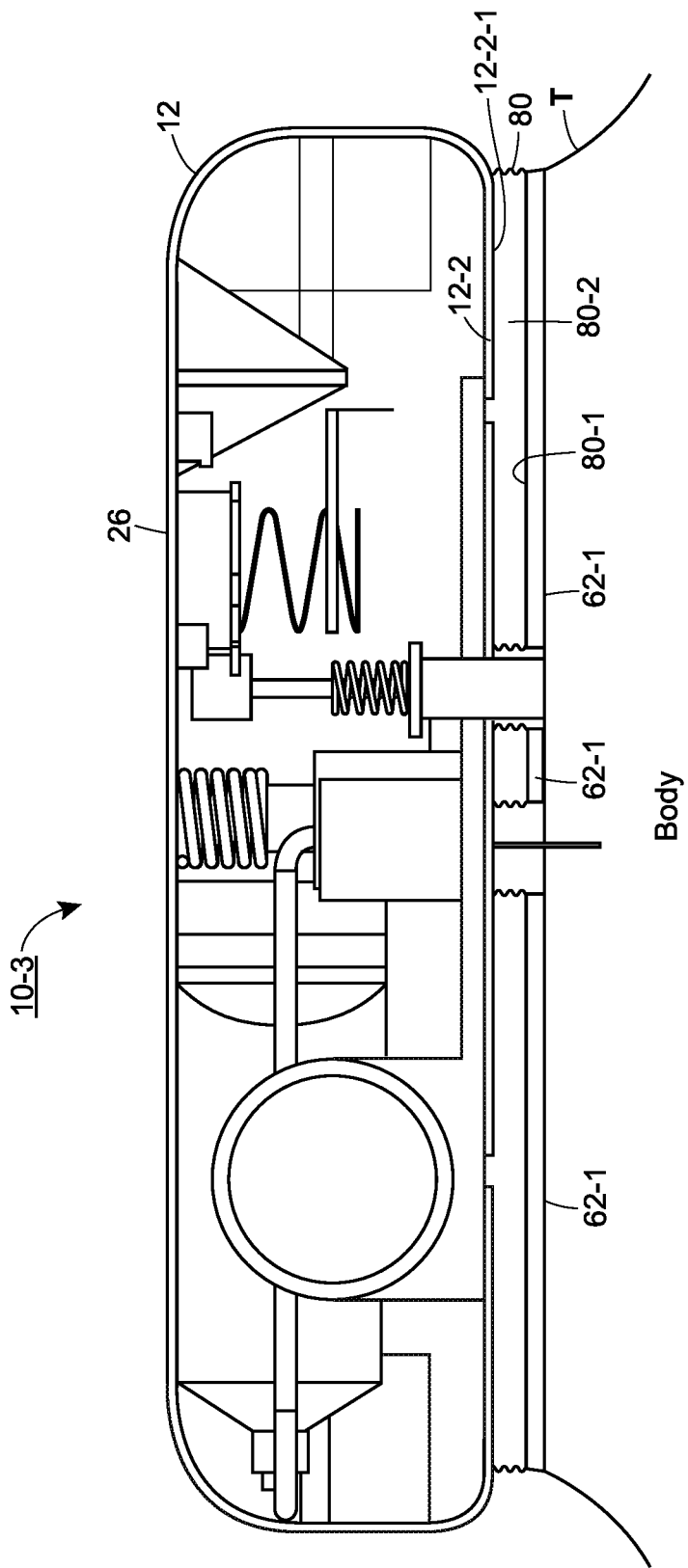

FIGS. 7B-7D depict the operation of the device 10-3 of FIG. 7A according to an embodiment of the disclosure. Referring first to FIG. 7B, the device 10-3 may be operated by pressing the plunger 82-2 of the plunger pump 82 into the device housing 12, which causes the plunger pump 82 to generate a positive fluid pressure in the interior of the bladder 80, which pressurizes the bladder 80 and at least partially inflates or expands it. A valve (not shown) may be provided in the cylinder 82-1 or in any other suitable portion of the plunger pump 82, to bleed off any excess pressure which may overinflate the bladder 80.

In FIG. 7C, the device 10-3 may be applied to the body tissue T of the patient at a selected injection site with an application force. The partially inflated bladder 80, and particularly the bottom wall 80-1 of the bladder 80 with the flexible adhesive layer 62-1, conforms to the contour of the patient's body tissue T at the injection site when the device 10-3 is applied thereto. As the bottom wall 80-1 of the bladder 80 flexes, it conforms the flexible adhesive layer 62-1 to the contour of the body tissue T so that the application force is uniformly distributed across the entire surface area of the adhesive layer 62-1 to more uniformly adhere it to the body tissue T.

Once placed on the body tissue T, the plunger 82-2 may be released from the depressed position, either manually by the patient/user or by activation of the activation mechanism 26. Once released, the plunger pump 82 generates a negative fluid pressure or vacuum suction force which evacuates air from the interior of the bladder 80 and causes the bladder 80 to deflate and retract against the outer surface 12-2-1 of the bottom wall 12-2 of the device housing 12 as shown in FIG. 7D. This causes the flexible adhesive layer 62-1, which is adhered to the body tissue T at the injection site, to pull the body tissue T toward the bottom wall 12-2 of the device housing 12, thereby conforming it to the contour of the bottom wall 12-2 and stretching it taut. In embodiments where the bottom wall 12-2 of the device housing 12 is substantially planar, the body tissue T may be stretched into a substantially planar orientation.

The device 10-3 described with reference to FIGS. 7A-7D may also use the pressure-vacuum chamber 70 and lever 72 arrangement illustrated FIG. 6 instead of plunger pump 82 (FIGS. 8A-8D) or plunger pump 92 (FIG. 8E). Further, the plunger pumps 82 or 92 may be used as the fluid pressure source 31 in the devices 10, 10-1 illustrated in FIGS. 1, 3A-3C and 4.

Figure 9:
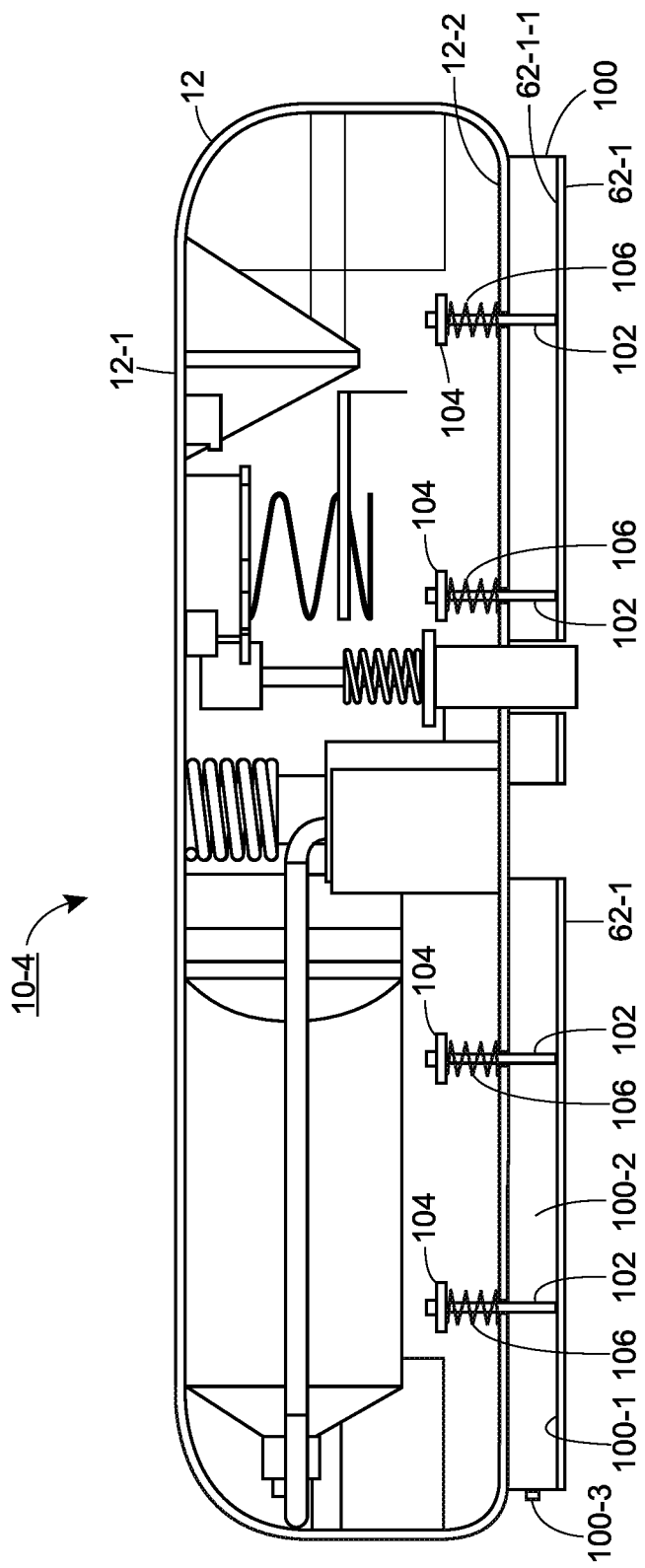
FIG. 9 is an elevational view of the drug delivery device according to another embodiment of the disclosure, with certain elements of the device shown in cross-section.

FIG. 9 shows another embodiment of the drug delivery device 10-4. The device 10-4 is similar to the device 10-3 shown in FIGS. 7A-7D, except the bladder 100 of the device 10-4 is pre-inflated during the manufacturing of the device 10-4 or inflated at the time of use to a small positive pressure including, but not limited to approximately 0.5 psig to approximately 8 psig (approximately 3.4 kPa to approximately 55.2 kPa), to hold the flexible adhesive layer 62-1 away from the bottom wall 12-2 of the device housing 12, prior to the application of the device 10-4 to the body tissue of the patient. In addition, the bladder 100 may include an overpressure vent 100-3 that opens to allow the interior 100-2 of the bladder 100 to be evacuated once a minimum application pressure has been reached, thereby allowing the flexible adhesive layer 62-1 covering the bottom wall 100-1 of the bladder 100 to be mechanically retracted to draw the body tissue toward the bottom wall 12-2 of the device housing 12 and hold it flat against the device 10-4. In some embodiments, the bladder 100 can be mechanically retracted by a plurality of rods 102, provided within the device housing 12, which extend through corresponding openings (not visible) formed in the bottom wall 12-2 of the device housing 12 and connect to the bottom wall 100-1 of the bladder 100 or a base 62-1-1 of the flexible adhesive layer 62-1. Each of the rods 92 in the shown embodiment may be upwardly biased (toward the top wall 12-1 of the device housing 12) by a biasing element 106 including, but not limited to a spring, which may be disposed between the bottom wall 12-2 of the device housing 12 and a retainer 104 fixedly disposed at the top of each rod 102.

Prior to attaching the device 10-4 to the body tissue of the patient, the lightly pressurized bladder 100 of the device 10-4 pulls the rods 102 down, which compresses the springs 106 between the retainers 104 and the bottom wall 12-2 of the device housing 12, and holds the flexible adhesive layer 62-1 away from the bottom wall 12-2 of the device housing 12. When the device 10-4 is placed against the body tissue of the patient and a minimum application pressure is reached, the overpressure vent 100-3 opens to allow the interior 100-2 of the bladder 100 to be evacuated, thereby deflating the bladder 100. As the bladder 100 deflates, the springs 106 expand and raise the rods 102 up, thereby retracting the flexible adhesive layer 62-1 covering the bottom wall 100-1 of the bladder 100 toward the bottom wall 12-2 of the device housing 12 and drawing the body tissue toward the bottom of the device 10-4 to hold it flat against the device 10-4.

In other embodiments, the rods 102 may be made using an elastomeric material such as silicone. The elastomeric rods can now function as biasing elements, thereby allowing the separate biasing elements described above to be omitted. The elastomeric rods 102 can be molded with the base 62-1-1 of the flexible adhesive layer 62-1 to reduce the cost of the device 10-4.

The inflation pressure of the bladder 100 may be selected so the bladder 100 does not completely load the biasing elements, thereby allowing the bladder 100 to conform to the contour and/or soft body tissue of the patient. Further, the biasing force generated by the biasing elements may be selected so that the peak retraction pressure is at least 15 percent lower than the predicted adhesive performance.

In some embodiments, one or more sealing rings may be provided around the injection needle entry site to isolate the negative fluid pressure from the injection site and to prevent the drug from being withdrawn from the entry site. The sealing ring(s) may comprise without limitation an O-ring made using an elastomeric material. As shown in FIG. 2C, the sealing ring(s) 110 in some embodiments may be partially embedded in or disposed on the bottom wall 12-2 of the device housing 12. In other embodiments, the sealing ring(s) 110 may be partially embedded in or disposed on the adhesive laminate 62 as shown in FIG. 3A. In addition, the sealing ring(s) can be used in any of the embodiments disclosed herein.

Figure 10A:
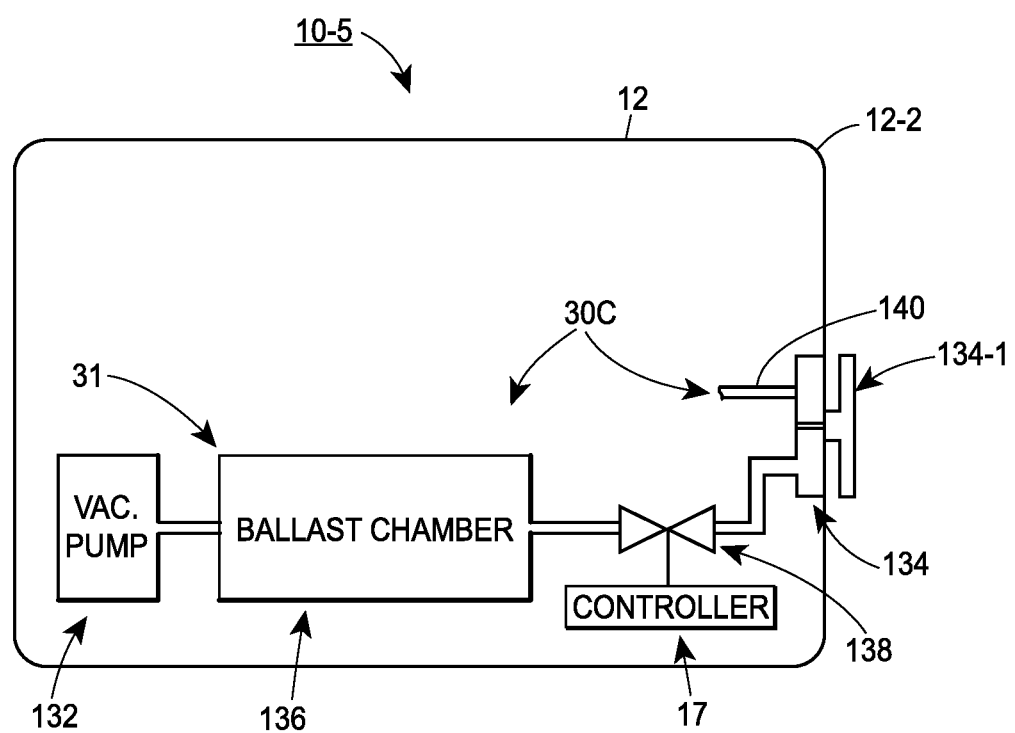
FIG. 10A is a top view of the device with another embodiment of the fluid pressure source.

FIG. 10A shows another embodiment of the drug delivery device 10-5 with a pneumatic system fluid pressure source 31 comprising an electromechanical (active) pump 132, a ballast cylinder or chamber 136 in fluid communication with the pump 132, a user-selectable negative fluid pressure selector (vacuum regulator) 134 in fluid communication with the ballast chamber 136 and the vacuum distribution arrangement 140 in the bottom wall 12-2 of the device housing 12, and a valve 138 (which can be actuated by the controller 17 in some embodiments) disposed between the vacuum regulator 134 and the ballast chamber 136 for activating and deactivating the fluid pressure source 31 of the pneumatic system 30. The vacuum regulator 134 allows the patient or operator to select the negative fluid pressure/vacuum suction force supplied by the active pump 132 and/or ballast chamber 136.

Figure 10B:
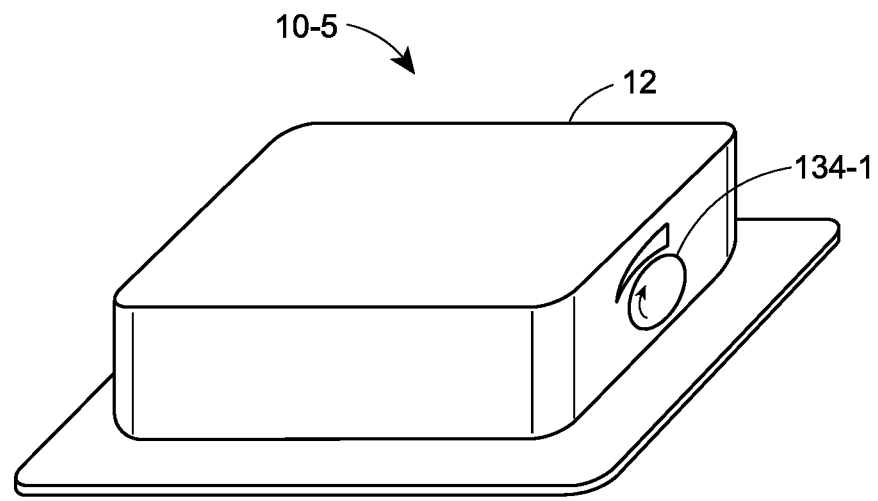
FIG. 10B is a perspective view of the device showing an embodiment of an analog, continuously variable selector of a negative fluid pressure regulator used in the fluid pressure source shown in FIG. 10A to adjust the negative fluid pressure of an active pump of the fluid pressure source.
Figure 10C:
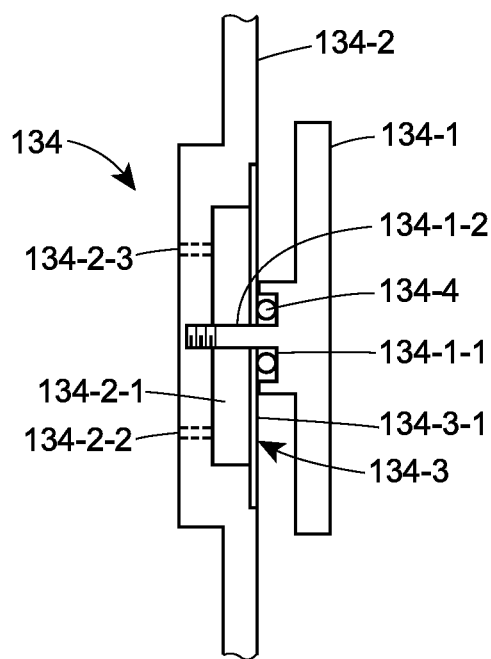
FIG. 10C is a sectional view of an embodiment of the negative fluid pressure regulator used in the fluid pressure source shown in FIG. 10A.

As shown in FIG. 10C, in some embodiments the vacuum regulator 134 may include a housing 134-2 which defines a chamber 134-2-1. The housing 134-2 includes a chamber inlet 134-2-2 in fluid communication with the valve 138 and a chamber outlet 134-2-3 in fluid communication with the vacuum distribution arrangement 140. The regulator chamber 134-2-1 is closed by a thin flexible cap 134-3 that flexes under negative fluid pressure/vacuum suction force. A rotatable adjustment knob or selector 134-1 is provided for allowing a patient or operator adjust or select the negative fluid pressure/vacuum suction force supplied to the vacuum distribution arrangement 140 by the active pump 132 and/or ballast chamber 136. The selector 134-1 may have a shaft 134-1-2 that extends from the back 134-1-1 thereof. The shaft 134-1-2 may extend through the cap 134-3 and threadedly engage the regulator housing 134-2. An O-ring seal 134-4 may be disposed between the back 134-1-1 of the selector 134-1 and the outer surface 134-3-1 of the cap 134-3. When the selector 134-1 is rotated in a first direction, it presses the cap 134-3 and causes it flex inwardly toward the regulator chamber 134-2-1, which increases the negative fluid pressure/vacuum suction force supplied to the vacuum distribution arrangement 140 by the active pump and/or ballast chamber 136. When the selector 134-1 is rotated in a second opposite direction, it allows the cap 134-3 to relax and more easily flex in response to vacuum thus pulling in outside air, which decreases the negative fluid pressure/vacuum suction force supplied to the vacuum distribution arrangement 140 by the active pump and/or ballast chamber 136. The selector 134-1 may be configured as a multi-position selector (not shown) or as an analog, continuously variable selector 134-1 shown in FIG. 10B.

The ballast chamber 136 is especially useful in embodiments that use a low-power version of the active pump 132 and can be omitted when a high-power version of the active pump 132 is used. The ballast chamber 136 can eliminate the need or reduce the number of the valves in the vacuum distribution arrangement 140.

The negative fluid pressure supplied or generated by the active pump 132 can be selected or adjusted in some embodiments by changing the speed, stroke length, and/or power to the pump 132. In other embodiments, the negative fluid pressure supplied by the active pump 132 can be selected or adjusted by changing the differential pressure setting of the valve 138 located before (not shown) or after the pump 132 (shown in FIG. 10A) via the controller 17.

Figure 10D:
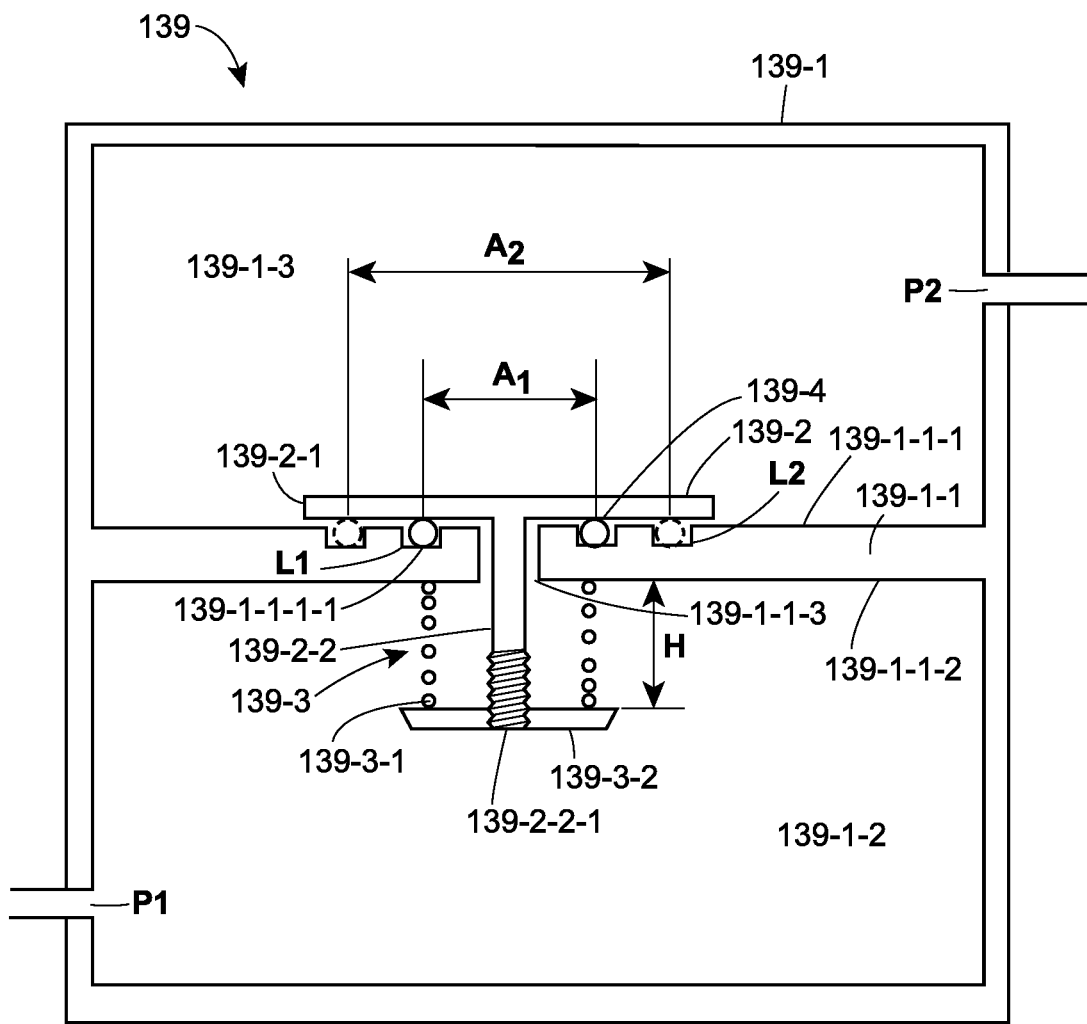
FIG. 10D is a sectional view of an embodiment of a pressure adjustable check valve.

The differential pressure setting of the valve 138 can be changed mechanically if the valve comprises a check valve 139, an embodiment of which is shown in FIG. 10D. The check valve 139 can comprise a housing 139-1, a valve 139-2 disposed within an interior of the housing 139-1, and a valve biasing arrangement 139-3 for biasing the valve 139-2 in a closed position. The housing 139-1 can include an internal partition wall 139-1-1 that divides the interior of the housing 139-1 into first and second chambers 139-1-2 and 139-1-3, respectively. The valve 139-2 can include a head 139-2-1 and a stem 139-2-2. The valve stem 139-2-2 extends through an opening 139-1-1-3 in the partition wall 139-1-1 and can include a threaded free end 139-2-2-1. A first surface 139-1-1-1 of the partition wall 139-1-1 can include a concentric O-ring groove 139-1-1-1-1, located, for example, at location L1 or L2 depending upon the desired vacuum level, which is disposed opposite the valve head 139-2-1. An O-ring 139-4 is disposed in the O-ring groove 139-1-1-1-1. The valve biasing arrangement 139-3 can include a spring retainer 139-3-2 for threadedly receiving the threaded free end 139-2-2-1 of the valve stem 139-2-2 (threaded coupling), and a spring 139-3-1 disposed between a second surface 139-1-1-2 of the partition wall 139-1-1 and the spring retainer 139-3-2. The differential pressure $P_1/P_2$ setting of the valve 139 may be selected by varying the pre-compression of the spring 139-3-1 or other valve biasing element and/or selecting the area of the valve head 139-2-1 that pressure is communicated across. The pre-compression of the spring 139-3-1 or O-ring 139-4 can be increased or decreased by lowering or raising the spring retainer height H, respectively, via the threaded coupling between the threaded free end 139-2-2-1 of the valve stem 139-2-2 and the spring retainer 139-3-2. The area of the valve head 139-2-1 that the pressure is communicated across can be selected by locating the O-ring 139-4 and the O-ring groove 139-1-1-1-1 at location L1 or L2. For example, the area of the valve head 139-2-1 that the pressure is communicated across can be decreased to area $A_1$ by locating the O-ring 139-4 and the O-ring groove 139-1-1-1-1 at location L1. The area of the valve head 139-2-1 that the pressure is communicated across can be increased to area $A_2$ by locating the O-ring 139-4 and the O-ring groove 139-1-1-1-2 at location L2.

Figure 10E:
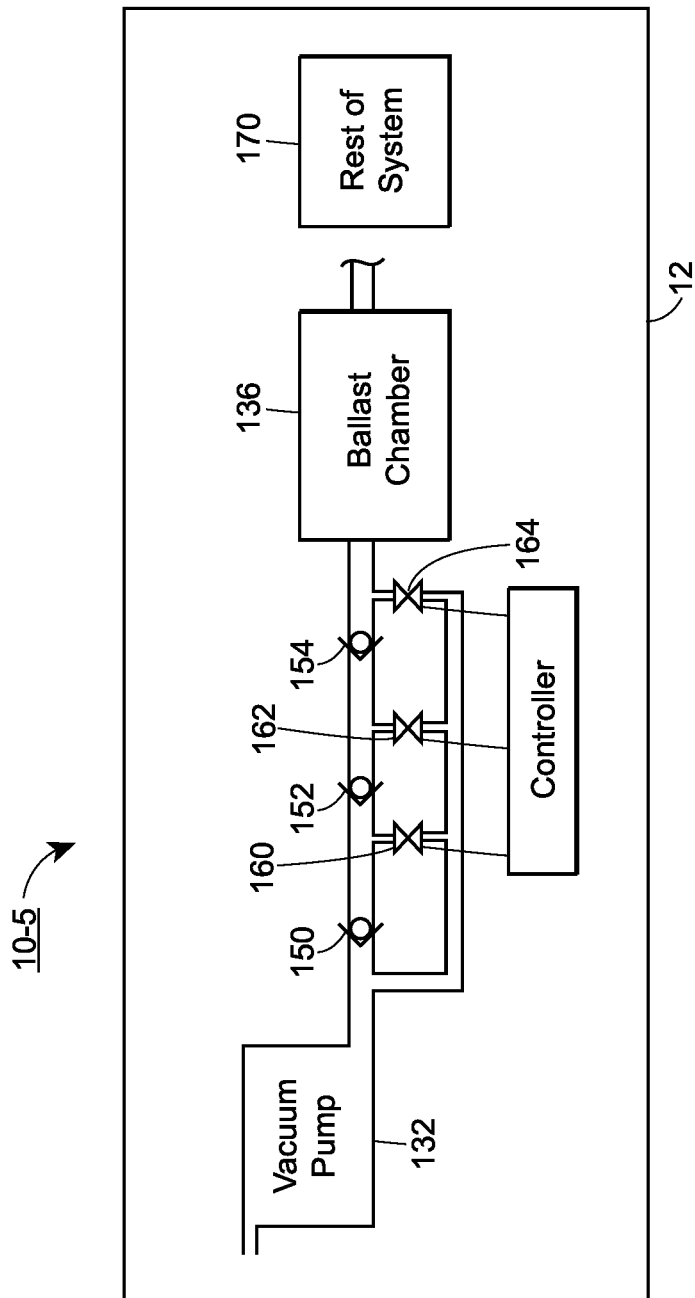
FIG. 10E is a top view of the drug delivery device showing an embodiment of a flow routing arrangement which is used to adjust the negative fluid pressure of the active pump of the fluid pressures source.

As shown in FIG. 10E, in other embodiments, the negative fluid pressure supplied by the active pump 132 can be selected or adjusted by altering the flow path (flow routing) to include or omit none of or one or more of fixed-pressure check valves 150, 152, 154 either before the pump 132, as shown, or after the pump 132. The flow path may be altered by opening and/or closing one or more valves 160, 162, 164, which allow the selection of none or one or more of the check valves 150, 152, 154 in series, thereby reducing the negative fluid pressure (vacuum level) in the rest of the system 170. One or more of the one or more valves 160, 162, 164 may comprise controller actuated gate valves.

The body proximity sensor used in the drug delivery devices described earlier (e.g., FIG. 1) is useful in preventing errors and providing the patient or operator with confidence that the device has been applied correctly. Some patients, however, may find the depressible or deflectable sensing pin 26-1 of the sensor 26 extending from the bottom wall 12 of the device housing somewhat intrusive. Although a capacitive or an optical type body proximity sensor, which has no sensing pin 26-1, can be used in place of the pin sensor 26, such sensors can require a significant amount of electrical energy to power. Further, some patients may find drug delivery device securement, via the negative fluid or vacuum pressure applied to their body tissue by the pneumatic system, objectionable.

Accordingly, in some embodiments of the drug delivery device, the pneumatic system can be implemented as a non-intrusive body proximity sensor, which replaces the pin, capacitive and optical body proximity sensors described previously. In such embodiments, the pneumatic system may apply a lower, less intrusive negative fluid or vacuum pressure than the pneumatic systems described in the previous embodiments, which apply a negative fluid or vacuum pressure that assists in attaching and retaining or solely attaches and retains the device to the body tissue of the patient.

Figure 11:
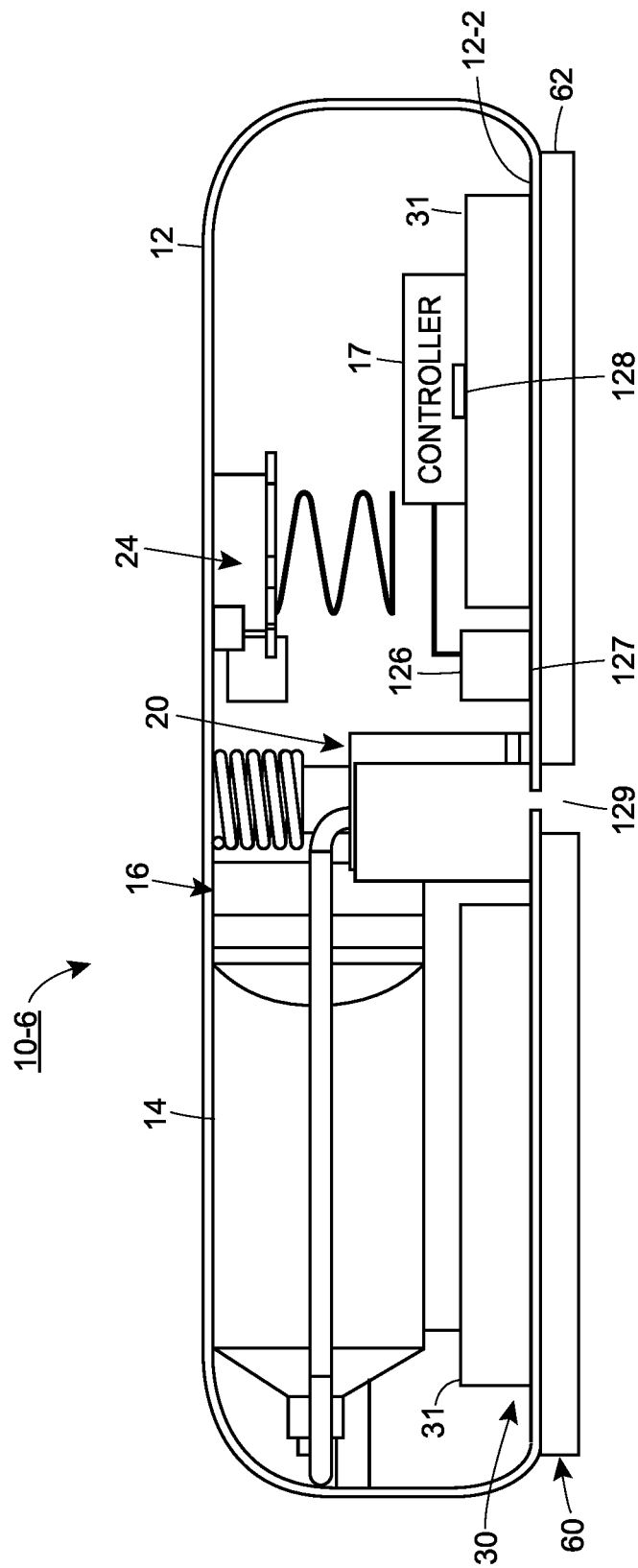
FIG. 11 is an elevational view of another embodiment of the drug delivery device where the pneumatic system includes a pressure sensor which allows it to be operative as a body proximity sensor, with certain elements of the device shown in cross-section.

FIG. 11 shows an embodiment of the drug delivery device 10-6 where the pneumatic system 30 has been adapted and configured as a body proximity sensor. The device 10-6 is similar to the device 10 described earlier and shown in FIG. 1, and therefore can include a housing 12, a primary container 14 for a drug or medicament, a plunger drive mechanism 16, an injection needle (not visible), a needle drive mechanism 20, a device activation mechanism 24, the pneumatic system's fluid pressure source 31, the pneumatic system's fluid pressure distribution arrangement (not visible), a controller 17 and an optional adhesive system 60. The device 10-6 further includes a pressure sensor 126 in place of the body proximity sensor 26 of FIG. 1. The bottom wall 12-2 of the device housing 12 may include an opening 127 (pressure sensing opening) which allows fluid pressure communication between pressure sensor 126 and the adhesive laminate 62 of the adhesive system 60. The pressure sensor 126 senses, through the adhesive laminate 62, any vacuum pressure (and additionally in some embodiments, the positive pressure) generated between the device 10-6 and the body tissue of the patient and outputs a signal which can be monitored, for example, by the controller 17. If the device 10-6 is properly secured to the body tissue of the patient, the pressure sensor 126 should indicate a vacuum pressure between the device and the body tissue. If the device is not properly secured to the body tissue of the patient, the pressure sensor 126 may indicate very little or no vacuum pressure between the device and the body tissue. The controller 17 uses the pressure sensor signal to determine whether the device 10-6 is properly secured to the body tissue of the patient. If the device 10-6 is determined to be properly secured, the injection process can commence or continue on. If the device 10-6 is determined to not be properly secured, the injection process will not be commenced or can be terminated. In embodiments where vacuum pressure is not used to assist or solely attach and retain the device to the body tissue of the patient, the pneumatic system 30 of the device 10-6 may be adapted and configured to generate a lower negative fluid or vacuum pressure between the device 10-6 and the body tissue of the patient than the pneumatic system 30 of the device 10 described earlier and shown in, for example, FIG. 1. In some embodiments, the vacuum pressure can be generated between bottom wall 12-2 of the device housing 12 in area 129 surrounding the opening for the injection needle and the body tissue of the patient. In other embodiments, the vacuum pressure can be generated across the bottom wall 12-2 of the device housing 12 and the body tissue of the patient. In still further embodiments, the pressure sensor, may comprise a strain sensor 128 affixed to a predictably flexible surface subject to negative pressure such as a wall of the pressure chamber 31.

The pneumatic system 30 may also be capable of generating a positive fluid pressure between the device 10-6 and the body tissue of the patient to aid in releasing the device 10-6 from the body tissue of the patient.

The pressure sensor 126 can be configured to measure absolute pressure or differential pressure, however, differential pressure sensing may allow lower vacuum pressures to be used without compromising sensitivity or increasing the risk of false readings due to using the device across a wide range of atmospheric pressures/altitudes.

Figure 12A:
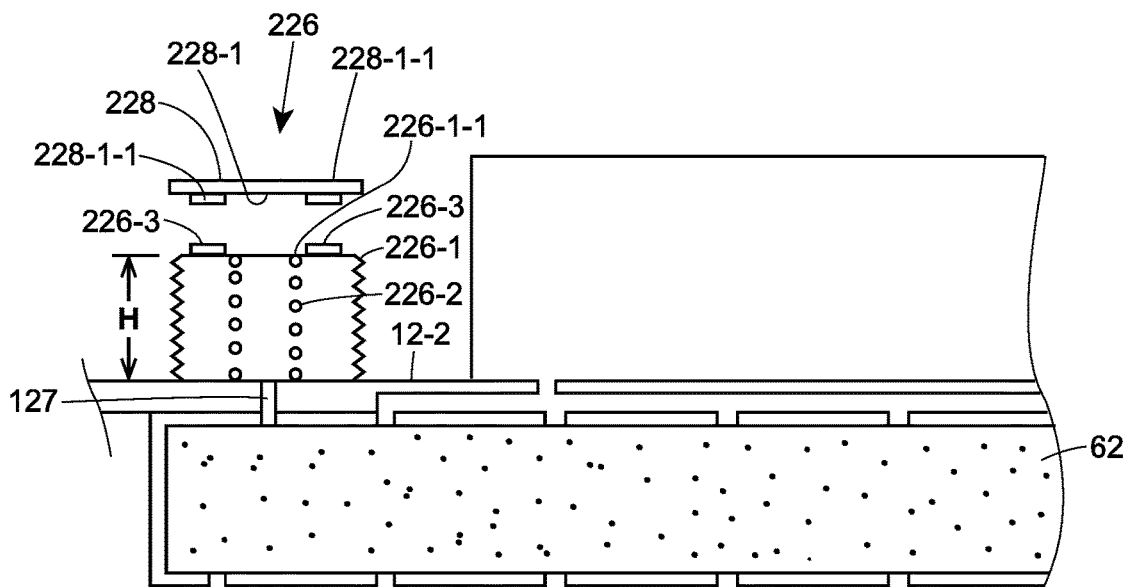
FIG. 12A shows another embodiment of the pressure sensor of drug delivery device.

FIG. 12A shows another embodiment of the pressure sensor 226 of drug delivery device 10-6. The pressure sensor 226 may comprise a flexible bellows 226-1, made for example of an elastomeric or a rubber material, which is closed at one end closed by an end wall 226-1-1. The bellows 226-1 is mounted on the device housing bottom wall 12-2 over the pressure sensing opening 127. A coil spring 226-2 may be disposed within the bellows 226-1 between the end wall 226-1-1 and the bottom wall 12-2 of the device housing 12. The pressure sensor 226 senses through the adhesive laminate 62 of the adhesive system 60 the pressure generated between the device 10-6 (FIG. 11) and the body tissue of the patient.

Figure 12B:
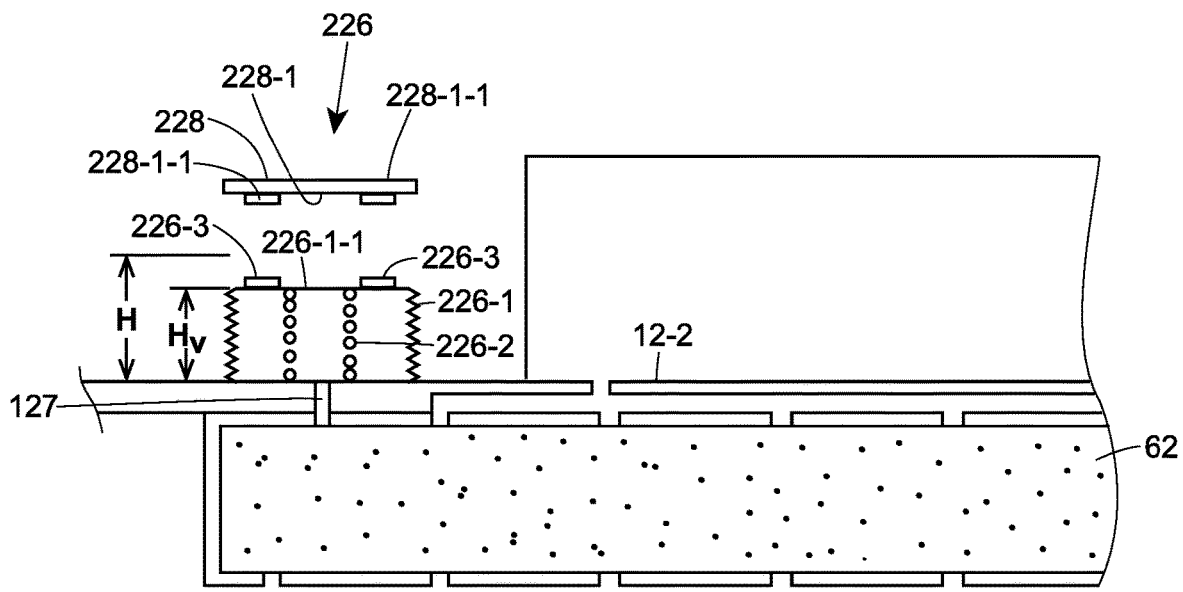
FIGS. 12B and 12C illustrate the operation of the pressure sensor shown in FIG. 12A.
Figure 12C:
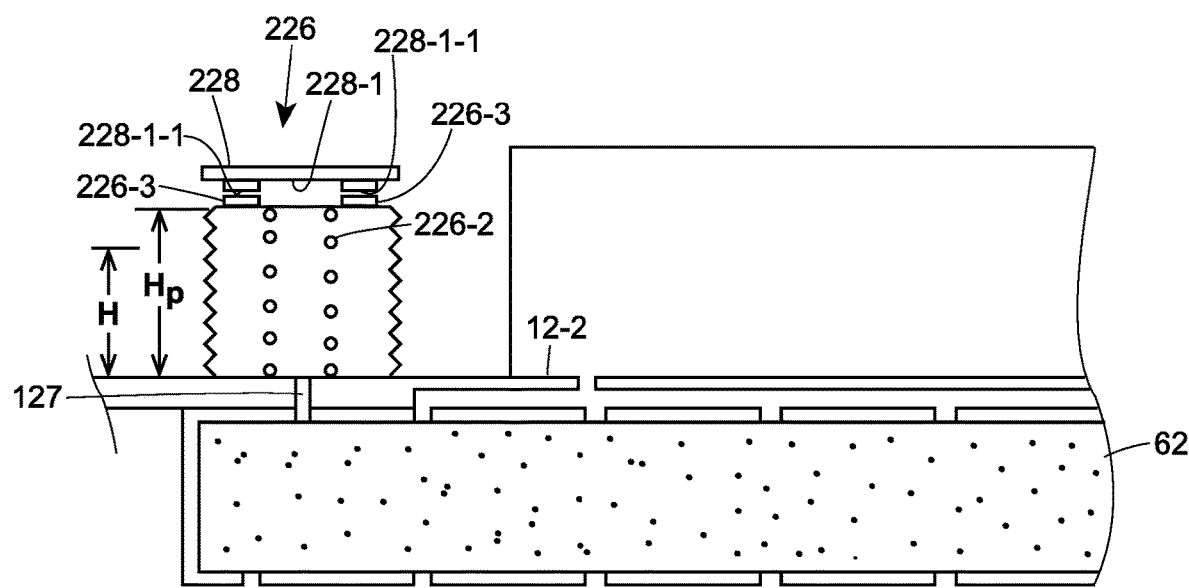

The pressure sensor 226 is shown in a neutral state in FIG. 12A where no vacuum or positive pressure is applied between the device 10-6 and the body tissue of a patient. In the neutral state, the bellows 226-1 may have height H wherein the spring 226-2 has substantially no compressive or tension force acting on it. As shown in FIG. 12B, if the pressure sensor 226 senses a vacuum pressure applied between the device 10-6 and the body tissue of the patient, the bellows 226-1 compresses the spring 226-2 and decreases in height to, for example, height HV. As shown in FIG. 12C, if the pressure sensor 226 senses a positive pressure applied between the device 10-6 and the body tissue of the patient, the 226-1 bellows expands the spring 226-2 and increases in height to, for example, height HP. The height H of the pressure sensor bellows 226-1 can be monitored using any well-known electrical, magnetic, or optical method to allow the determination of whether the device 10-6 is properly secured to the body tissue of the patient. In other embodiments, contacts 226-3 can be provided on the exterior surface of the bellows end wall 226-1-1 which engage corresponding contacts 228-1-1 of a circuit 228-1 provided on, for example, a printed circuit board 228, if the positive pressure sensed by the sensor 226 is above a predetermine pressure (e.g., during release of the device 10-6 from the body tissue of the patient). In some embodiments, the circuit 288-1 may be used with the controller 17 (FIG. 1). In other embodiments, the circuit 228-1 can be adapted to include all the functionality of the controller 17 and therefore replace it.

Figure 13A:
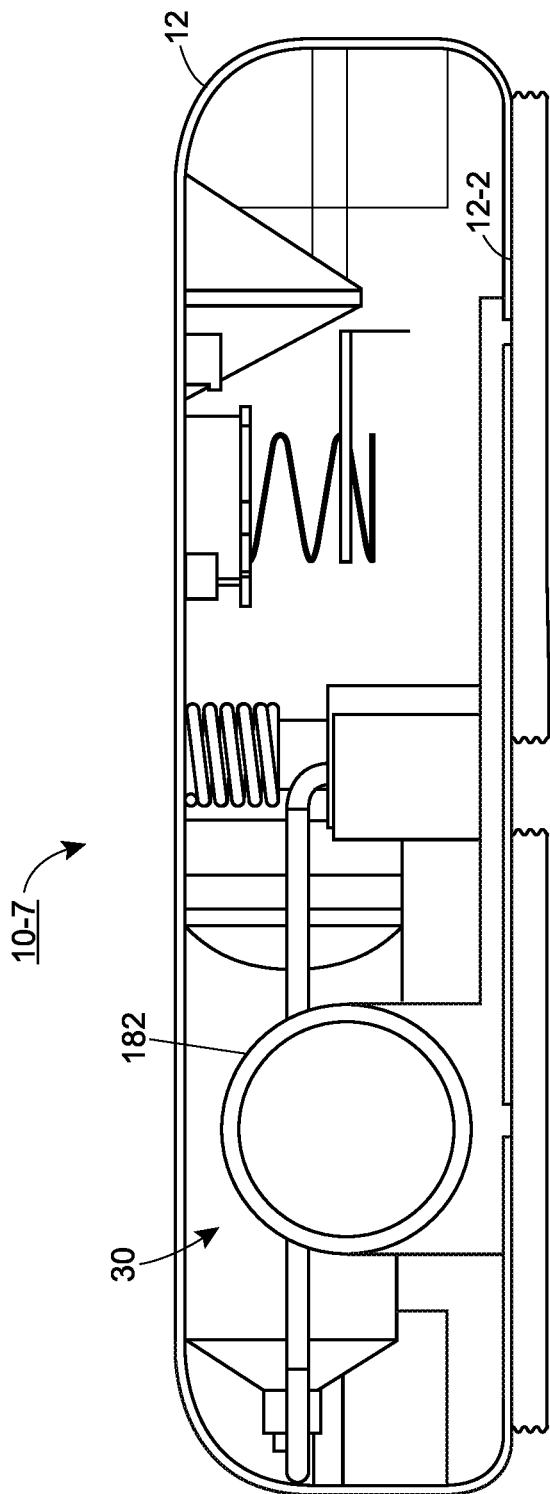
FIG. 13A is an elevational view of another embodiment of the drug delivery device where the pneumatic system includes a plunger pump with a pressure sensor integrated therein which allows it to be operative as a body proximity sensor, with certain elements of the device shown in cross-section.
Figure 13B:
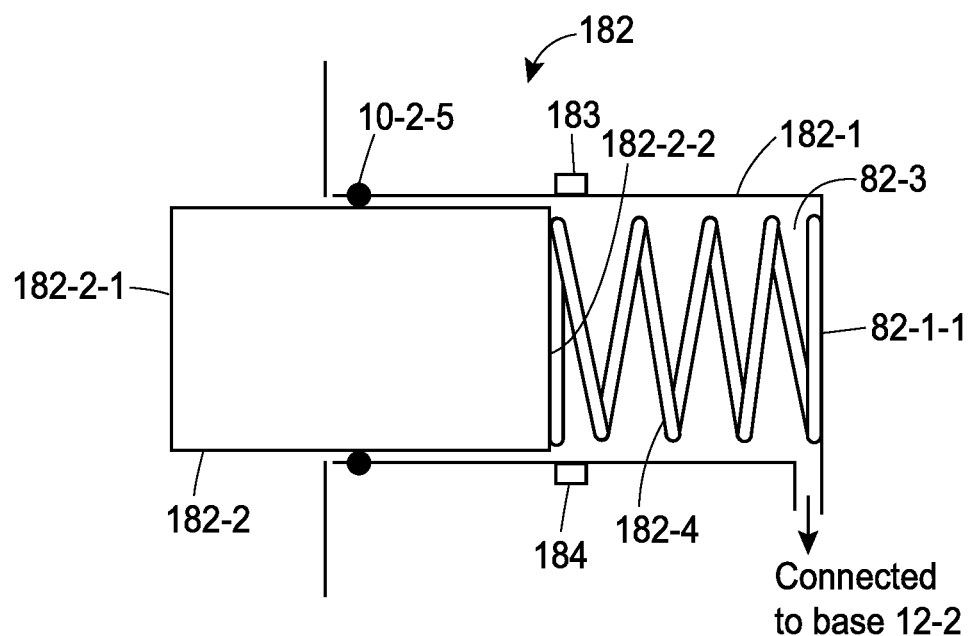
FIG. 13B is a cross-sectional view of the plunger pump with the integrated pressure sensor of FIG. 13A according to an embodiment of the disclosure.
Figure 13C:
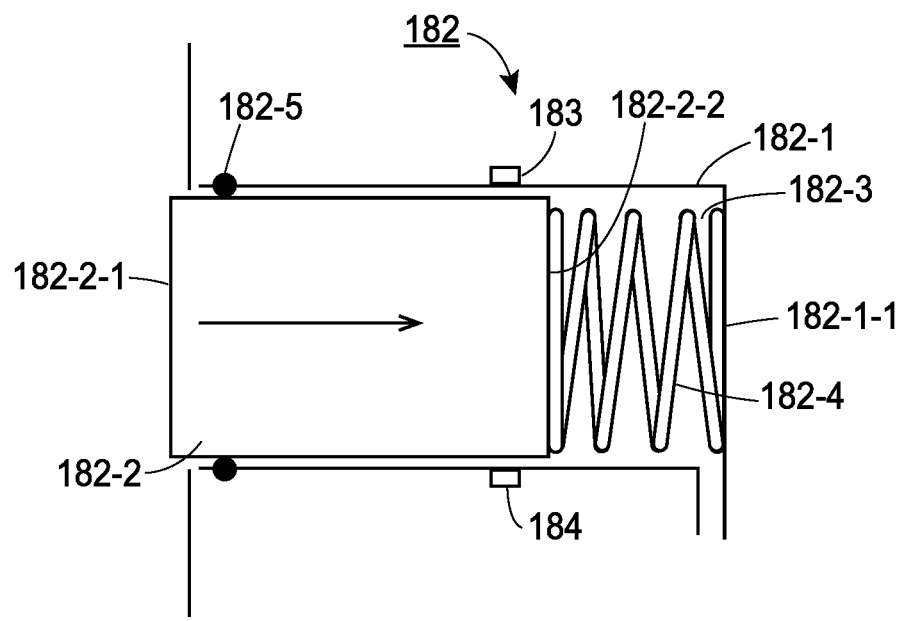
FIGS. 13C and 13D illustrate the operation of the pressure sensor of the plunger pump of FIG. 13B.
Figure 13D:
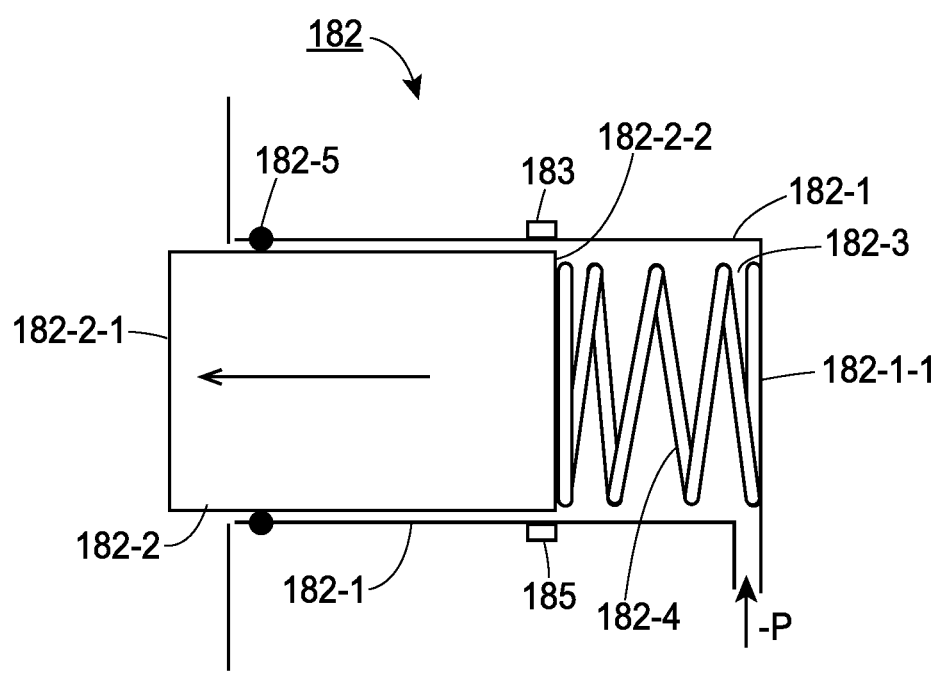

FIGS. 13A-D show another embodiment of the drug delivery device 10-7 where the pneumatic system 30 has been adapted and configured as a body proximity sensor. The device 10-7 is similar to the devices 10 described earlier and shown in FIGS. 1, 2A-2E, and 3A-3C, except that the fluid pressure source of the pneumatic system 30 comprises a plunger pump 182 similar to that described earlier and shown in FIGS. 7A-7C. The plunger pump 182 is adapted and configured to include a pressure sensor 183/184 (FIGS. 13B-13D).

As shown in FIG. 13B, the plunger pump 182 may comprise a rigid cylinder 182-1 closed at one end by an end wall 182-1-1, and a correspondingly shaped plunger 182-2 reciprocally disposed in the cylinder 182-1. The plunger 182-2 may include opposing free and working ends 182-2-1 and 182-2-2, respectively. The free end 182-2-1 of the plunger 182-2 extends out from the cylinder 182-1 to allow the patient or operator to depress and thereby actuate the pump 182. The space between the working end 182-2-2 of the plunger 182-2 and the end wall 182-1-1 of the cylinder 182-1 defines a pressure-vacuum chamber 182-3. A biasing element 182-4 including, but not limited to a spring, may be disposed between the working end 182-2-2 of the plunger 182-2 and the end wall 182-1-1 of the cylinder 182-1. An elastomeric seal 182-5 including, but not limited to an O-ring, may be disposed in a groove formed in the inner wall surface of the cylinder 182-1, at the opening thereof, or disposed in a groove (not visible) formed in the outer wall surface of the plunger 182-2 adjacent to the working end 182-2-2 thereof, to pneumatically seal the chamber 182-3. The cylinder 182-1 applies vacuum pressure (and positive fluid pressure in some embodiments depending upon the selected pump mode) to the bottom wall 12-2 of the device housing 12 (FIG. 13A). The pressure sensor may include any device which is capable of monitoring the movement of the plunger 182-2 relative to the cylinder 182-1. In the shown embodiment, the pressure sensor comprises an optical source 183 that generates an optical signal S, such as a light beam, and an optical receiver 184 that receives the optical signal, such as a light sensor. The optical source 183 can be embedded in or disposed on the surface of the cylinder 182-1 and the optical receiver 184 can be embedded in or disposed on the surface of the cylinder 182-1 opposite the optical source 183 and aligned therewith so that the optical source 183 and optical receiver 184 face one another across the bore of the cylinder 182-1. The optical receiver 184 can be adapted to generate a first output signal that indicates that none or insufficient vacuum pressure is being generated between the device and the patient's body tissue when the optical receiver 184 receives the optical signal generated by the optical source 183. The optical receiver 184 can also be adapted to generate a second output signal which indicates that sufficient vacuum pressure is being generated between the device and the patient's body tissue when the optical receiver 184 does not receive the optical signal generated by the optical source 183. In some embodiments, the optical receiver 184 may transmit the output signals to the controller 17, which in turn, uses the signals to determine whether to commence with or continue the injection process.

Prior to applying the device 10-7 to the patient's body tissue, the plunger 182-2 is pressed into the cylinder 182-1 to evacuate air from the cylinder 182-1 as shown in FIG. 13C. The device 10-7 is then applied to the patient's body tissue and the plunger 182-2 is released. If the device 10-7 is properly secured to the patient's body tissue (so that an appropriate vacuum pressure can be generated by the pump 182 between the device 10-7 and the body tissue), the biasing element 182-4 will attempt to move the plunger 182-2 back out of the cylinder 182-1 and return it to its original extended position (FIG. 13B) when the plunger 182-2 is released, thereby generating a vacuum pressure between the device 10-7 and the body tissue. As the plunger 182-2 moves back out of the cylinder 182-1, the vacuum pressure will increase until the biasing element 182-4 can no longer move the plunger 182-2. As shown in FIG. 13D, the vacuum pressure generated between the device and the patient's body tissue holds the plunger 182-2 in a partially returned position and blocks the optical signal generated by the optical source 183 so that the optical receiver 184 receives no signal. The optical receiver 184, in turn, generates the second output signal which indicates that vacuum pressure is being sensed between the device 10-7 and the patient's body tissue. The distance the plunger 182-2 moves back from the fully depressed position within the cylinder 182-1 is determined by the relative vacuum pressure between the device 10-7 and the patient's body tissue, the relative ambient/atmospheric pressure and the force provided by the biasing element such as the compression spring 182-4. The location of the optical source 183 and the optical receiver 184 in the cylinder 182-1 should be selected so that the plunger 182-2 moves back and holds a position relative to the cylinder 182-1 where it blocks the optical signal S generated by the optical source 183 so that the optical receiver 184 cannot receive it, when an appropriate vacuum pressure is generated between the device 10-7 and the patient's body tissue.

If the device 10-7 is not properly secured to the patient's body tissue, the biasing element 182-4 will easily move the plunger 182-2 back out of the cylinder 182-1 and return it to its original extended position when the plunger 182-2 is released, as shown in FIG. 13B, because no vacuum pressure is generated between the device 10-7 and the body tissue. As the plunger 182-2 moves back to the extended position, it moves past the location of the optical source 183 and optical receiver 184 and allows the optical signal S generated by the optical source 183 to be received by the optical receiver 184. The optical receiver 184, in turn, generates the first output signal which indicates that no vacuum pressure is being sensed between the device 10-7 and the patient's body tissue.

Figure 14A:
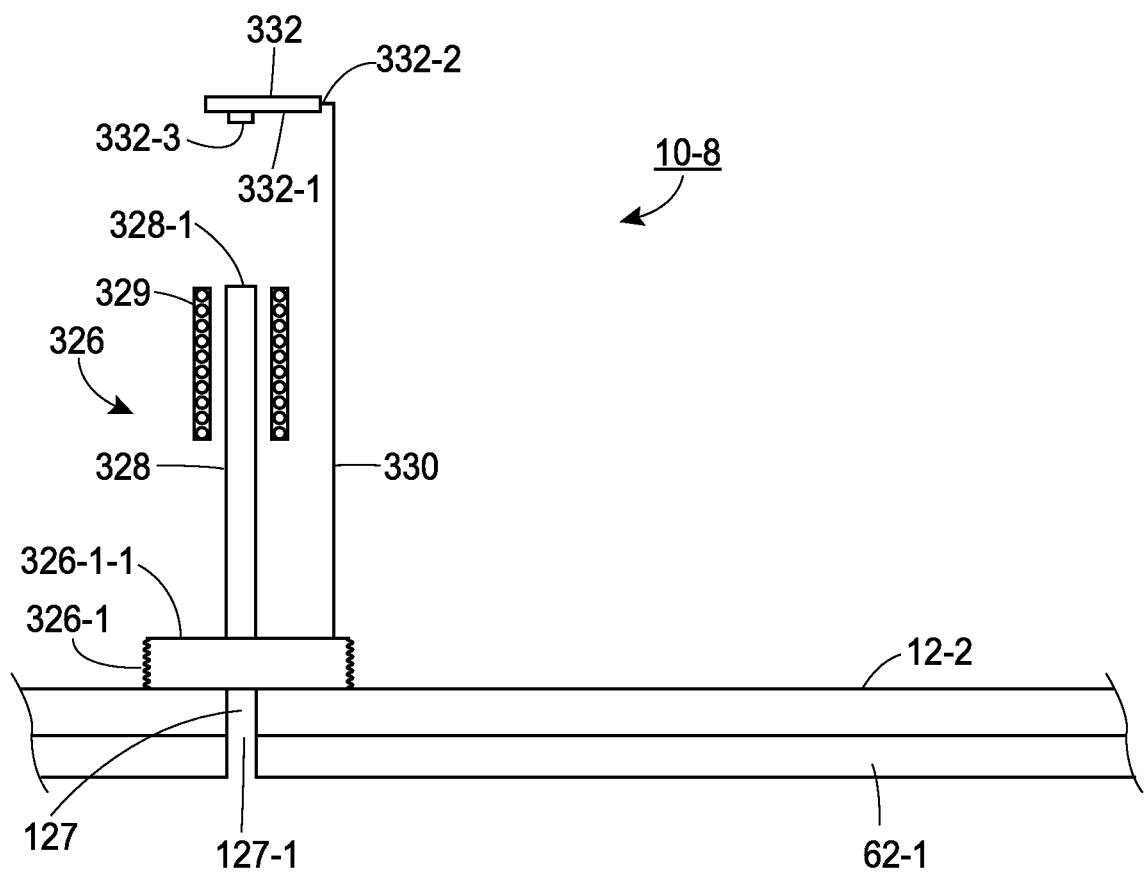
FIG. 14A is an enlarged cross-sectional view of a section of a drug delivery device that does not include a pneumatic system and which includes conventional adhesive layer disposed on or over a housing bottom wall of the device and another embodiment of the pressure sensor.

FIG. 14A shows another embodiment of the pressure sensor 326. The sensor 326 is described in conjunction with an embodiment of the drug delivery device 10-8 that does not include a pneumatic system and which includes a conventional adhesive layer 62-1 disposed on or over the housing bottom wall 12-2 to attach and retain the device 10-8 to the body tissue of the patient. The sensor 326 in such an application can be used to determine whether the drug delivery device 10-8 is properly attached to the body tissue of the patient by the adhesive layer 62-1. The pressure sensor 326 may comprise a flexible bellows 326-1, made for example of an elastomeric or a rubber material, having a one end closed by an end wall 326-1-1. The bellows may be constructed to have a spring constant. The bellows 326-1 is mounted so that it is exposed to the body tissue at the injection site. In some embodiments, the bellows 326-1 can be mounted on the bottom wall 12-2 of the device housing 12 over the pressure sensing 127 opening, which is aligned with a corresponding opening 127-1 in the adhesive layer 62-1. The aligned openings 127, 127-1 expose the sensor 326 to the underlying body tissue when attached thereto. In some embodiments, the bellows 326-1 may be constructed to be flat when the sensor 326 is inoperative and no force is being applied thereto, so that the sensor 326 is not sensitive to gravity and/or patient orientation. In other embodiments, a diaphragm (not shown) can be used in place of the bellows 326-1 although the bellows 326-1 can be displaced a further distance and therefore, improves sensing performance. A magnetic or conductive rod 328 extends up from the end wall 326-1-1 of the bellows 326-1. A selectively powered coil 329 surrounds the rod 329. In some embodiments a stop (not shown) may be provided above and spaced from the free end 328-1 of the rod 328. In other embodiments, the rod 328 may be electrically connected by a flexible wire 330 to a terminal 332-2 of a circuit 332-1 which is used to monitor the movement of the bellows 326-1 and therefore, vacuum pressure. The circuit 332-1 may be provided on a printed circuit 332 board disposed above and spaced from the free end 328-1 of the rod 328. The printed circuit board 332 may include an electrical contact 332-3 which faces and is aligned with the free end 328-1 of the rod 328. When the rod 328 engages the electrical contact 332-3 it closes the circuit 332-1.

Figure 14B:
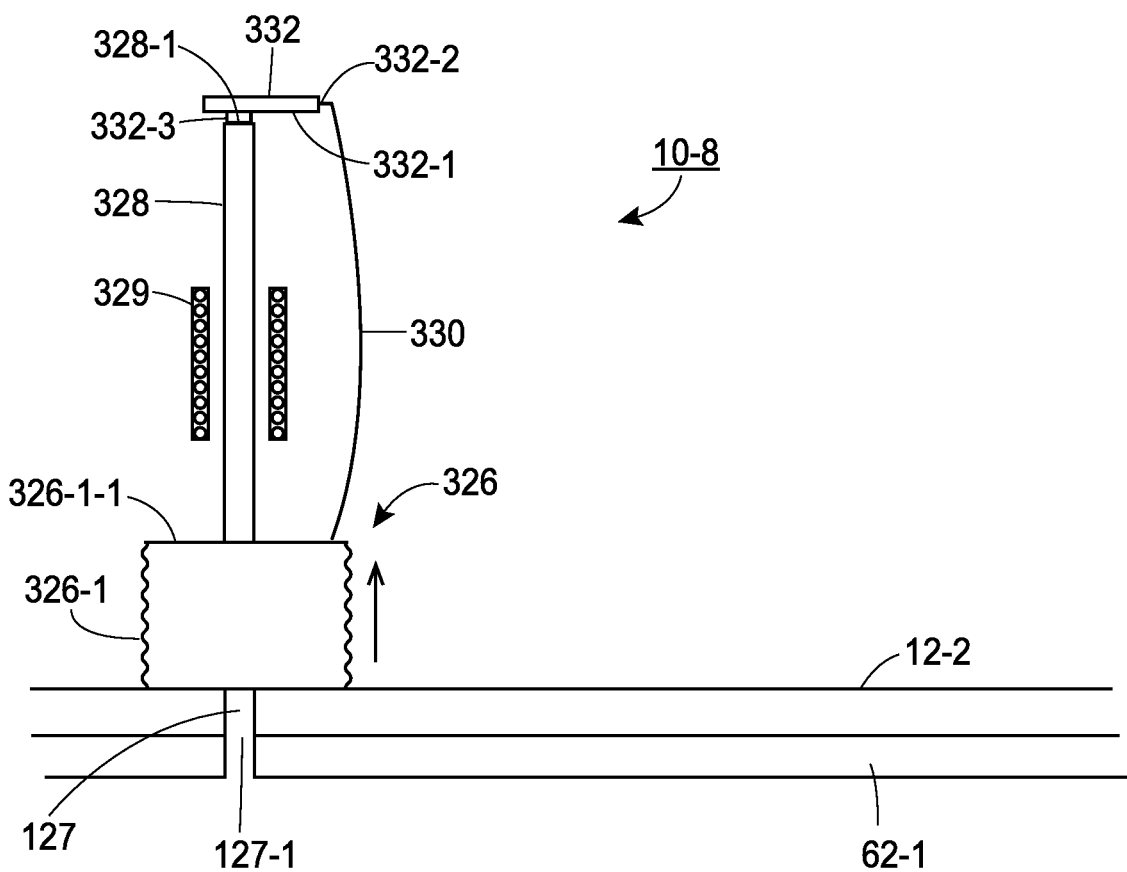
FIG. 14B is an enlarged cross-sectional view of the section of the drug delivery device of FIG. 14A, which illustrates the operation of the pressure sensor illustrated therein.

The pressure sensor 326 can be used to determine whether the drug delivery device 328 is properly attached to the body tissue of the patient. The pressure sensor 328 operates when the coil 329 is powered. The powered coil 329 generates a magnetic field (which provides a constant force) that pulls the rod 328, which is attached to or unitary with the end wall 326-1-1 of the bellows 328-1, toward the stop (not shown) or toward the overlying circuit contact 332-3. If the device 10-8 is properly attached to the body tissue of the patient, the adhesive layer 62-1 generates an air seal which allows a vacuum pressure to be generated between the interior side of the bellows 326-1-1 end wall (the exterior side of the bellows end wall 326-1-1 is exposed to atmospheric pressure) and area of the body tissue exposed by the pressure sensing openings 127, 127-1 in the housing bottom wall 12-2 and adhesive layer 62-1, as the bellows 326-1 is pulled away from the body tissue by the rod 328 when the coil 329 is powered. In operation, the coil 329 is powered with a pre-determined and limited amount of electrical power and will pull the rod 328 a distance proportional to the vacuum pressure behind the bellows 326-1. If the air seal is substantially leak-free, a significant and constant force will be required to pull bellows 326-1 due to the vacuum pressure generated behind the bellows 326-1. In some embodiments, the pre-determined electric pulse through the coil 329 will not create a magnetic field or force that is sufficient to pull the rod 328 all the way to the circuit contact 332-3 (or stop); thereby indicating that the device 10-8 is securely placed on the body tissue and the injection may proceed. Consequently, if the seal generated by the adhesive layer 62-1 is not substantially leak-free, very little force will be required to pull bellows 326 because the vacuum pressure behind the bellows 326-1 will be very small or non-existent. Consequently, the magnetic force created by the coil 329 will be sufficient to pull the rod 328 until the free end 328-1 thereof contacts the circuit contact 332-3 (or the stop) as shown in FIG. 14B, thereby indicating that the device 10-8 is not securely placed on the body tissue and the injection should not proceed.

The strength of the magnetic field of the coil 329 depends upon many factors including, without limitation the geometry of the coil 329, the number of turns of the coil 329, the voltage (power) supplied to the coil 329, and the material of the rod 328. The coil 329 selected and the power supplied to the coil 329 should allow the free end 328-1 of the rod 328 to almost engage the stop (not shown) or the circuit contact 332-3 at a desired threshold of vacuum pressure.

Figure 14C:
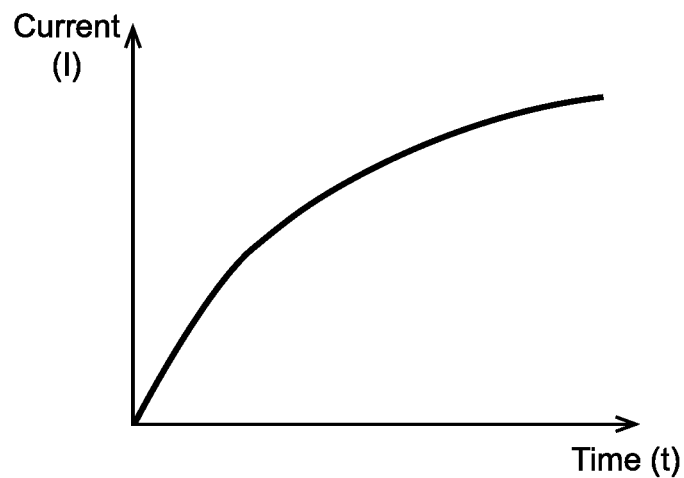
FIG. 14C graphically shows an example of a current profile for the pressure sensor of FIGS. 14A and 14B that indicates a proper seal between the device and the body tissue of the patient.
Figure 14D:
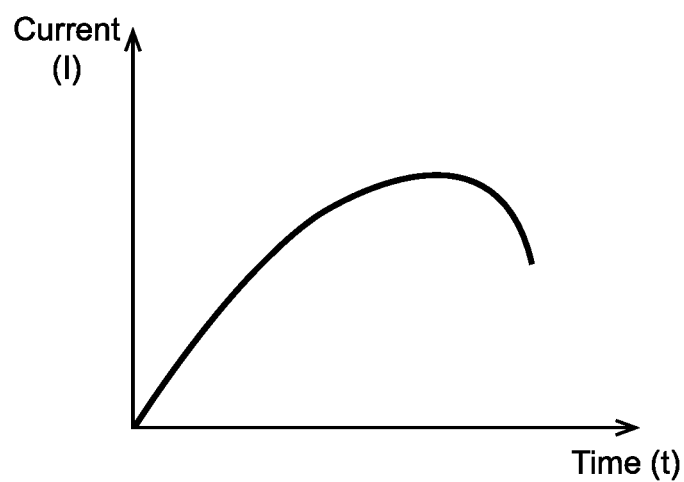
FIG. 14D graphically shows an example of a current profile for the pressure sensor that indicates an insufficient seal between the device and the body tissue of the patient.

The shape of the current profile through the coil 329 can be influenced by the rod 328 moving through the magnetic field. Therefore, in some embodiments pressure sensing can be performed indirectly by monitoring the shape of the current (I) through the coil 329 over time (t). If the rod 328 moves faster or slower through the magnetic field, it will carry inflections in the current waveform. FIG. 14C shows an example of a current profile for a rod 328 that does not move or which moves slowly through the magnetic field, thereby indicating a proper seal between the device 10-8 and the body tissue of the patient. When such a determination is made, the injection process can commence or continue on. FIG. 14D, shows an example of a current profile for a rod 328 that moves or moves quickly through the magnetic field, thereby indicating an insufficient seal between the device 10-8 and the body tissue of the patient. If such a determination is made, the injection process should not commence or should not continue on. Differentiating between the current profiles of a proper versus insufficient seal may, in some embodiments, involve sensing the current (calculated using the voltage drop across a small, for example, less than 50 ohm resistor in series with the coil) at a specific time point (e.g., in a certain number of milliseconds) after the initiation of the pulse or as complicated as a nearly complete profile comparison. The current can be sensed in some embodiments by calculating the voltage drop across a small resistor (e.g., less than 50 ohms) which is in series with the coil.

If current profile monitoring is used for pressure sensing, the earlier mentioned stop (not shown) can be used instead of the circuit 332-1 and contact 332-3 arrangement described earlier, as it is not needed to monitor the end of the rod travel. In some embodiments, the stop can be cushioned to maintain quiet operation of the sensor 326 during the injection process.

The sensor 326 described above and shown in FIGS. 14A and 14B may also be used with any of the previously described drug delivery devices that include the pneumatic system.

Figure 15A:
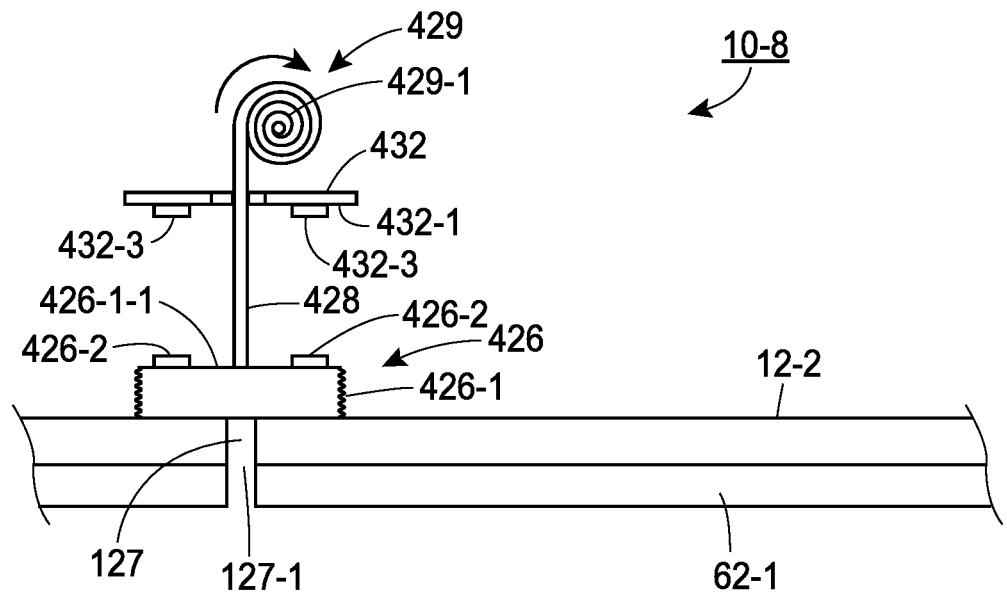
FIG. 15A is an enlarged cross-sectional view of a section of the drug delivery device of FIG. 14A with another embodiment of the pressure sensor.
Figure 15B:
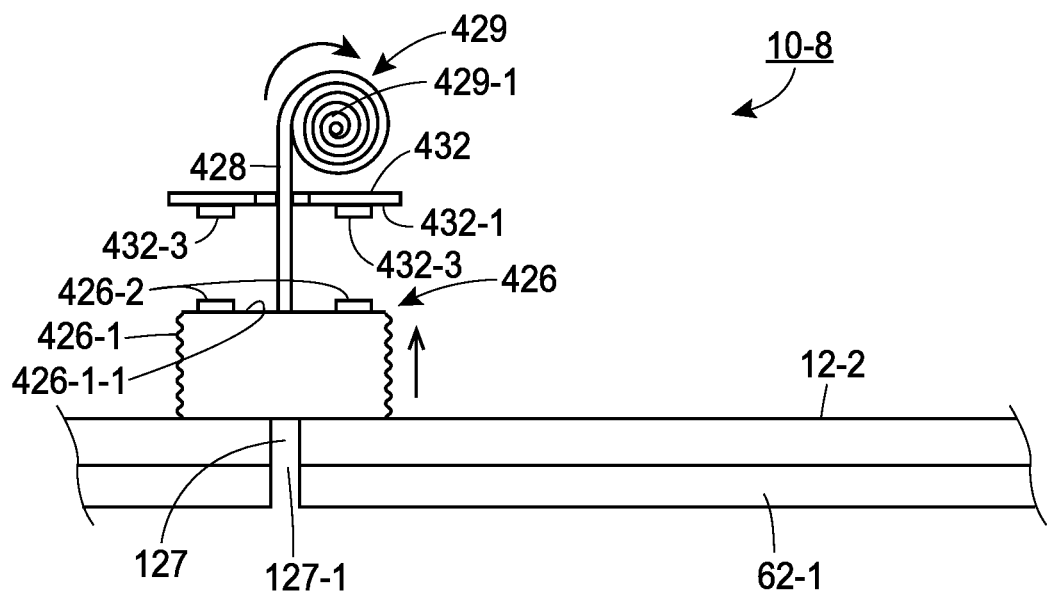
FIG. 15B is an enlarged cross-sectional view of the section of the drug delivery device of FIG. 15A, which illustrates the operation of the pressure sensor illustrated therein.

Referring to FIG. 15A, some embodiments of the sensor 426 can use a flexible wire-like cable 428 and an electric motor 429 in place of the rod 326 and coil 329 described above and shown in FIGS. 14A and 14B. One end of the cable 428 attaches to the end wall 426-1-1 of the bellows 426 and the other end attaches to the shaft 429-1 of the electric motor 429 (e.g., a DC motor). When the motor 429 is powered, the shaft 429 thereof turns and winds-up the cable 428, thereby pulling the bellows 426-1 away from the exposed area of the patient's body tissue, as shown in FIG. 15B. The motor 429 can be controlled to turn X number of revolutions as determined, for example, by an optical counter (not shown). Since the amount of current driving the motor 429 is proportional to the torque of the motor 429, the current (used to pull and wind the cable 428) can be used to indirectly monitor the sensor bellows 426-1. For example, if the current used exceeds a predetermined current threshold, this can indicate a proper seal between the device 10-8 and the patient's body tissue. The optical counter counts the desired number of turns of the motor while monitoring current. The current can be monitored in some embodiments by monitoring the voltage (which is proportional to the current) across a small resistor less than, for example, 50 ohms placed in series with the motor. If a poor seal has been achieved, which causes a leak, this in turn reduces the current draw expected after X turns, whereas a good seal will begin to increase current draw quickly because it's harder for the motor to rotate against the pressure differential. In other embodiments, the displacement of the sensor bellows 426-1 can be monitored by a circuit 432-1, which is closed when contacts 426-2 provided on the exterior surface of the bellows end wall 426-1-1 engage corresponding contacts 432-2 provided on the circuit 432-1. The circuit 432-1 may be provided on a printed circuit board 432 disposed above and spaced from the end wall 426-1-1 of the bellows 426.

Figure 16:
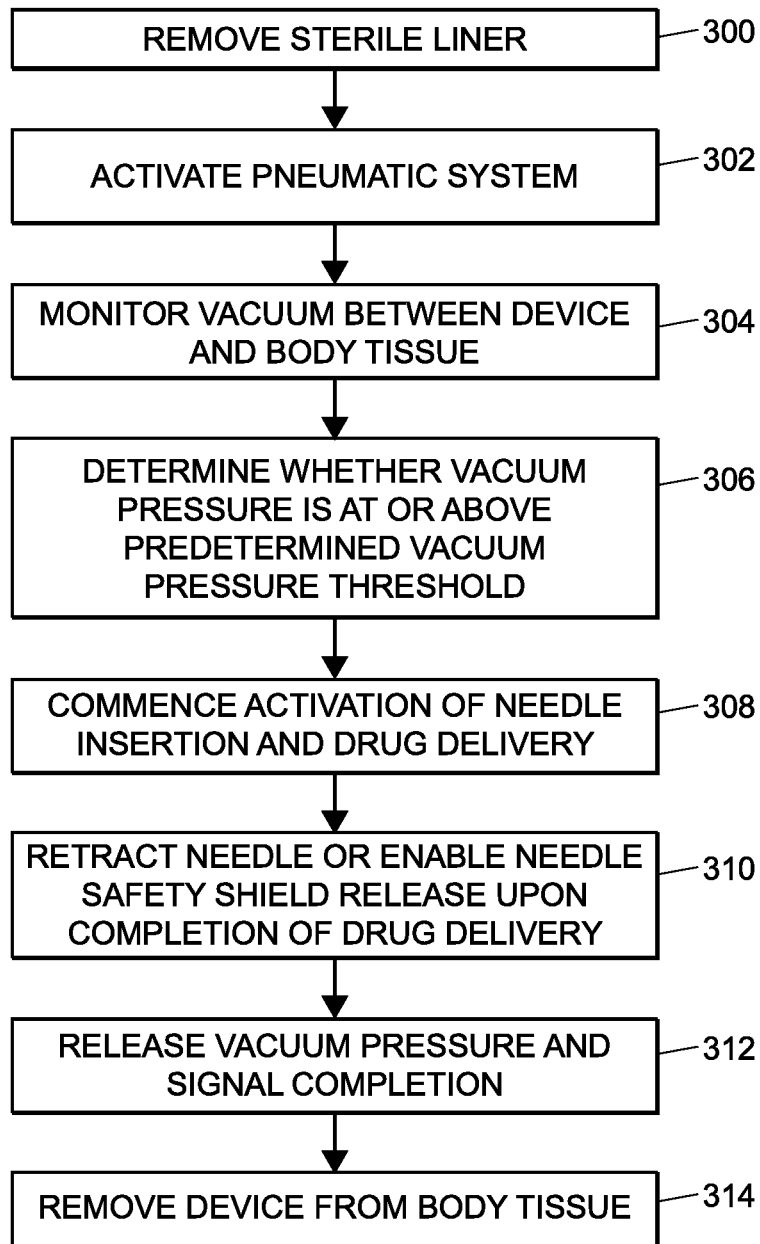
FIG. 16 is a flowchart illustrating an embodiment of a method for using the pneumatic system as body proximity sensor in a drug delivery device.

FIG. 16 is a flow chart illustrating an embodiment of a method for using the pneumatic system as body proximity sensor in a drug delivery device. The method commences in block 300 with the removal of the sterile liner from the adhesive laminate of the adhesive system. In block 302, the device is applied to the body tissue of the patient and the pneumatic system is activated. In other embodiments, the pneumatic system may be activated prior to applying the device to the body tissue of the patient. Once activated, the pneumatic system generates a vacuum between the device and the body tissue of the patient. In block 304, the vacuum pressure sensor monitors vacuum between the device and the body tissue of the patient. In block 306 a determination is made as to whether the vacuum pressure is at or above a predetermined vacuum pressure threshold. If the vacuum pressure is determined to be at or above the predetermined vacuum pressure threshold, the device will automatically commence or allow manual activation of needle insertion and drug delivery in block 308. Once drug delivery is completed, the device will automatically retract the injection needle or enable the release of the needle safety guard in block 310. In block 312, the pneumatic system will release the vacuum pressure and in some embodiments apply a positive fluid pressure, which indicates to the patient that the injection process is completed. In some embodiments, the device may be constructed to also provide a visual (e.g., display text and/or activate a light) and/or an audible signal (e.g, a beep and/or word) that the injection process has been completed. In block 314, the patient or operator removes the device from the body tissue.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosumab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK; AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:
  (i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;
  (ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;
  (iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);
  (iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;
  (v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;
  (vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;
  (vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and
  (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4137 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim®

(MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and systems have been described in terms of illustrative embodiments, they are not limited thereto. Rather, the appended claims should be construed broadly to include other variants and embodiments of same, which may be made by those skilled in the art without departing from the scope and range of equivalents of the devices, methods, and systems.

What is claimed is:

1. A drug delivery device comprising:
   a housing including a top wall, a bottom wall, and at least one side wall connecting the top wall and the bottom wall;
   a primary container disposed in the housing for containing a medicament;
   a needle for delivering the medicament from the primary container to a patient; and
   at least one pressure communication channel defined as at least one elongated groove extending along an outer surface of the bottom wall of the housing, wherein the at least one pressure communication channel is operative for distributing a negative fluid pressure across the outer surface of the bottom wall, the negative fluid pressure drawing the body tissue toward the bottom wall;
   wherein the at least one pressure communication channel comprises one or more of the following:

(a) a spiral-shaped groove having a first end disposed at a central area of the base and a second end disposed at a peripheral area of the bottom wall,
(b) two or more concentric grooves, or
(c) a plurality of separate grooves.

2. The drug delivery device of claim 1, further comprising:
an adhesive layer disposed over at least a portion of the bottom wall, the adhesive layer for adhesively attaching the device to body tissue, wherein the at least one pressure communication channel is operative for distributing the negative fluid pressure across the adhesive layer, the negative pressure across the adhesive layer drawing the body tissue against the adhesive layer.

3. The drug delivery device of claim 1, wherein the adhesive layer comprises at least one of: (a) a porous adhesive layer, (b) an adhesive layer that is disposed over the at least one pressure communication channel, and (c) an adhesive layer that is resilient.

4. The drug delivery device of claim 1, further comprising a port having an opening through the outer surface of the bottom wall in fluid communication with the at least one pressure communication channel, the port for applying the negative pressure to the at least one pressure communication channel.

5. The drug delivery device of claim 1, further comprising a negative pressure source in fluid communication with the at least one pressure communication channel.

6. The drug delivery device of claim 5, wherein the negative pressure source comprises one of (a) a vacuum pump, (b) a syringe, (c) an oxygen absorber, or (d) an air chamber that expands in volume from a minimum volume state to generate the negative pressure.

7. The drug delivery device of claim 6, including the vacuum pump, and further comprising a valve for adjusting the negative fluid pressure supplied by the vacuum pump.

8. The drug delivery device of claim 6, including the air chamber, wherein the air chamber comprises a biasing element for expanding the air chamber from the minimum volume state.

9. The drug delivery device of claim 6, including the air chamber and further comprising a user actuated first lever connected to the housing, the first lever for collapsing the air chamber.

10. The drug delivery device of claim 9, further comprising a second lever which facilitates movement of the first lever in the first direction by the user pinching the first and second levers together.

11. The drug delivery device of claim 6, including the air chamber and further comprising a plunger and a cylinder movably disposed relative to one another, wherein the air chamber is formed between the plunger and cylinder.

12. The drug delivery device of claim 6, including the air chamber, wherein the air chamber includes a valve or vent that allows air contained within the air chamber to pass therethrough when the air chamber is collapsed to the minimum volume state and which does not allow air to pass therethrough when the chamber is expanded from the minimum volume state.

13. The drug delivery device of claim 1, further comprising a controller for controlling the amount of the negative pressure.

14. The drug delivery device of claim 1, further comprising a fluid pressure distribution structure for distributing fluid pressure to the at least one pressure communication channel.

15. The drug delivery device of claim 14, wherein the fluid pressure distribution structure comprises one of (a) a serial structure having a primary fluid pressure delivery conduit and two or more secondary fluid pressure delivery conduits extending from the primary fluid pressure delivery conduit, or (b) a parallel structure comprising a plurality of fluid pressure delivery conduits extending from a source of fluid pressure.

16. The drug delivery device of claim 14, further comprising one or more valves disposed in the fluid pressure distribution structure.

17. The drug delivery device of claim 1, further comprising a sealing ring disposed around an injection needle entry site, or partially embedded in or disposed on, the base of the housing and surrounding an opening through which an injection needle of the device can extend through during needle insertion.

18. A method for attaching the drug delivery device of claim 1 to a patient, the method comprising:
placing the device above body tissue of the patient at a selected drug delivery site;
applying a negative fluid pressure to the at least one pressure communication channel extending along the outer surface of the bottom wall of the housing of the device, the at least one pressure communication channel distributing the negative fluid pressure across the outer surface of the bottom wall; and
drawing the body tissue of the patient against the bottom wall with the negative pressure.

19. The method of claim 18, further comprising applying a positive fluid pressure to the at least one pressure communication channel, the at least one pressure communication channel distributing the positive fluid pressure across the bottom wall at the end of injection to indicate dose delivery completion.

20. The drug delivery device of claim 1, further comprising a pressure sensor for sensing the proximity of the body tissue to the device, or whether there is negative fluid pressure drawing the body tissue against the bottom wall.

21. A drug delivery device comprising:
a housing including a top wall, a bottom wall, and at least one side wall connecting the top wall and the bottom wall;
a primary container disposed in the housing for containing a medicament;
a needle for delivering the medicament from the primary container to a patient;
at least one pressure communication channel defined as at least one groove extending along an outer surface of the bottom wall of the housing, wherein the at least one pressure communication channel is operative for distributing a negative fluid pressure across the outer surface of the bottom wall, the negative fluid pressure drawing the body tissue toward the bottom wall; and
a source of a positive fluid pressure, wherein the at least one pressure communication channel is further operative for distributing the positive fluid pressure across the bottom wall at the end of injection to indicate dose delivery completion.

22. A drug delivery device comprising:
a housing including a top wall, a base, and at least one side wall connecting the top wall and the base;
a primary container disposed in the housing for containing a medicament;
a needle for delivering the medicament from the primary container to a patient; and at least one pressure communication channel or aperture defined by the base, wherein the at least one pressure communication channel or aperture is operative for distributing a negative fluid pressure across the base, the negative fluid pressure drawing the body tissue toward the base;

a negative pressure source in fluid communication with the at least one pressure communication channel, wherein the negative pressure source comprises an air chamber that expands in volume from a minimum volume state to generate the negative pressure; and further comprising one or more of:
- (a) a user actuated first lever connected to the housing, the first lever for collapsing the air chamber;
- (b) a plunger and a cylinder movably disposed relative to one another, wherein the air chamber is formed between the plunger and cylinder; or
- (c) the air chamber includes a valve or vent that allows air contained within the air chamber to pass therethrough when the air chamber is collapsed to the minimum volume state and which does not allow air to pass therethrough when the chamber is expanded from the minimum volume state.

* * * * *